(12) United States Patent
Maring et al.

(10) Patent No.: US 6,593,314 B1
(45) Date of Patent: Jul. 15, 2003

(54) NEURAMINIDASE INHIBITORS

(75) Inventors: Clarence J. Maring, Palatine, IL (US); Vincent L. Giranda, Gurnee, IL (US); Yu Gui Gu, Libertyville, IL (US); Stephen Hanessian, Beaconsfield (CA); Dale J. Kempf, Libertyville, IL (US); Darold L. Madigan, Elk Grove Village, IL (US); Kent Stewart, Gurnee, IL (US); Vincent S. Stoll, Libertyville, IL (US); Minghua Sun, Libertyville, IL (US); Gary T. Wang, Niles, IL (US); Jianchio Wang, Montreal (CA); Chen Zhao, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/668,245

(22) Filed: Sep. 22, 2000

Related U.S. Application Data

(60) Provisional application No. 60/160,350, filed on Oct. 19, 1999, now abandoned, and provisional application No. 60/161,780, filed on Oct. 27, 1999, now abandoned.

(51) Int. Cl.[7] ............... A61K 31/655; A61K 31/215; A61K 31/95; C07D 303/00; C07C 229/00

(52) U.S. Cl. ............... 514/151; 514/183; 514/529; 514/563; 514/567; 549/512; 552/10; 560/125; 562/507

(58) Field of Search ............... 562/567, 507; 514/529, 156, 183, 563; 560/125; 549/512; 552/10

(56) References Cited

U.S. PATENT DOCUMENTS

| | | | |
|---|---|---|---|
| 5,453,533 A | | 9/1995 | Luo et al. |
| 5,512,596 A | | 4/1996 | Kim et al. |
| 5,602,277 A | | 2/1997 | Babu et al. |
| 5,648,379 A | | 7/1997 | Itzstein et al. |
| 5,763,483 A | | 6/1998 | Bischofberger et al. |
| 5,859,284 A | * | 1/1999 | Kent et al. ........ 560/125 |
| 5,866,601 A | * | 2/1999 | Lew et al. ........ 514/459 |
| 5,886,213 A | * | 3/1999 | Kent et al. ........ 560/156 |
| 5,919,819 A | | 7/1999 | Andrews et al. |
| 5,952,375 A | * | 9/1999 | Bischofberger et al. .... 514/459 |

FOREIGN PATENT DOCUMENTS

| | | |
|---|---|---|
| EP | 0 539 204 | 4/1993 |
| EP | 0 823 428 | 2/1998 |
| EP | 0 882 721 | 12/1998 |
| GB | 2292081 | 2/1996 |
| WO | 92/06691 | 4/1992 |
| WO | 95/18800 | 7/1995 |
| WO | 95/20583 | 8/1995 |
| WO | 96/26933 | 9/1996 |
| WO | 96/30329 | 10/1996 |
| WO | 96/36628 | 11/1996 |
| WO | 97/06157 | 2/1997 |
| WO | 97/32214 | 9/1997 |
| WO | 97/47194 | 12/1997 |
| WO | 98/03487 | 1/1998 |
| WO | 98/06712 | 2/1998 |
| WO | 98/07685 | 2/1998 |
| WO | 98/11083 | 3/1998 |
| WO | 98/17647 | 4/1998 |
| WO | 98/21243 | 5/1998 |
| WO | 99/06369 | 2/1999 |
| WO | 99/14185 | 3/1999 |
| WO | 99/14191 | 3/1999 |
| WO | 99/31047 | 6/1999 |
| WO | 99/33781 | 7/1999 |

OTHER PUBLICATIONS

Kim et al, Structure–Activity Relationship Studies of Novel Carbocyclic Influenza Neuraminidase Inhibitors, 1998, Journal of Medicinal Chemistry, 41, pp. 2451–2460.*

Nishimura, et al., *Natural Product Letters*, vol. 1, 1992, pp. 39–44.

Air, et al., *Virology*, vol. 177, 1990, pp. 578–587.

Atigadda, et al., *Journal of Med. Chem.*, vol. 42, 1999, pp. 2332–2343.

Bartlett, et al., *J. Am. Chem. Soc.*, vol. 108, 1986, pp. 8068–8071.

Berchtold, et al., *Journal of Org. Chem.*, vol. 50, 1985, pp. 888–890.

(List continued on next page.)

*Primary Examiner*—Johann Richter
*Assistant Examiner*—Paul A. Zucker
(74) *Attorney, Agent, or Firm*—B. Coregory Donner

(57) ABSTRACT

The present invention provides compounds of formula Ia and Ib

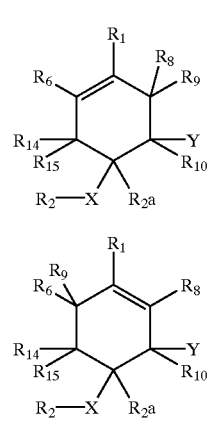

or a pharmaceutically acceptable salt, prodrug, or ester thereof, useful in the inhibition of neuraminidase enzymes from disease-causing microorganisms, especially influenza neuraminidase, pharmaceutical formulations containing same, processes and intermediates for preparing said compounds, as well as methods of using said compounds, including preventing and treating diseases caused by microorganisms having said neuraminidase enzyme.

15 Claims, No Drawings

OTHER PUBLICATIONS

Chandler, et al., *J. Chem. Soc. Perkin Trans. 1*, 1995, pp. 1189–1197.

Czollner, et al., *Helvetica Chimica Acta*, vol. 73, 1990, pp. 1338–1358.

Glanzer, et al., *Helvetica Chimica Acta*, vol. 74, 1991, pp. 343–369.

Greene, et al., *Protective Groups in Organic Synthesis*, 2nd edition, John Wiley & Sons, New York (1991), pp. 10–86.

IUPAC 1974 Recommendations for Section E, Fundamental Stereochemistry, Pure Appl. Chem., vol. 45, 1976, pp. 13–30.

Kim, et al., *Antiviral Chemistry & Chemotherapy*, vol. 10, No. 4, 1999, pp. 141–154.

Lew, et al., *Bioorganic & Medicinal Chemistry Letters*, vol. 10, 2000, pp. 1257–1260.

Lew, et al., *Bioorganic & Medicinal Chemistry Letters*, vol. 7, No. 14, 1997, pp. 1843–1846.

Morrison, et al., *Comments Mol. Cell. Biophys.*, vol. 2, No. 6, 1985, pp. 347–368.

Morrison, *Trends Biochem. Sci.*, vol. 7, 1982, pp. 102–105.

Nishimura, et al., *Natural Product Letters*, vol. 1, 1992, pp. 33–38.

Prescott, Ed., *Methods in Cell Biology*, vol. XIV, Academic Press, New York, N.Y., 1976, p. 33 et seq.

Schreiber, *Tetrahedron Letters*, vol. 24, 1983, p. 2363.

Vorwerk, et al., *Angewandte Chemie Int. Ed.*, vol. 37, No. 12, 1998, pp. 1732–1735.

* cited by examiner

NEURAMINIDASE INHIBITORS

This application claims the benefit of U.S. provisional Application for Patent No. 60/160,350, filed Oct. 19, 1999, now abandoned, and also claims the benefit of U.S. Provisional Application for patent No. 60/161,780, filed Oct. 27, 1999, now abandoned.

TECHNICAL FIELD

The present invention relates to novel compounds, compositions, and methods for inhibiting neuraminidase, especially influenza neuraminidase. The invention also contemplates compositions and methods for preventing and treating an influenza infection, and processes for making such compounds, and synthetic intermediates employed in these processes.

BACKGROUND OF THE INVENTION

Many disease-causing microorganisms possess a neuraminidase (also known as sialidase) which is involved in the replication process of the microorganism. In particular, viruses of the orthomyxovirus and paramyxovirus groups possess a neuraminidase. Diseases associated with paramyxoviruses include RSV (respiratory syncytial virus-related diseases), pneumonia and bronchiolitis (associated with paramyxovirus type 3) and laryngotracheobronchitis (associated with paramyxovirus type 1). Some of the more important disease-causing microorganisms in man and/or animals which possess a neuraminidase include *Vibrio cholerae*, *Clostridium perfringens*, *Streptococcus pneumoniae*, *Arthrobacter sialophilus*, influenza virus, parainfluenza virus, mumps virus, Newcastle disease virus, fowl plague virus, equine influenza virus and Sendai virus.

Mortality due to influenza is a serious problem throughout the world. The disease is devastating to man, lower mammals and some birds. Although vaccines containing attenuated influenza virus are available, those vaccines only provide immunological protection toward a few influenza strains and are less effective in otherwise immunologically compromised populations such as the elderly, young children, and in those who suffer from chronic respiratory illness. The productivity loss from absence due to sickness from influenza virus infection has been estimated to be more than $1 billion per year.

There are two major strains of influenza virus (designated A and B). Currently, there are only a few pharmaceutical products approved for treating influenza. These include amantadine and rimantadine, which are active only against the A strain of influenza viruses, and ribavirin, which suffers from dose-limiting toxicity. Mutant virus which is resistant to amantadine and rimantadine emerges quickly during treatment with these agents.

Very recently the first influenza neuraminidase inhibitor, zanamivir, was approved. However, it can only be administered by inhalation. Therefore, there is a continuing need for improved agents for treatment and/or prevention of influenza infection. Neuraminidase is one of two major viral proteins which protrude from the envelope of influenza virus. During the release of progeny virus from infected cells, neuraminidase cleaves terminal sialic acid residues from glycoproteins, glycolipids and oligosaccharides on the cell surface. Inhibition of neuraminidase enzymatic activity leads to aggregation of progeny virus at the surface. Such virus is incapable of infecting new cells, and viral replication is therefore retarded or blocked. X-ray crystallographic studies and sequence alignments have shown that the residues which directly contact the sialic acid portion of the substrate are strictly conserved in the neuraminidase from all A and B influenza strains. Thus, a compound which binds to the sialic acid binding region of the neuraminidase active site will block the replication of both the A and B strains of influenza virus. Compounds which are influenza neuraminidase inhibitors will be useful for the prevention of influenza infection and will be useful for the treatment of influenza infection.

The following references disclose neuraminic acid derivatives with the disclosed utility listed after each reference:

L. Von Itzstein, et al., European Patent Application No. EP539204, published Apr. 28, 1993 (antiviral agent);

T. Honda, et al., European Patent Application No. EP823428, published Feb. 11, 1998 (sialidase inhibitor; influenza treatment);

T. Honda, et al., International Patent Application No. WO98/06712, published Feb. 19, 1998 (sialidase inhibitor; influenza remedy);

L. Von Itzstein, et al., International Patent Application No. WO95/20583, published Aug. 3, 1995 (viral neuraminidase inhibitor; influenza treatment);

P. Smith, International Patent Application No. WO95/18800, published Jul. 13, 1995 (viral neuraminidase inhibitor);

P. Colman, et al., International Patent Application No. WO92/06691, published Apr. 30, 1992 (viral neuraminidase inhibitor);

L. Von Itzstein, et al., U.S. Pat. No. 5,648,379, issued Jul. 15, 1997 (influenza treatment);

P. Reece, et al., International Patent Application No. WO97/32214, published Sep. 4, 1997 (bind to influenza virus neuraminidase active site); and P. Reece, et al., International Patent Application No. WO98/21243, published May 23, 1998 (anti-influenza agent).

The following references disclose sialic acid derivatives with the disclosed utility listed after each reference:

Y. Ohira, et al., International Patent Application No. WO98/11083, published Mar. 19, 1998 (antiviral agent);

Y. Ohira, European Patent Application No. EP882721, published Dec. 9, 1998 (antiviral agent); and B. Glanzer, et al., Helvetica Chimica Acta 74 343–369 (1991) (*Vibrio cholerae* neuraminidase inhibitor).

The following references disclose benzene derivatives, cyclohexane derivatives or cyclohexene derivatives with the disclosed utility listed after each reference:

Y. Babu, et al., U.S. Pat. No. 5,602,277, issued Feb. 11, 1997 (neuraminidase inhibitors);

M. Luo, et al., U.S. Pat. No. 5,453,533, issued Sep. 26, 1995 (influenza neuraminidase inhibitor; influenza treatment);

Y. Babu, et al., International Patent Application No. WO96/30329, published Oct. 3, 1996 (neuraminidase inhibitor; viral infection treatment);

N. Bischofberger, et al., U.S. Pat. No. 5,763,483, issued Jun. 9, 1998 (neuraminidase inhibitor);

C. Kim, et al., International Patent Application No. WO99/31047, published Jun. 24, 1999 (neuraminidase inhibitor; influenza treatment);

V. Atigadda, et al., J. Med. Chem. 42 2332–2343 (1999) (influenza neuraminidase inhibitor); and K. Kent, et al., International Patent Application No. 98/07685, published Feb. 26, 1998 (intermediates for the preparation of neuraminidase inhibitors).

C. Kim, et al., International Patent Application No. WO98/17647, published Apr. 30, 1998 discloses piperidine derivatives that are useful as neuraminidase inhibitors.

N. Bischofberger, et al., International Patent Application No. WO96/26933, published Sep. 6, 1996 and N.

Bischofberger, et al., International Patent Application No. WO99/14185, published Mar. 25, 1999 disclose various substituted 6-membered ring compounds that are useful as neuraminidase inhibitors.

The following references disclose dihydropyran derivatives that are useful as viral neuraminidase inhibitors:

D. Andrews, et al., International Patent Application No. WO97/06157, published Feb. 20, 1997 and U.S. Pat. No. 5,919,819, issued Jul. 6, 1999; and P. Cherry, et al., International Patent Application No. WO96/36628, published Nov. 21, 1996.

C. Kim, et al., U.S. Pat. No. 5,512,596, issued Apr. 30, 1996 discloses 6-membered aromatic ring derivatives that are useful as neuraminidase inhibitors.

G. Diana, et al., International Patent Application No. WO98/03487, published Jan. 29, 1998 discloses substituted pyridazines that are useful for treatment of influenza.

B. Horenstein, et al., International Patent Application No. WO99/06369, published Feb. 11, 1999 discloses piperazine derivatives that are useful as neuraminidase inhibitors.

The following references disclose substituted cyclopentanes that are useful as neuraminidase inhibitors and treatments for influenza:

Y. Babu, et al., International Patent Application No. WO97/47194, published Dec. 18, 1997; and Y. Babu, et al., International Patent Application No. WO99/33781, published Jul. 8, 1999.

L. Czollner, et al., Helvetica Chimica Acta 73 1338–1358 (1990) discloses pyrrolidine analogs of neuraminic acid that are useful as *Vibrio cholerae* sialidase inhibitors.

W. Brouillette, et al., International Patent Application No. WO99/14191, published Mar. 25, 1999, discloses substituted pyrrolidin-2-one compounds that are useful as neuraminidase inhibitors and treatments for influenza.

The following references disclose siastatin B analogs that are useful as neuraminidase inhibitors:

Y. Nishimura, et al., Natural Product Letters 1 39–44 (1992); and

Y. Nishimura, et al., Natural Product Letters 1 33–38 (1992).

C. Penn, UK Patent Application No. GB2292081, published Feb. 14, 1996 discloses the use of a neuraminidase inhibitor in combination with an influenza vaccine.

Thus, it would be an important contribution to the art to provide compounds which are neuraminidase inhibitors.

SUMMARY OF THE INVENTION

The present invention provides compounds of formula Ia and Ib

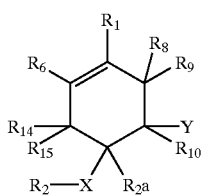

Ia

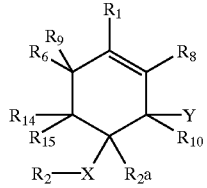

Ib or a pharmaceutically acceptable salt, ester, or prodrug thereof, wherein $R^1$ is selected from the group consisting of
(a) —$CO_2H$,
(b) —$SO_3H$,
(e) —$SO_2H$,
(f) —$PO_3H_2$,
(g) —$PO_2H$,
(h) tetrazolyl,
(i) —C(=O)—NH—S(O)$_2$—$R^{11}$, and
(j) —$SO_2$N(T—$R^{11}$)$R^{12}$;
wherein
T is selected from the group consisting of
(i) a bond, (ii) —C(=O)—, (iii) —C(=O)O—, (iv) —C(=O)S—, (v) —C(=O)NR$^{36}$—, (vi) —C(=S)O—, (vii) —C(=S)S—, and (viii) —C(=S)NR$^{36}$—;

$R^{11}$ is selected from the group consisting of
(i) $C_1$–$C_{12}$ alkyl, (ii) $C_2$–$C_{12}$ alkenyl, (iii) cycloalkyl, (iv) (cycloalkyl)alkyl, (v) (cycloalkyl)alkenyl, (vi) cycloalkenyl, (vii) (cycloalkenyl)alkyl, (viii) (cycloalkenyl)alkenyl, (ix) aryl, (x) (aryl)alkyl, (xi) (aryl) alkenyl, (xii) heterocyclic, (xiii) (heterocyclic) alkyl, and (xiv) (heterocyclic)alkenyl; and $R^{12}$ and $R^{36}$ are independently selected from the group consisting of
(i) hydrogen, (ii) $C_1$–$C_{12}$ alkyl, (ii) $C_2$–$C_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl) alkenyl, (ix) aryl, (xi) (aryl)alkyl, (xii) (aryl) alkenyl, (xiii) heterocyclic, (xiv) (heterocyclic) alkyl, and (xv) (heterocyclic)alkenyl;

X is selected from the group consisting of
(a) —C(=O)—N(R*)—, (b) —N(R*)—C(=O)—, (b) —C(=S)—N(R*)—, (d) —N(R*)—C(=S)—, (e) —N(R*)$_{SO2}$—, and (f) —SO$_2$—N(R*)—, wherein R* is hydrogen, $C_1$–$C_3$ loweralkyl or cyclopropyl;

$R^2$ is selected from the group consisting of
(a) hydrogen, (b) $C_1$–$C_6$ alkyl, (c) $C_2$–$C_6$ alkenyl, (d) $C_3$–$C_6$ cycloalkyl, (e) $C_5$–$C_6$ cycloalkenyl, (f) halo $C_1$–$C_6$ alkyl and (g) halo $C_2$–$C_6$ alkenyl;

or $R^2$—X— is

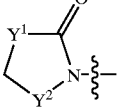

wherein $Y^1$ is —$CH_2$—, —O—, —S— or —NH— and $Y^2$ is —C(=O)— or —C(R$^{aa}$)(R$^{bb}$)— wherein R$^{aa}$ and R$^{bb}$ are independently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R_{2a}$ is selected from the group consisting of
(a) hydrogen, (b) $C_1$–$C_6$ alkyl, (c) $C_2$–$C_6$ alkenyl, (d) halo $C_1$–$C_6$ alkyl, and (e) halo $C_2$–$C_6$ alkenyl;

$R_{14}$ and $R_{15}$ are independently selected from the group consisting of
(i) hydrogen, (ii) $C_1$–$C_{12}$ alkyl, (iii) haloalkyl, (iv) hydroxyalkyl, (v) thiol-substituted alkyl, (vi) $R^{37c}$O-substituted alkyl, (vii) $R^{37c}$S-substituted alkyl, (viii) aminoalkyl, (ix) ($R^{37c}$)NH-substituted alkyl, (x) ($R^{37a}$)($R^{37c}$)N-substituted alkyl, (xi) $R^{37a}$O—(O=)C-substituted alkyl, (xii) $R^{37a}$S—(O=)C-substituted alkyl, (xiii) $R^{37a}$O—(S=)C-substituted alkyl, (xiv) $R^{37a}$S—(S=)C-substituted alkyl, (xv) ($R^{37a}$O)$_2$—P(=O)-substituted alkyl, (xvi) cyanoalkyl, (xvii) $C_2$–$C_{12}$ alkenyl, (xviii) haloalkenyl, (xix) $C_2$–$C_{12}$ alkynyl, (xx) cycloalkyl, (xxi) (cycloalkyl)alkyl, (xxii) (cycloalkyl)alkenyl, (xxiii) (cycloalkyl)alkynyl, (xxiv) cycloalkenyl, (xxv) (cycloalkenyl)alkyl, (xxvi) (cycloalkenyl)alkenyl, (xxvii) (cycloalkenyl)-alkynyl, (xxviii) aryl, (xxxix)(aryl)alkyl, (xxx) (aryl)alkenyl, (xxxi) (aryl)alkynyl, (xxxii) heterocyclic, (xxxiii) (heterocyclic)alkyl, (xxxiv) (heterocyclic)alkenyl, (xxxv) (heterocyclic)alkynyl, (xxxvi) —O-alkyl, (xxxvii) —NHalkyl, (xxxviii) —NH$_2$, (xxxix) —N(alkyl)$_2$, (xxxx) —OH, (xxxxi) —NHacyl, (xxxxii) —Nalkylacyl, (xxxxiii) —NHcarbamoyl, (xxxxiv) —Nalkylcarbamoyl, (xxxxv) —NHcarbamidyl, and (xxxxvi) —Nalkylcarbamidyl;

$R^{37a}$ is selected from the group consisting of
(i) hydrogen, (ii) $C_1$–$C_{12}$ alkyl, (iii) haloalkyl, (iii) hydroxyalkyl, (v) alkoxyalkyl, (vi) $C_2$–$C_{12}$ alkenyl, (vii) haloalkenyl, (viii) $C_2$–$C_{12}$ alkynyl, (x) cycloalkyl, (x) (cycloalkyl)alkyl, (xi) (cycloalkyl)alkenyl, (xii) (cycloalkyl)alkynyl, (xiii) cycloalkenyl, (xiv) (cycloalkenyl)alkyl, (xv) (cycloalkenyl)alkenyl, (xvi) (cycloalkenyl)alkynyl, (xvii) aryl, (xviii) (aryl)alkyl, (xix) (aryl)alkenyl, (xx) (aryl)alkynyl, (xxi) heterocyclic, (xxii) (heterocyclic)alkyl, (xxiii) (heterocyclic)alkenyl and (xxiv) (heterocyclic)alkynyl;

$R^{37c}$ at each occurrence is independently selected from the group consisting of
(i) hydrogen, (ii) $C_1$–$C_{12}$ alkyl, (iii) haloalkyl, (iv) $C_2$–$C_{12}$ alkenyl, (v) haloalkenyl, (vi) $C_2$–$C_{12}$ alkynyl, (vii) cycloalkyl, (viii) (cycloalkyl)alkyl, (ix) (cycloalkyl)-alkenyl, (x) (cycloalkyl)alkynyl, (xii) cycloalkenyl, (xii) (cycloalkenyl)alkyl, (xiii) (cycloalkenyl) alkenyl, (xiv) (cycloalkenyl)alkynyl, (xv) aryl, (xvi) (aryl)alkyl, (xvii) (aryl)alkenyl, (xviii) (aryl)alkynyl, (xix) heterocyclic, (xx) (heterocyclic)alkyl, (xxi) (heterocyclic)-alkenyl, (xxii) (heterocyclic)alkynyl, (xxiii) —C(=O)—R$^{14}$, (xxiii) —C(=S)—R$^{14}$, (xxv) —S(O)$_2$—R$^{14}$ and (xxvi) hydroxyalkyl;

Y is selected from the group consisting of
(a) $C_2$–$C_5$ alkenyl,
(b) $C_2$–$C_5$ haloalkenyl,
(c) $C_2$–$C_5$ alkynyl,
(d) $C^5$ cycloalkenyl,
(e) $C_5$ cycloalkenyl-$C_1$-to-$C_3$-alkyl,
(f) $C^5$ cycloalkenyl-$C_2$-to-$C_3$-alkenyl,
(g) phenyl,
(h) halo-substituted phenyl,
(i) —(CHR$^{39}$)$_n$C(=Q$^2$)R$^{22}$, and
(j) a heterocyclic ring having from 3 to 6 ring atoms;
with the proviso that Y is not

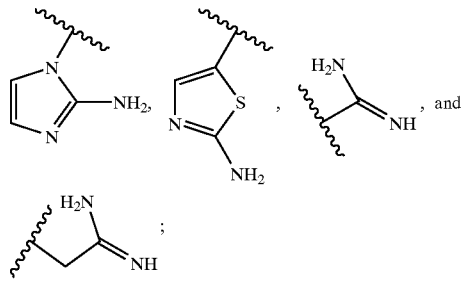

wherein n is 0, 1, or 2; and $Q^2$ is O, S, NR$^{25}$, or CHR$^{26}$;
$R^{22}$ is selected from the group consisting of
(i) hydrogen, (ii) methyl, (iii) ethyl, (iv) n-propyl, (v) isopropyl, (vi) hydroxy, (vii) thiol, (viii) methoxy, (ix) ethoxy, (x) n-propoxy, (xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —N(R$^{28a}$)(R$^{28b}$), (xxiii) —CH$_2$R$^{29}$, (xxiv) aminomethyl, (xxv) hydroxymethyl, (xxvi) thiolmethyl, (xxvii) —NHNH$_2$, (xxviii) —N(CH$_3$)NH$_2$, or (xxix) —NHNH(CH$_3$);

$R^{25}$ is hydrogen, hydroxy, methyl, ethyl, amino, —CN, or —NO$_2$;

$R^{26}$ is hydrogen, methyl or ethyl;

$R^{28a}$ is hydrogen, hydroxy, methyl, ethyl, amino, —NHCH$_3$, —N(CH$_3$)$_2$, methoxy, ethoxy, or —CN;

$R^{28b}$ is hydrogen, methyl or ethyl;

or $R^{28a}$, $R^{28b}$ and the nitrogen to which they are bonded taken together represent azetidinyl;

$R^{29}$ is hydrogen, hydroxy, thiol, methyl, ethyl, amino, methoxy, ethoxy, methylthio, ethylthio, methylamino or ethylamino;

with the proviso that when $Q^2$ is CHR$^{26}$ then $R^{22}$ is selected from the group consisting of hydrogen, —CH$_3$, —C$_2$H$_5$, —C$_3$H$_7$, —OCH$_3$, —SCH$_3$, —O—C$_2$H$_5$, and —S—C$_2$H$_5$;

$R^6$ is independently selected from the group consisting of
(a) hydrogen, (b) $C_1$–$C_{12}$ alkyl, (c) $C_2$–$C_{12}$ alkenyl, (d) cycloalkyl, (e) (cycloalkyl)alkyl, (f) (cyclo alkyl)alkenyl, (g) cycloalkenyl, (h) (cycloalkenyl)alkyl, (i) (cycloalkenyl)alkenyl, (j) aryl, (k) (aryl)alkyl, (l) (aryl)alkenyl, (m) heterocyclic, (m) (heterocyclic)alkyl, and (o) (heterocyclic)alkenyl; and $R^8$ and $R^9$ are independently selected from the group consisting of
(a) hydrogen, (b) $C_1$–$C_6$ alkyl, (c) $C_2$–$C_6$ alkenyl, (d) $C_3$–$C_6$ cycloalkyl, (e) $C_3$–$C_6$ cycloalkenyl, (f) fluorine, and (g) —NH$_2$,
with the proviso that the total number of atoms, other than hydrogen, in each of $R^8$ and $R^9$, is 6 atoms or less; and $R^{10}$ is selected from the group consisting of
(a) hydrogen,
(b) $C_1$–$C_6$ alkyl, (c) —NH$_2$, and
(d) —OH with the proviso that the total number of atoms, other than hydrogen, in each of R$^{10}$, is 6 atoms or less.

Further provided are compounds of formulas Ia' and Ib'

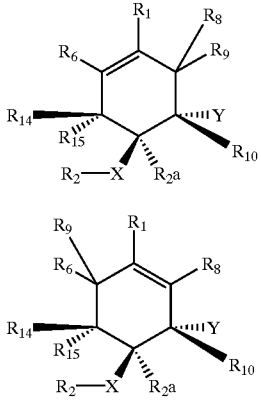

wherein the substituents are as defined hereinabove.

Still further provided are compounds of formula Ia" and Ib"

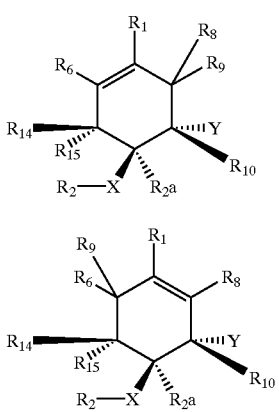

wherein all substituents are as defined hereinabove.

Still further provided are intermediates and processes for preparing compounds of formula Ia and Ib.

Additionally provided are methods of using compounds of formula I for the inhibition of a neuraminidase enzyme of disease-causing microorganisms; particularly viral neuraminidase, and, especially influenza neuraminidase.

Also provided are compounds of formula Ia and Ib that inhibit neuraminidase from both A and B strains of influenza.

Still further provided are methods for the prophylaxis and/or treatment of influenza infection in humans and other mammals using compounds of formula Ia and Ib.

Additionally provided are compounds that exhibit activity against influenza A virus and and influenza B virus by virtue of inhibiting influenza neuraminidase when such compounds are administered orally.

Also provided are compounds that can be effectively transported from the plasma into the lung bronchoaveolar fluid of humans and other mammals in order to block the replication of influenza virus in that tissue.

DETAILED DESCRIPTION OF THE INVENTION

The term "acid protecting group" as used herein refers to groups used to protect acid groups (for example, —CO$_2$H, —SO$_3$H, —SO$_2$H, —PO$_3$H$_2$, —PO$_2$H groups and the like) against undesirable reactions during synthetic procedures. Commonly used acid protecting groups are disclosed in T. H. Greene and P. G. M. Wuts, *Protective Groups in Organic Synthesis*. 2nd edition, John Wiley & Sons, New York (1991) which is incorporated herein by reference. Most frequently, such acid protecting groups are esters.

Such esters include:
  alkyl esters, especially loweralkyl esters, including, but not limited to, ethyl, n-propyl, isopropyl, n-butyl, sec-butyl, isobutyl, t-butyl, n-pentyl esters and the like;
  arylalkyl esters including, but not limited to, benzyl, phenethyl, 3-phenylpropyl, naphthylmethyl esters and the like, wherein the aryl part of the arylalkyl group is unsubstituted or substituted as previously defined herein;
  silylesters, especially, (tri-loweralkyl)silyl esters, (di-loweralkyl)(aryl)silyl esters and (loweralkyl)(di-aryl) silyl esters, including, but not limited to, trimethylsilyl, triethylsilyl, isopropyldimethylsilyl, t-butyldimethylsilyl, methyldiisopropylsilyl, methyldi-t-butylsilyl, triisopropylsilyl, methyldiphenylsilyl, isopropyldiphenylsilyl, butyldiphenylsilyl, phenyldiisopropylsilyl esters and the like; and the like.

Preferred acid protecting groups are loweralkyl esters.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonylchloride and the like, anhydrides derived from reaction of the carboxylic acid with N,N'-carbonyldiimidazole and the like, N-hydroxysuccinimide derived esters, N-hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "acyl" as used herein, refers to groups having the formula —C(=O)—R$^{95}$ wherein R$^{95}$ is hydrogen or an alkyl group. Preferred alkyl groups as R$^{95}$ are loweralkyl groups. Representative examples of acyl groups include groups such as, for example, formyl, acetyl, propionyl, and the like.

The term "acylalkyl" as used herein refers to an acyl group appended to an alkyl radical. Representative examples of acylalkyl groups include acetylmethyl, acetylethyl, propionylmethyl, propionylethyl and the like.

The term "acylamino" as used herein, refers to groups having the formula —NHR$^{89}$ wherein R$^{89}$ is an acyl group. Representative examples of acylamino include acetylamino, propionylamino, and the like.

The term "acyloxyalkyl" as used herein refers to an acyloxy group (i.e., R$^{95}$—C(O)—O— wherein R$^{95}$ is hydrogen or an alkyl group) which is appended to an alkyl radical. Representative examples of acyloxyalkyl include acetyloxymethyl, acetyloxyethyl, propioyloxymethyl, propionyloxyethyl and the like.

The term "alkenyl" as used herein, refers to a straight or branched chain hydrocarbon radical containing from 2 to 15 carbon atoms and also containing at least one carbon-carbon double bond. The term "lower alkenyl" refers to straight or branched chain alkenyl radicals containing from 2 to 6 carbon atoms. Representative examples of alkenyl groups include groups such as, for example, vinyl, 2-propenyl, 2-methyl-1-propenyl, 3-butenyl, 4-pentenyl, 5-hexenyl and the like.

The term "alkenylene" as used herein, refers to a divalent group derived from a straight or branched chain hydrocarbon containing from 2 to 15 carbon atoms and also containing at least one carbon-carbon double bond. The term "lower alkenylene" refers to a divalent group derived from a straight or branched chain alkene group having from 2 to 6 carbon atoms. Representative examples of alkenylene groups include groups such as, for example, —CH=CH—, —CH$_2$CH=CH—, —C(CH$_3$)=CH—, —CH$_2$CH=CHCH$_2$—, and the like.

The term "alkenyloxy" as used herein, refers to groups having the formula —OR$^{81}$ where R$^{81}$ is an alkenyl group.

The term "alkoxy" as used herein, refers to groups having the formula —OR$^{99}$ wherein R$^{99}$ is an alkyl group. Preferred R$^{99}$ groups are loweralkyl groups. Representative examples of alkoxy groups include groups such as, for example, methoxy, ethoxy, tert-butoxy, and the like.

The term "alkoxyalkoxy" as used herein, refers to groups having the formula —O—R$^{96}$—O—R$^{97}$ wherein R$^{97}$ is loweralkyl, as defined herein, and R$^{96}$ is a lower alkylene group. Representative examples of alkoxyalkoxy groups include groups such as, for example, methoxymethoxy, ethoxymethoxy, t-butoxymethoxy and the like.

The term "alkoxyalkyl" as used herein refers to an alkyl radical to which is appended an alkoxy group, for example, methoxymethyl, methoxylpropyl and the like.

The term "alkoxycarbonyl" as used herein, refers to groups having the formula, —C(=O)—R$^{80}$, where R$^{80}$ is an alkoxy group.

The term "alkoxycarbonylalkyl" as used herein, refers to groups having the formula, —C(=O)—R$^{79}$, appended to the parent molecular moiety through an alkylene linkage, where R$^{79}$ is an alkoxy group.

The term "alkoxycarbonyloxyalkyl" as used herein refers to an alkoxycarbonyloxy group (i.e., R$^{80}$—C(O)—O wherein R$^{80}$ is an alkoxy group) appended to an alkyl radical. Representative examples of alkoxycarbonyloxyalkyl include methoxycarbonyloxymethyl, ethoxycarbonyloxymethyl, methoxycarbonyloxyethyl and the like.

As used herein, the term "alkyl" refers to straight or branched chain hydrocarbon radicals containing from 1 to 12 carbon atoms. The term "loweralkyl" refers to straight or branched chain alkyl radicals containing from 1 to 6 carbon atoms. Representative examples of alkyl groups include groups such as, for example, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethylpropyl, n-hexyl, and the like. The hydrocarbon chains in alkyl groups or the alkyl portion of an alkyl-containing substituent can be optionally interrupted by one or two heteroatoms or heterogroups independently selected from the group consisting of oxygen, —N(R$^{27}$)— and sulfur wherein R$^{27}$ at each occurrence is independently hydrogen, loweralkyl, cycloalkyl, cycloalkylalkyl or arylalkyl and wherein two such heteroatoms or heterogroups are separated by at least one carbon atom.

The term "alkylamino" as used herein, refers to groups having the formula —NHR$^{91}$ wherein R$^{91}$ is an alkyl group. Preferred R$^{91}$ groups are loweralkyl groups. Representative examples of alkylamino include methylamino, ethylamino, and the like.

The term "alkylene" as used herein, refers to a divalent group derived from a straight or branched chain saturated hydrocarbon group having from 1 to 15 carbon. The term "lower alkylene" refers to a divalent group derived from a straight or branched chain saturated hydrocarbon group having from 1 to 6 carbon atoms. Representative examples of alkylene groups include groups such as, for example, methylene (—CH$_2$—), 1,2-ethylene (—CH$_2$CH$_2$—), 1,1-ethylene (—CH(CH$_3$)—), 1,3-propylene (—CH$_2$CH$_2$CH$_2$—), 2,2-dimethylpropylene (—CH$_2$C(CH$_3$)$_2$CH$_2$—), and the like. The hydrocarbon chains in alkylene groups or the alkylene portion of an alkylene-containing substituent can be optionally interrupted by one or two heteroatoms or heterogroups independently selected from the group consisting of oxygen, —N(R$^{27}$)— and sulfur wherein R$^{27}$ at each occurrence is independently hydrogen, loweralkyl, cylcoalkyl, cycloalkylalkyl or arylalkyl and wherein two such heteroatoms or heterogroups are separated by at least one carbon atom.

The term "alkylsulfonyl" as used herein refers to the group having the formula, —SO$_2$—R$^{78}$, where R$^{78}$ is an alkyl group. Preferred groups R$^{78}$ are loweralkyl groups.

The term "alkylsulfonylamino" as used herein refers to the group having the formula, —SO$_2$—R$^{77}$, appended to the parent molecular moiety through an amino linkage (—NH—), where R$^{77}$ is an alkyl group. Preferred groups R$^{77}$ are loweralkyl groups.

The term "alkynyl" as used herein, refers to a straight or branched chain hydrocarbon radical containing from 2 to 15 carbon atoms and also containing at least one carbon-carbon triple bond. The term "lower alkynyl" refers to straight or branched chain alkynyl radicals containing from 2 to 6 carbon atoms. Representative examples of alkynyl groups include groups such as, for example, acetylenyl, 1-propynyl, 2-propynyl, 3-butynyl, 2-pentynyl, 1-butynyl and the like.

The term "alkynylene" as used herein, refers to a divalent group derived from a straight or branched chain hydrocarbon containing from 2 to 15 carbon atoms and also containing at least one carbon-carbon triple bond. The term "lower alkynylene" refers to a divalent group derived from a straight or branched chain alkynylene group from 2 to 6 carbon atoms. Representative examples of alkynylene groups include groups such as, for example, —C≡C—, —CH$_2$—C≡C—, —C≡—C—CH$_2$—, —CH(CH$_3$)—C≡—C—, and the like.

The term "aminoalkyl" as used herein refers to an alkyl radical to which is appended an amino (—NH$_2$) group.

The term "aryl" as used herein refers to a carbocyclic ring system having 6–10 ring atoms and one or two aromatic rings. Representative examples of aryl groups include groups such as, for example, phenyl, naphthyl, tetrahydronaphthyl, indanyl, indenyl and the like.

The aryl groups can be unsubstituted or substituted with one, two or three substituents, each independently selected from loweralkyl, halo, haloalkyl, haloalkoxy, hydroxy, oxo (=O), hydroxyalkyl, alkenyloxy, alkoxy, alkoxyalkoxy, alkoxycarbonyl, alkoxycarbonylalkyl, thioalkoxy, amino, alkylamino, alkylsulfonyl, dialkylamino, acylamino, unsubstituted aryl, unsubstituted arylalkyl, unsubstituted arylalkoxy, unsubstituted aryloxy, mercapto, cyano, nitro, carboxy, carboxaldehyde, NH$_2$C(=O)—, cycloalkyl, carboxyalkyl, alkylsulfonylamino, unsubstituted heterocyclic, unsubstituted (heterocyclic)alkyl, unsubstituted (heterocyclic)alkoxy, unsubstituted (heterocyclic)oxy and —SO$_3$H. Preferred aryl substituents are each independently selected from the group consisting of loweralkyl, halo, haloalkyl, hydroxy, hydroxyalkyl, alkenyloxy, alkoxy, alkoxyalkoxy, thioalkoxy, amino, alkylamino, dialkylamino, alkylsulfonyl, acylamino, cyano and nitro. Examples of substituted aryl include 3-chlorophenyl, 3-fluorophenyl, 4-chlorophenyl, 4-fluorophenyl, 3,4-dichlorophenyl, 3-chloro-4-fluoro-phenyl, 4-methylsulfonylphenyl, and the like.

The term "(aryl)alkenyl" refers to a lower alkenyl group having appended thereto an aryl group. Representative examples of (aryl)alkenyl groups include groups such as, for example phenylethylenyl, phenylpropenyl, and the like.

The term "(aryl)alkyl" refers to a loweralkyl group having appended thereto an aryl group. Representative examples of (aryl)alkyl groups include groups such as, for example benzyl and phenylethyl.

The term "arylalkoxy" as used herein refers to the group having the formula, —O—$R^{76}$ where $R^{76}$ is an arylalkyl group.

The term "(aryl)alkynyl" refers to an alkynylene group having appended thereto an aryl group. Representative examples of (aryl)alkynyl groups include groups such as, for example phenylacetylenyl, phenylpropynyl, and the like.

The term "aryloxy" as used herein refers to the group having the formula, —O—$R^{72}$, where $R^{72}$ is an aryl group.

The term "carbamidyl" as used herein refers to the group having the formula, —NH—C(=O)—$NH_2$.

The term "carbamoyl" as used herein refers to the group having the formula, —C(=O)—$NH_2$.

The term "carboxyalkyl" as used herein, refers to the group having the formula, —$R^{64}$—COOH, where $R^{64}$ is a lower alkylene group.

The term "cyanoalkyl" as used herein refers to an alkyl radical to which is appended a cyano group (—CN).

The term "cycloalkenyl" as used herein refers to an aliphatic ring system having 5 to 10 carbon atoms and 1 or 2 rings containing at least one double bond in the ring structure. Representative examples of cycloalkenyl groups include groups such as, for example, cyclohexene, cyclopentene, norbornene and the like.

Cycloalkenyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkenyl)alkenyl" as used herein refers to a cycloalkenyl group appended to a lower alkenyl radical. Representative examples of (cycloalkenyl)alkenyl groups include groups such as, for example, cyclohexenylethylene, cyclopentenylethylene, and the like.

The term "(cycloalkenyl)alkyl" as used herein refers to a cycloalkenyl group appended to a lower alkyl radical. Representative examples of (cycloalkenyl)alkyl groups include groups such as, for example, cyclohexenylmethyl, cyclopentenylmethyl, cyclohexenylethyl, cyclopentenylethyl, and the like.

The term "(cycloalkenyl)alkynyl" as used herein refers to a cycloalkenyl group appended to a lower alkynyl radical. Representative examples of (cycloalkenyl)alkynyl groups include groups such as, for example, cyclohexenylacetylenyl, cyclopentenylpropynyl, and the like.

The term "cycloalkyl" as used herein refers to an aliphatic ring system having 3 to 10 carbon atoms and 1 or 2 rings. Representative cycloalkyl groups include, for example, cyclopropyl, cyclobutyl, cyclopentyl, cyclohexyl, cycloheptyl, norbornene, bicyclo[2.2.2]octane and the like.

Cycloalkyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkyl)alkyl" as used herein refers to a cycloalkyl group appended to a loweralkyl radical. Representative examples of (cycloalkyl)alkyl groups include groups such as, for example, cyclohexylmethyl, cyclopentylmethyl, cyclohexylethyl, cyclopentylethyl, and the like.

The term "(cycloalkyl)alkenyl" as used herein refers to a cycloalkyl group appended to a lower alkenyl radical. Representative examples of (cycloalkyl)alkenyl groups include groups such as, for example, cyclohexylethylene, cyclopentylethylene, and the like.

The term "(cycloalkyl)alkynyl" as used herein refers to a cycloalkyl group appended to a lower alkynyl radical. Representative examples of (cycloalkyl)alkynyl groups include groups such as, for example, cyclohexylacetylenyl, cyclopentylpropynyl, and the like.

The term "dialkylaminoll as used herein, refers to groups having the formula —$N(R^{90})_2$ wherein each $R^{90}$ is independently a lower alkyl group. Representative examples of dialkylamino include dimethylamino, diethylamino, N-methyl-N-isopropylamino and the like.

The term "dialkylaminoalkyl" as used herein refers to a dialkylamino group appended to an alkyl radical. Representative examples of dialkylaminoalkyl include dimethylaminomethyl, dimethylaminoethyl, N-methyl-N-ethylaminoethyl and the like.

The term "dialkylaminocarbonylalkyl" as used herein refers to a —C(O)—$N(R^{90})_2$ group (wherein each $R^{90}$ is independently a lower alkyl group) appended to an alkyl radical. Representative examples of dialkylaminocarbonylalkyl include dimethylaminocarbonylmethyl, diethylaminocarbonylmethyl, N-methyl-N-ethylaminocarbonylethyl and the like.

The term "dialkylaminocarbonyloxyalkyl" as used herein refers to a —O—C(O)—$N(R^{90})_2$ group (wherein each $R^{90}$ is independently a lower alkyl group) appended to an alkyl radical. Representative examples of dialkylaminocarbonyloxyalkyl include dimethylaminocarbonyloxymethyl, diethylaminocarbonyloxymethyl, N-methyl-N-ethylaminocarbonyloxyethyl and the like.

The term "enantiomerically enriched" as used herein refers to a compound which comprises unequal amounts of the enantiomers of an enantiomeric pair. In other words, an enantiomerically enriched compound comprises more than 50% of one enantiomer of an enantiomeric pair and less than 50% of the other enantiomer of the enantiomeric pair. Preferably, a compound that is enantiomerically enriched comprises predominantly one enantiomer of an enantiomeric pair. Preferably, an enantiomerically enriched compound comprises greater than 80% of one enantiomer of an enantiomeric pair and less than 20% of the other enantiomer of the enantiomeric pair. More preferably, an enantiomerically enriched compound comprises greater than 90% of one enantiomer of an enantiomeric pair and less than 10% of the other enantiomer of the enantiomeric pair. Even more preferably, an enantiomerically enriched compound comprises greater than 95% of one enantiomer of an enantiomeric pair and less than 5% of the other enantiomer of the enantiomeric pair. Even more highly preferably, an enantiomerically enriched compound comprises greater than 97% of one enantiomer of an enantiomeric pair and less than 3% of the other enantiomer of the enantiomeric pair. Yet even more highly preferably, an enantiomerically enriched compound comprises greater than 98% of one enantiomer of an enantiomeric pair and less than 2% of the other enantiomer of the enantiomeric pair. Most preferably, an enantiomerically enriched compound comprises greater than 99% of one enantiomer of an enantiomeric pair and less than 1% of the other enantiomer of the enantiomeric pair.

The term "halo" or "halide" as used herein refers to F, Cl, Br or I.

The term "haloalkenyl" as used herein refers to a loweralkenyl group in which one or more hydrogen atoms is replaced with a halogen. Examples of haloalkenyl groups include 2-fluoroethylene, 1-chloroethylene, 1,2-difluoroethylene, trifluoroethylene, 1,1,1-trifluoro-2-propylene and the like.

The term "haloalkoxy" as used herein refers to the group having the formula, —OR$^{69}$, where R$^{69}$ is a haloalkyl group as defined herein. Examples of haloalkoxy include chloromethoxy, fluoromethoxy, dichloromethoxy, trifluoromethoxy and the like.

The term "haloalkyl" as used herein, refers to a loweralkyl group in which one or more hydrogen atoms has been replaced with a halogen including, but not limited to, trifluoromethyl, trichloromethyl, difluoromethyl, dichloromethyl, fluoromethyl, chloromethyl, chloroethyl, 2,2-dichloroethyl, 2,2,2-trichloroethyl, pentafluoroethyl and the like.

The term "heterocyclic ring" or "heterocyclic" or "heterocycle" as used herein, refers to any 3- or 4-membered ring containing a heteroatom selected from oxygen, nitrogen and sulfur; or a 5-, 6- or 7-membered ring containing one, two, three, or four nitrogen atoms; one oxygen atom; one sulfur atom; one nitrogen atom and one sulfur atom; two nitrogen atoms and one sulfur atom; one nitrogen atom and one oxygen atom; two nitrogen atoms and one oxygen atom; two oxygen atoms in non-adjacent positions; one oxygen atom and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring, such as, for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like.

Heterocyclic groups include, but are not limited to groups such as, for example, aziridinyl, azetidinyl, epoxide, oxetanyl, thietanyl, pyrrolyl, pyrrolinyl, pyrrolidinyl, pyrazolyl, pyrazolinyl, pyrazolidinyl, imidazolyl, imidazolinyl, imidazolidinyl, pyridyl, tetrahydropyridyl, piperidinyl, homopiperidinyl, pyrazinyl, piperazinyl, pyrimidinyl, pyridazinyl, oxazolyl, oxazolinyl, oxazolidinyl, isoxazolyl, isoxazolidinyl, morpholinyl, thiomorpholinyl, thiazolyl, thiazolinyl, thiazolidinyl, isothiazolyl, isothiazolidinyl, indolyl, quinolinyl, isoquinolinyl, benzimidazolyl, benzothiazolyl, benzoxazolyl, oxetanyl, dihydrofuranyl, tetrahydrofuranyl, dihydropyranyl, tetrahydropyranyl, thienyl, dihydrothienyl, tetrahydrothienyl, triazolyl, triazolinyl, tetrazolyl, tetrazolinyl, isoxazolyl, 1,2,3-oxadiazolyl, 1,2,4-oxadiazolyl, 1,3,4-oxadiazolyl, 1,2,5-oxadiazolyl, oxadiazolinyl, , 1,2,3-thiadiazolyl, 1,2,4-thiadiazolyl, 1,3,4-thiadiazolyl, 1,2,5-thiadiazolyl, thiadiazolinyl,1,3-dithiolinyl, 1,2-dithiolyl, 1,3-dithiolyl, 1,3-dioxolinyl, didehydrodioxolanyl, 1,3-oxathiolinyl, oxathiolyl, pyrimidyl, benzothienyl and the like. Heterocyclic groups also include compounds of the formula

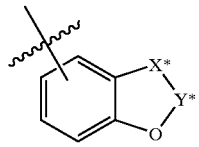

where X* is —CH$_2$ or —O— and Y* is —C(O)— or [—C(R$^{92}$)$_2$—]$_v$ where R$^{92}$ is hydrogen or C$_1$–C$_4$ alkyl where v is 1, 2, or 3 such as 1,3-benzodioxolyl, 1,4-benzodioxanyl and the like. Heterocyclic groups also include bicyclic rings such as quinuclidinyl and the like.

Heterocyclic groups can be unsubstituted or substituted with from one to three substituents, each independently selected from loweralkyl, hydroxy, alkoxy, thioalkoxy, amino, alkylamino, dialkylamino and halogen. In addition, nitrogen containing heterocyclic rings can be N-protected.

The term "(heterocyclic)alkenyl" as used herein refers to a heterocyclic group appended to a lower alkenyl radical including, but not limited to, pyrrolidinylethenyl, morpholinylethenyl and the like.

The term "(heterocyclic)alkoxy" as used herein refers to the group having the formula, —OR$^{68}$, where R$^{68}$ is a (heterocyclic)alkyl group.

The term "(heterocyclic)alkyl" as used herein refers to a heterocyclic group appended to a loweralkyl radical including, but not limited to, pyrrolidinylmethyl, morpholinylmethyl and the like.

The term "(heterocyclic)alkynyl" as used herein refers to a heterocyclic group appended to a lower alkynyl radical including, but not limited to, pyrrolidinylacetylenyl, morpholinylpropynyl and the like.

The term "(heterocyclic)carbonylalkyl" as used herein refers to a heterocyclic group appended to an alkyl radical via a carbonyl group. Representative examples of (heterocyclic)carbonylalkyl include pyridylcarbonylmethyl, morpholinocarbonylethyl, piperazinylcarbonylmethyl and the like.

The term "(heterocyclic)carbonyloxyalkyl" as used herein refers to a heterocyclic group appended to an alkyl radical via a carbonyloxy group (i.e., —C(O)—O—). Representative examples of (heterocyclic)carbonylalkyl include pyridylcarbonylmethyl, morpholinocarbonylethyl, piperazinylcarbonylmethyl and the like.

The term "(heterocyclic)oxy" as used herein refers to a heterocyclic group appended to the parent molecular moiety through an oxygen atom (—O—).

The term "hydroxy protecting group," hydroxyl protecting group,"or "—OH protecting group," as used herein, refers to groups used to hydroxy groups against undesirable reactions during synthetic procedures. Commonly used hydroxy protecting groups are disclosed in T. H. Greene and P. G. M. Wuts, *Protective Groups in Organic Synthesis,* 2nd edition, John Wiley & Sons, New York (1991) which is incorporated by reference herein. Such hydroxy protecting groups include:

methyl ether;

substituted methyl ethers, including, but not limited to, methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, t-butoxymethyl, 2-methoxyethoxymethyl, 2,2,2-trichloroethoxymethyl, 2-(trimethylsilyl)ethoxymethyl, tetrahydropyranyl, tetrahydrothiopyranyl, tetrahydrofuranyl, tetrahydrothiofuranyl ether and the like;

substituted ethyl ethers, including, but not limited to, 1-ethoxyethyl, 1-methyl-1-methoxyethyl, 1-methyl-1-benzyloxyethyl, 2,2,2-trichloroethyl, trimethylsilylethyl, t-butyl ether and the like;

benzyl ether;

substituted benzyl ethers, including, but not limited to, p-methoxybenzyl, 3,4-dimethoxybenzyl, o-nitorbenzyl, p-halobenzyl, p-cyanobenzyl, diphenylmethyl, triphenylmethyl ether and the like;

silyl ethers, including, but not limited to, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, triphenylsilyl, diphenylmethylsilyl ether and the like;

esters, including, but not limited to, formate, acetate, chloroacetate, dichloroacetate, trichloroacetate, trifluoroacetate, methoxyacetate, phenoxyacetate, pivaloate, benzoate ester and the like; and the like.

Preferred hydroxy protecting groups include substituted methyl ethers, benzyl ether, substituted benzyl ethers, silyl ethers and esters.

The term "hydroxyalkyl" as used herein refers to the group having the formula, —$R^{65}$—OH, where $R^{65}$ is an alkylene group The term "leaving group" as used herein refers to a group which is easily displaced from the compound by a nucleophile. Examples of leaving groups include a halide (for example, Cl, Br or I) or a sulfonate (for example, mesylate, tosylate, triflate and the like) and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha, alpha-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "thioalkoxy" as used herein refers to groups having the formula —$SR^{98}$ wherein $R^{98}$ is an alkyl group. Preferred groups $R^{98}$ are lower alkyl groups.

The term "thio-substituted alkyl" as used herein refers to an alkyl radical to which is appended a thiol group (—SH).

As used herein, the terms "S" and "R" configuration are as defined by the IUPAC 1974 Recommendations for Section E, Fundamental Stereochemistry, Pure Appl. Chem. (1976) 45, 13–30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of Formula Ia or Ib are meant to be included in this invention.

When any variable (for example $R^1$, $R^2$, $R^3$, m, n, etc.) occurs more than one time in any substituent or in the compound of Formula Ia or Ib or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

This invention is intended to encompass compounds having Formula Ia or Ib when prepared by synthetic processes or by metabolic processes. Preparation of the compounds of the invention by metabolic processes include those occurring in the human or animal body (in vivo) or processes occurring in vitro.

Compounds of the invention can be prepared according to the methods described in the Schemes as shown below. Throughout the Schemes, methods will be illustrated for obtaining compounds of the invention having the preferred relative stereochemistry. It will be understood by those skilled in the art that compounds of the invention having other relative stereochemistry can be prepared by methods analogous to those disclosed in the schemes or by other methods generally known in the art.

Synthetic Methods

The compounds and processes of the invention will be better understood in connection with the following synthetic Schemes which illustrate methods by which the compounds of the invention can be prepared. The compounds of the invention can be prepared by a variety of procedures. Representative procedures are shown in Schemes 1–56.

It will be readily apparent that other compounds of the invention can by synthesized by the substitution of appropriate starting materials and reagents in the syntheses shown below. It will also be apparent that protection and deprotection steps, as well as the order of the steps themselves, can be carried out in varying order, to successfully complete the syntheses of compounds of the invention. Commonly used protecting groups are disclosed in Greene, (op. Cit).

The other compounds of the invention can be readily prepared from the compounds described herein using techniques known in the chemical literature. The methods required are known and can be readily practiced by those having ordinary skill in the art.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

Starting materials and reagents are available commercially or can be prepared synthetically by known methods such as those disclosed in Larock, "Comprehensive Organic Transformation. A Guide to Functional Group Preparations," VCH Publishers, New York (1989).

All of the reactions discussed in the Schemes are run in solvents in which the starting materials and products are not reactive, unless otherwise specified and those in which the starting materials are at least partially soluble. The appropriate solvent for each reaction will be apparent to one skilled in the art. For example, possible solvents, which can be used include THF, DCM, MeCN, DMF, EtOAc, hexanes, toluene, benzene, DMSO, MeOH, EtOH, i-PrOH, water, dioxane, anisole, pyridine, aniline, TEA, NMP, HMPA, glyme, diglyme, xylene, DME, acetone, cyclohexane, glycerol, 1,2-dichloroethane, tertiary-butyl methyl ether, ethyl ether, methyl ether, PhOPh, chloroform, carbon tetrachloride, dioxane, morpholine, 1,1,1-trichloroethane, trifluoroacetic acid, AcOH, hydrochloric acid, sulfuric acid, perchloric acid, nitric acid and mixtures thereof.

The term "hydroxy-protecting group," as used herein, refers to selectively removable groups which protect hydroxyl groups against undesirable reactions during synthetic procedures. The use of hydroxy-protecting groups is well-known in the art and is discussed in T. H. Greene and P. G. M. Wuts, "Protective Groups in Organic Synthesis," 2nd edition, John Wiley & Sons, New York (1991), pp 10–86. Examples of hydroxy-protecting groups include methylthiomethyl, tertiary-butyldimethylsilyl, tertiary-butyldiphenylsilyl, acetyl, benzoyl, and the like.

Numerous asymmetric centers exist in the compounds of the invention. The invention contemplates the various stereoisomers and mixtures thereof. Individual stereoisomers of compounds of the invention can be made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the art.

Abbreviations

Abbreviations used in the descriptions of the Schemes and the examples that follow are: THF for tetrahydrofuran; AcOH for acetic acid; Ac for acetate; MeCN for acetonitrile; MeOH for methanol; TMS for trimethylsilyl; TES for triethylsilyl; TFA for trifluoroacetic acid; TBDMS for tertiary-butyldimethylsilyl; TMSCl for trimethylsilyl chloride; TMSBr for trimethylsilyl bromide; $TMSN_3$ for trimethylsilyl azide; $BF_3.OEt_2$ for boron trifluoride diethyl etherate; DBU for 1,8-diazabicyclo[5.4.0]undec-7-ene; TEA for triethylamine; TMSOTf for trimethylsilyl triflate; DMF for N,N-dimethylformamide; Ph for phenyl; DCM for dichloromethane; DME for dimethoxyethane; DMSO for dimethyl sulfoxide; Et for ethyl; i-Pr for isopropyl; TBME for tertiary-butyl methyl ether; PBu$_3$ for tributylphosphine; HMPA for hexamethylphosphoramide; Pb(OAc)$_4$ for lead (IV)acetate; NMP for N-methylpyrrolidine; AIBN for 2,2'-azobisisobutyronitrile; MCPBA for meta-chloroperbenzoic acid; NMO for N-methylmorpholine N-oxide; TBAF for tetrabutylammonium fluoride; NaOMe for sodium methoxide; NaOEt for sodium ethoxide; TsOH for paratoluenesulfonic acid; PPh$_3$ for triphenylphosphine; PEt$_3$ for triethylphosphine; and P(OEt)$_3$ for triethyl phosphite; nosyl for para-nitrophenylsulfonyl; DMAP for N,N-dimethylaminopyridine; acac for acetylacetonate, dba for dibenzylideneacetone; PSI for pounds per square inch; PhoPh for diphenylether; brosyl for para-bromophenylsulfonyl; PCC for pyridinium chlorochromate; dppf for 1,1'-bis(diphenylphosphino)ferrocene.

N-chlorosuccinimide, Br$_2$, and Cl$_2$. Specific examples of free radical initiators include AIBN and di-tertiary-butyl peroxide in the presence of ultraviolet light or heat. Specific examples of solvents include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, (1A) is treated with AIBN and N-bromosuccinimide in refluxing benzene for about four hours.

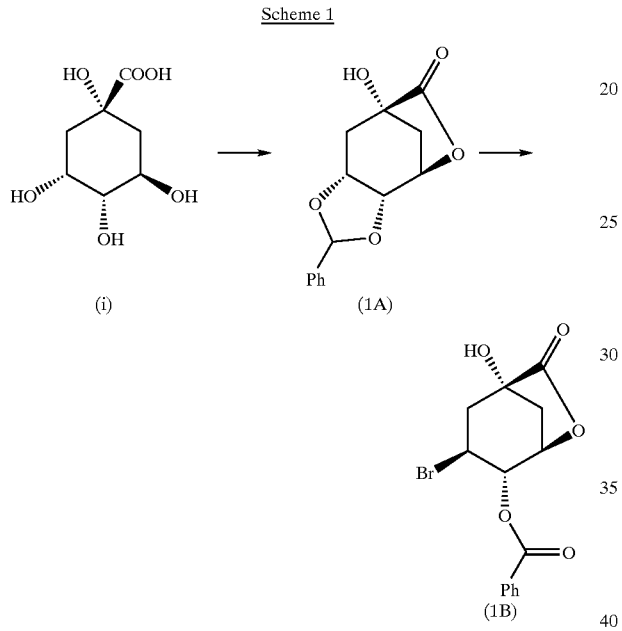

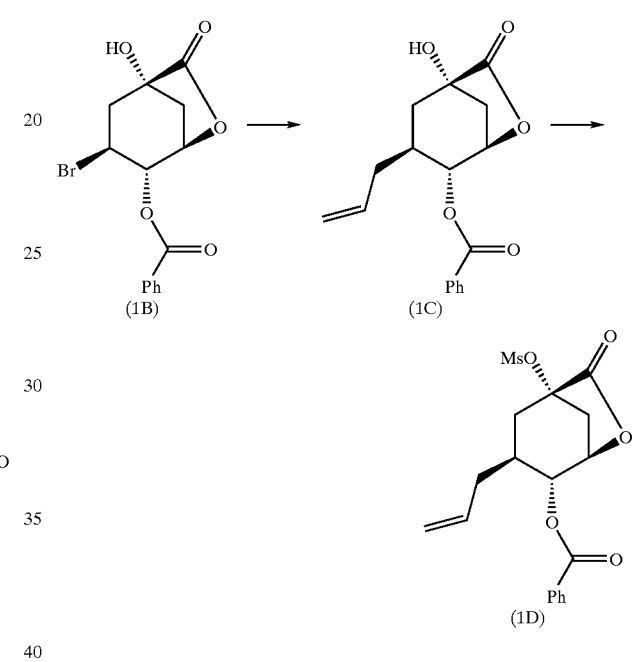

As shown in Scheme 1, the conversion of (i) to (1A) can be accomplished by treating the former with a protecting group precursor, and an additive in a solvent. Specific examples of protecting group precursors include acetaldehyde, acetone, benzaldehyde, para-methoxybenzaldehyde, 3-pentanone, cyclohexanone, and 2,2-dimethoxypropane. Specific examples of additives include acids and bases. More preferred are the following acids: triflic acid, TFA, TsOH and hydrogen chloride. Since water is generated during the course of the reaction, the reaction can be dried by azeotropic removal of the water. An appropriate solvent for this conversion, therefore, is one which azeotropes with water. Specific examples of solvents which azeotrope with water include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a particularly preferred embodiment, a solution of (i), benzaldehyde, and TsOH in toluene is refluxed for about 10 hours. The water is removed azeotropically.

Conversion of (1A) to (1B) can be accomplished by treating the former with a free radical precursor and a free radical initiator in a solvent. Specific examples of free radical precursors include N-bromosuccinimide, As shown in Scheme 2, the conversion of (1B) to (1C) can be accomplished by treating the former with an organostannane and a free radical initiator in a solvent. Specific examples of organostannanes include 2-(tributylstannyl)furan, tributyltin hydride, allyltributyltin, vinyltributyltin, and 2-(tributylstannyl)thiophene. Specific examples of free radical initiators include AIBN and di-tertiary-butyl peroxide in the presence of ultraviolet light or heat. Specific examples of solvents include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, (1B), allyltributyltin and AIBN in benzene are refluxed for about 10 hours.

The conversion of (1C) to (1D) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as PPh$_3$, and PBu$_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU and diisopropylethylamine. Specific examples of solvents include DCM, chloroform, THF, TBME and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (1C) in DCM at about 0° C., is treated with methanesulfonyl chloride and TEA for about two hours.

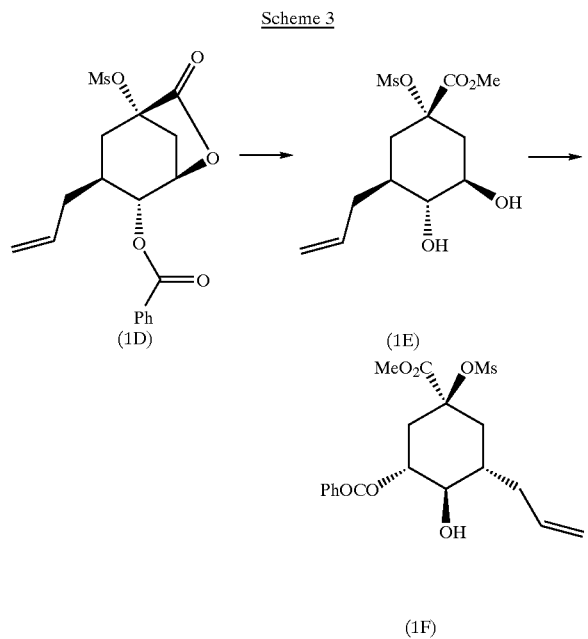

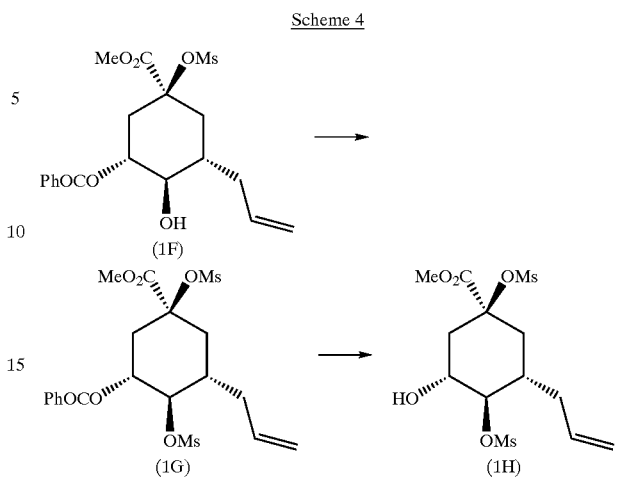

As shown in Scheme 3, the conversion of (1D) to (1E) can be accomplished by treating the former with a base and an alcohol. Specific examples of bases include K₂CO₃, NaOMe, NaOEt, NaOH, and KOH. Specific examples of alcohols include methanol, ethanol, and isopropanol. Although the reaction generally proceeds at room temperature, it can be run at lower or elevated temperatures, as needed. The reaction time is generally about 30 minutes to about 12 hours and can be selected depending on the reaction temperature. In a preferred embodiment, (1D) in methanol at room temperature is treated with potassium carbonate for about 30 minutes.

The conversion of (1E) to (1F) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (1E) in DCM at about 0° C. is treated with benzoyl chloride and pyridine for about 5 hours.

As shown in Scheme 4, the conversion of (1F) to (1G) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as PPh₃, and PBu₃, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU and diisopropylethylamine. Specific examples of solvents include DCM, chloroform, THF, TBME and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (1F) in DCM at about 0° C., is treated with methanesulfonyl chloride and TEA for about 10 hours.

The conversion of (1G) to (1H) can be accomplished by treating the former with a base, and an alcohol. Specific examples of bases include K₂CO₃, NaOMe, NaOEt, NaOH, and KOH. Specific examples of alcohols include methanol, ethanol, and isopropanol. Although the reaction generally proceeds at room temperature, it can be run at lower or elevated temperatures, as needed. The reaction time is generally about 15 minutes to about 12 hours and can be selected depending on the reaction temperature. In a preferred embodiment, (1G) in methanol at room temperature is treated with potassium carbonate for about 30 minutes.

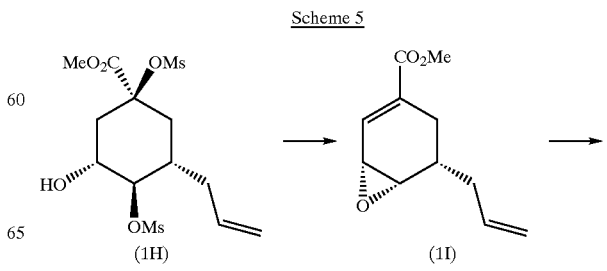

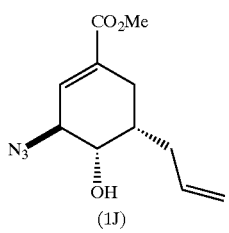

(1J)

As shown in Scheme 5, the conversion of (1H) to (1I) can be accomplished by treating the former with a base in a solvent. Specific examples of bases include potassium tertiary-butoxide, diisopropylethylamine, and DBU. Specific examples of solvents include THF, chloroform, TBME, and benzene. The reaction generally proceeds at reflux, the temperature of which can be determined by using a solvent of known boiling point at atmospheric pressure. The reaction time is generally about 30 minutes to about 12 hours and can be selected depending on the reaction temperature. In a preferred embodiment, (1H) in THF is treated with DBU and refluxed for about 6 hours.

The conversion of (1I) to (1J) can be accomplished by treating the former with a nucleophile and an additive. Specific examples of nucleophiles include $NaN_3$, $TMSN_3$, TMSCl, TMSBr, carbanions, thioacetate, and cyanide. More preferred are the following nucleophiles: $NaN_3$ and $TMSN_3$. Specific examples of additives include acids and bases. More preferred are the following acids: $NH_4Cl$, $(NH_4)_2SO_4$, and AcOH. Specific examples of solvents include MeOH, EtOH, i-PrOH, NMP, water, and mixtures thereof. Although the reaction generally proceeds at reflux, the temperature of which can be determined by using a solvent of known boiling point at atmospheric pressure, it can be run at lower temperatures as needed. The reaction time is generally about 30 minutes to about 24 hours and can be selected depending on the reaction temperature. In a particularly preferred embodiment, (1I), $NaN_3$ and $NH_4Cl$ in methanol-water is refluxed for about 5 hours.

Scheme 6

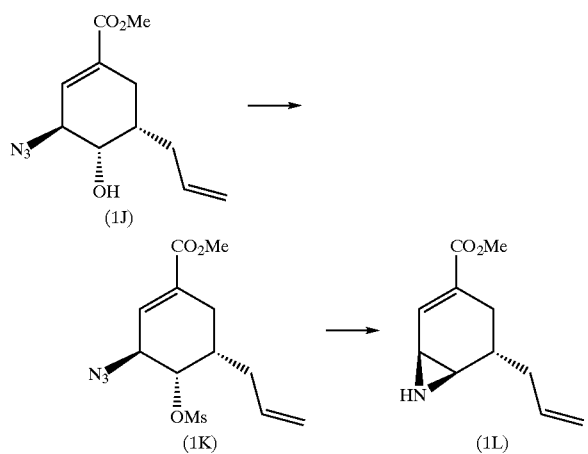

As shown in Scheme 6, the conversion of (1J) to (1K) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (1J) in DCM at about 0° C., is treated with methanesulfonyl chloride and TEA for about two hours.

The conversion of (1K) to (1L) can be accomplished by treating the former with a reducing agent in a solvent. Specific examples of reducing agents include phosphines followed by water and base, and $H_2S$ and pyridine. More preferred are the following phosphines: $PPh_3$ and $PEt_3$. Specific examples of bases include TEA, $NH_4OH$, and NaOH. Specific examples of solvents include THF, MeOH, TBME and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (1K) in THF at room temperature is treated with $PPh_3$ for about two hours, followed by water and TEA for about 10 hours.

Scheme 7

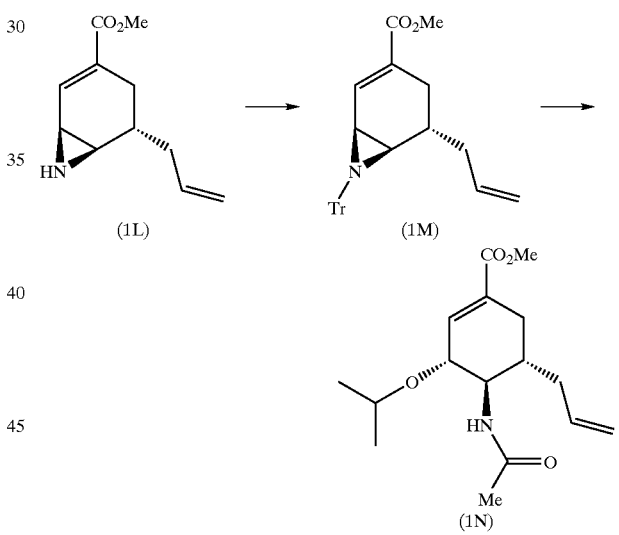

As shown in Scheme 7, the conversion of (1L) to (1M) can be accomplished by treating the former with a protecting group and a base in a solvent. Specific examples of protecting groups include trityl, nosyl and brosyl. Specific examples of base include pyridine, TEA and 2,6-lutidine. Specific examples of solvents include DCM, THF, chloroform and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (1L) in DCM at about 0° C. is treated with trityl chloride and TEA for about two hours.

The conversion of (1M) to (1N) can be accomplished by treating the former with a Lewis acid and an alcohol in a solvent to afford an intermediate which can then be treated with an acylating agent and a base. Specific examples of Lewis acids include $ZnCl_2$, $TiCl_4$, $BF_3.OEt_2$, and $SnCl_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (1M) in isopropanol is treated with $BF_3.OEt_2$ and heated to about 75° C. for about two hours.

The conversion of the intermediate compound to (1N) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (1E) in pyridine at room temperature is treated with acetic anhydride and pyridine for about 12 hours.

Scheme 8

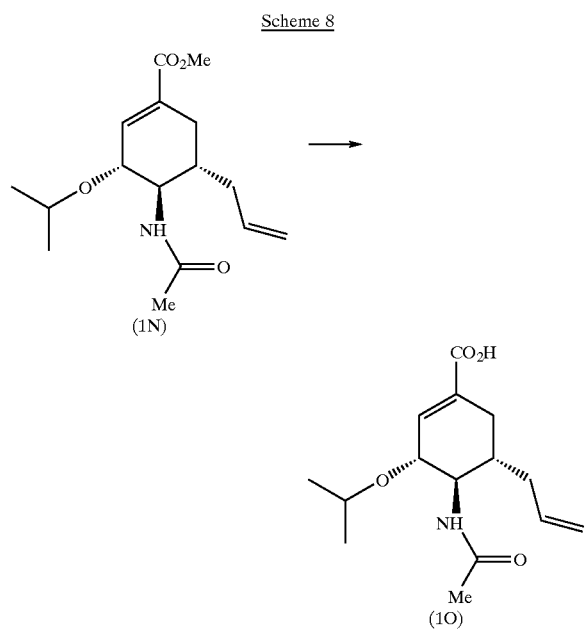

As shown in Scheme 8, the conversion of (1N) to (1O) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (1N) in THF at room temperature is treated with aqueous LiOH for about 10 hours.

Scheme 9

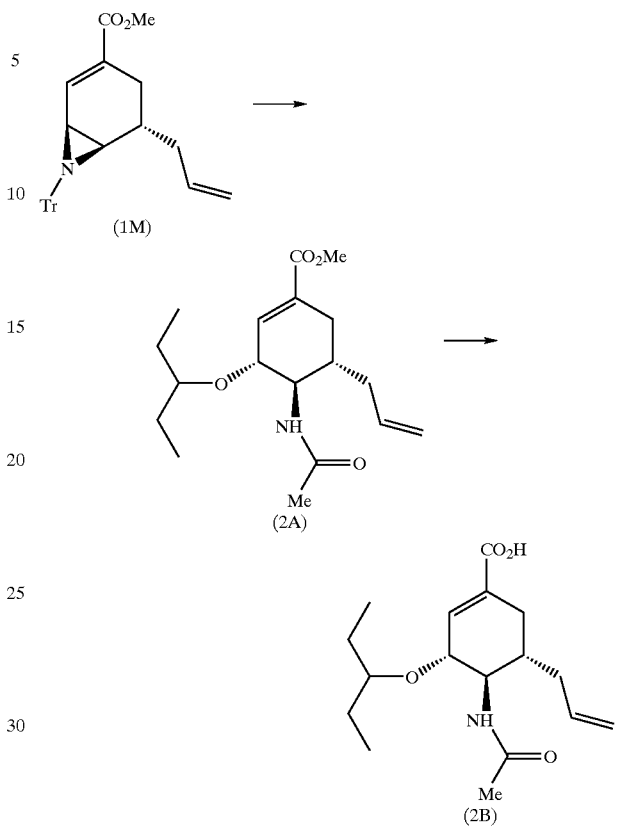

As shown in Scheme 9, the conversion of (1M) to (2A) can be accomplished by treating the former with a Lewis acid and an alcohol in a solvent to afford an intermediate which can then be treated with an acylating agent and a base. Specific examples of Lewis acids include $ZnCl_2$, $TiCl_4$, $BF_3.OEt_2$, and $SnCl_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM, and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (1M) in 3-pentanol is treated with $BF_3.OEt_2$ and heated to about 75° C. for about two hours.

The conversion of the intermediate compound to (2A) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (1E) in pyridine at room temperature is treated with acetic anhydride and pyridine for about 10 hours.

The conversion of (2A) to (2B) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (2A) in THF at room temperature is treated with aqueous LiOH for about 10 hours.

bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (3A) in THF at room temperature is treated with aqueous LiOH for about 10 hours.

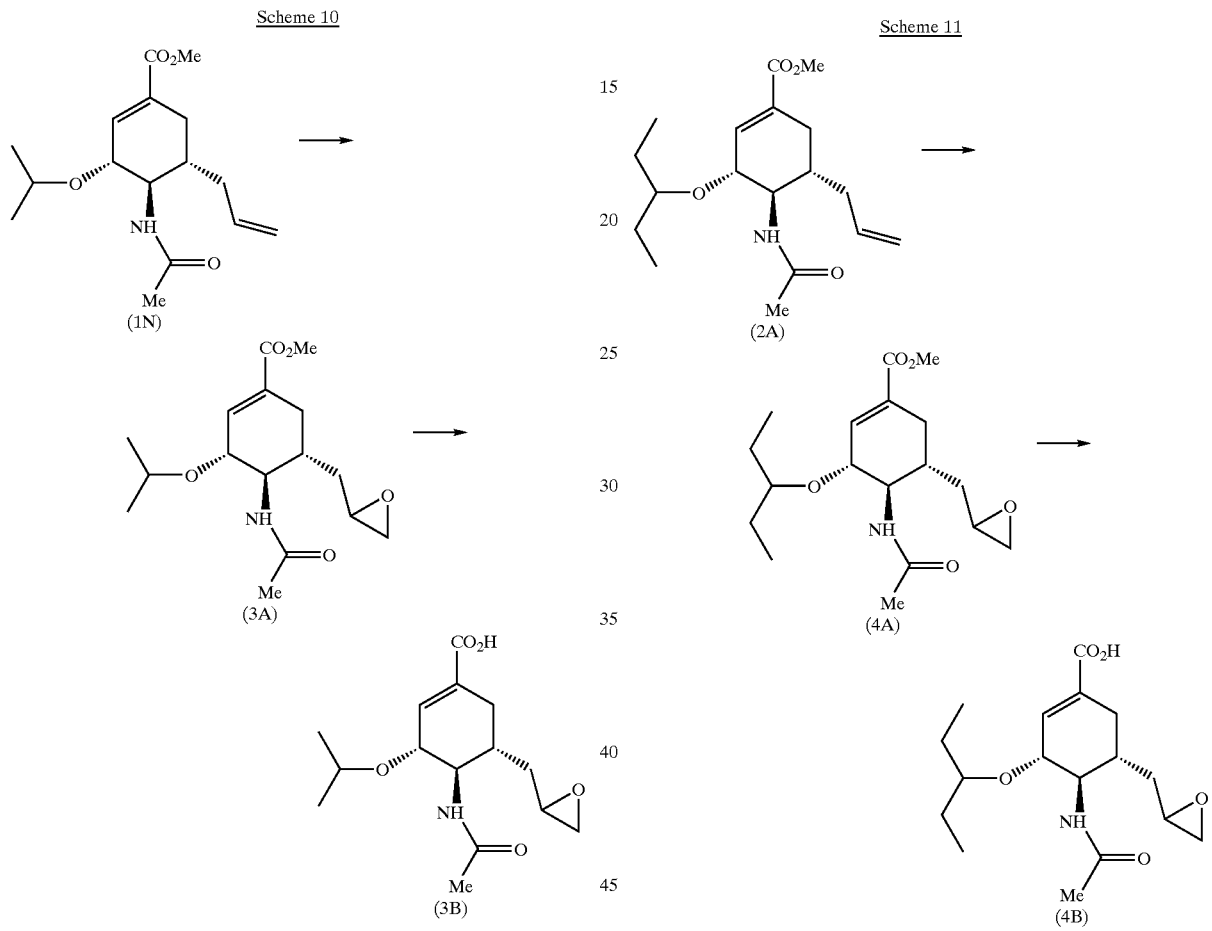

As shown in Scheme 10, the conversion of (1N) to (3A) can be accomplished by treating the former with an epoxidizing reagent in a solvent. Specific examples of epoxidizing reagents include peracids, dioxirane, hydrogen peroxide and bases such as NaOH, KOH, and LiOH, and VO(acac)$_2$ and tertiary-butylperoxide. More preferred are the following peracids: MCPBA, peracetic acid, and trifluoroperacetic acid. Specific examples of solvents include DCM, chloroform, cyclohexane, and hexanes.

Although the reaction generally proceeds at room temperature, it can be run at lower or elevated temperatures, as needed. The reaction time is generally about 30 minutes to about 24 hours and can be selected depending on the reaction temperature. In a particularly preferred embodiment, (1N) in room temperature DCM is treated with MCPBA for about 16 hours.

The conversion of (3A) to (3B) can be accomplished by treating the former with a hydrolyzing agent in a solvent. Specific examples of hydrolyzing agents include acids and As shown in Scheme 11, the conversion of (2A) to (4A) can be accomplished by treating the former with an epoxidizing reagent in a solvent. Specific examples of epoxidizing reagents include peracids, dioxirane, hydrogen peroxide and bases such as NaOH, KOH, and LiOH, and VO(acac)$_2$ and tertiary-butylperoxide. More preferred are the following peracids: MCPBA, peracetic acid, and trifluoroperacetic acid. Specific examples of solvents include DCM, chloroform, cyclohexane, and hexanes. Although the reaction generally proceeds at room temperature, it can be run at lower or elevated temperatures, as needed. The reaction time is generally about 30 minutes to about 24 hours and can be selected depending on the reaction temperature. In a particularly preferred embodiment, (2A) in room temperature DCM is treated with MCPBA for about 16 hours.

The conversion of (4A) to (4B) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (4A) in THF at room temperature is treated with aqueous LIOH for about 10 hours.

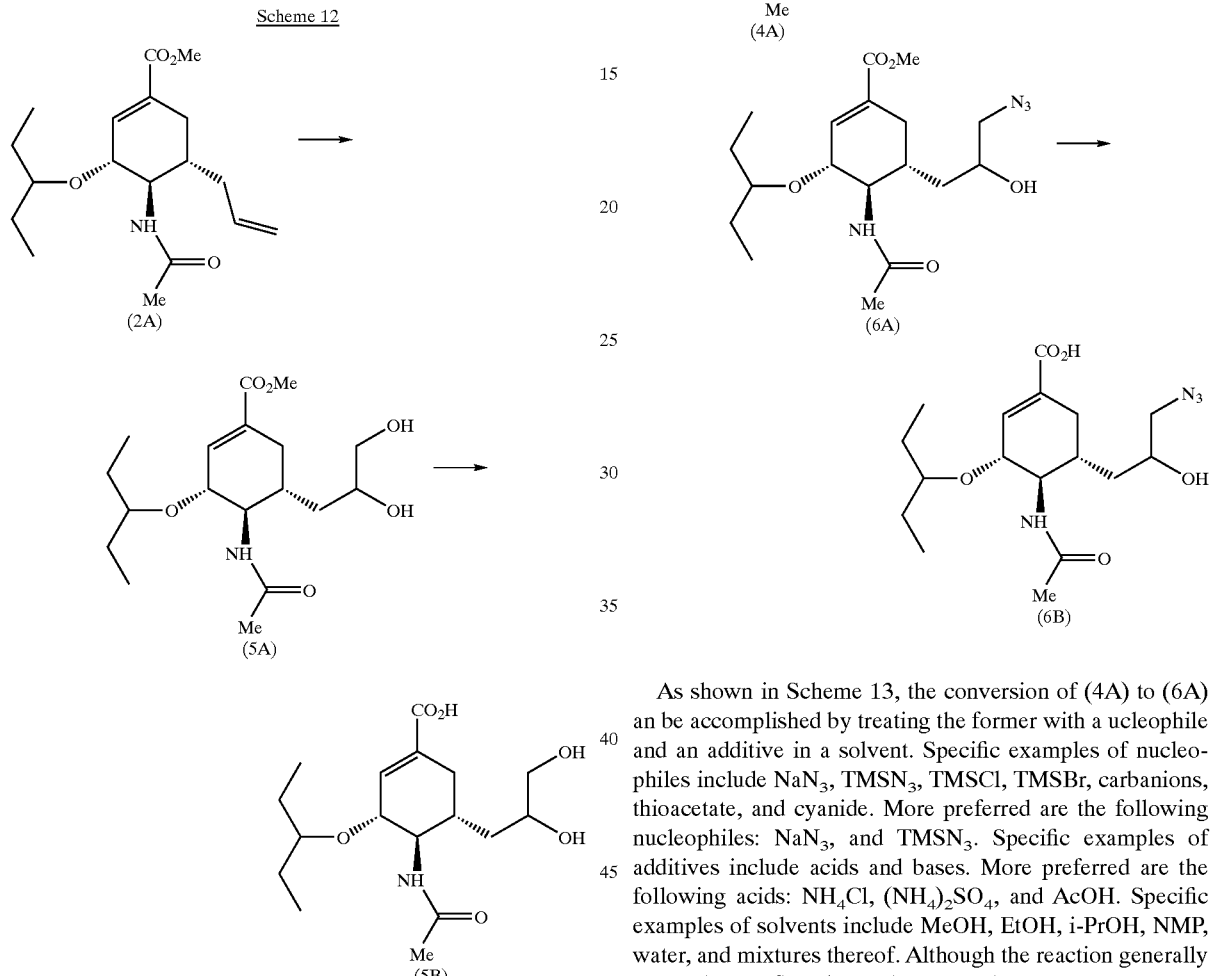

As shown in Scheme 12, the conversion of (2A) to (5A) can be accomplished by treating the former with an oxidant and bulk oxidant in a solvent. Specific examples of oxidant and bulk oxidants include the following: $OsO_4$ and NMO, and $KMnO_4$ with a base such as LiOH, NaOH, and KOH. Specific examples of solvents include toluene, benzene, xylene, acetone, tertiary-butyl alcohol, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (2A) in room temperature acetone is treated with water, NMO and $OsO_4$ in toluene for about 3 hours.

As shown in Scheme 13, the conversion of (4A) to (6A) an be accomplished by treating the former with a ucleophile and an additive in a solvent. Specific examples of nucleophiles include $NaN_3$, $TMSN_3$, TMSCl, TMSBr, carbanions, thioacetate, and cyanide. More preferred are the following nucleophiles: $NaN_3$, and $TMSN_3$. Specific examples of additives include acids and bases. More preferred are the following acids: $NH_4Cl$, $(NH_4)_2SO_4$, and AcOH. Specific examples of solvents include MeOH, EtOH, i-PrOH, NMP, water, and mixtures thereof. Although the reaction generally proceeds at reflux, it can be run at lower temperatures as needed. The reaction time is generally about 30 minutes to about 24 hours and can be selected depending on the reaction temperature. In a particularly preferred embodiment, (6A) in a methanol-water mixture is treated with $NaN_3$ and $NH_4Cl$ and refluxed for about 5 hours.

The conversion of (6A) to (6B) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (6A) in THF at room temperature is treated with aqueous LiOH for about 10 hours.

Scheme 14

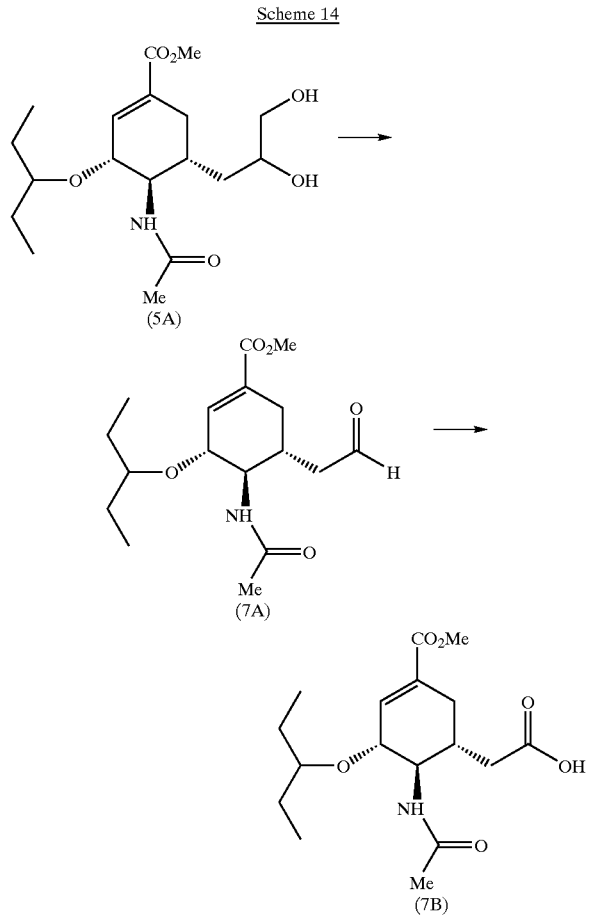

Scheme 15

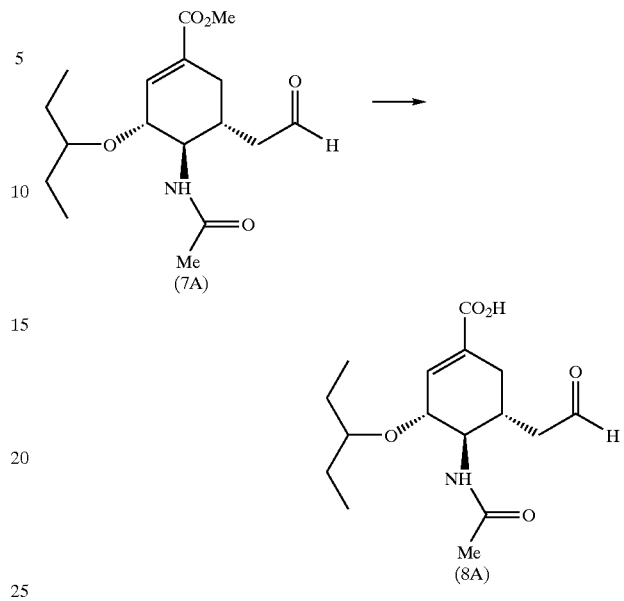

As shown in Scheme 14, the conversion of (5A) to (7A) can be accomplished by treating the former with an oxidizing agent in a solvent. Specific examples of oxidizing agents include $NaIO_4$, $HIO_4$, and $Pb(OAc)_4$. Specific examples of solvents include THF, methanol, ethanol, isopropanol, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (5A) in methanol at room temperature is treated with $NaIO_4$ in water for about three hours.

The conversion of (7A) to (7B) can be accomplished by treating the former with an oxidizing agent and an additive in a solvent. Specific examples of oxidizing agents include sodium chlorite in acidic buffer, $KMnO_4$, $H_2CrO_4$, AgO and $Na_2Cr_2O_7$. A specific example of an additive is 2-methyl-2-butene. Specific examples of solvents include THF, DCM, tertiary-butyl alcohol, methanol, ethanol, and isopropanol. Although the reaction generally proceeds at room temperature, it can be run at lower or elevated temperatures, as needed. The reaction time is generally about 30 minutes to about 24 hours and can be selected depending on the reaction temperature. In a preferred embodiment, (7A) in tertiary-butyl alcohol at room temperature is treated with sodium chlorite in $KH_2PO_4$ buffer and 2-methyl-2-butene for about 16 hours.

As shown in Scheme 15, the conversion of (7A) to (8A) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (6A) in THF at room temperature is treated with aqueous LiOH for about 12 hours.

Scheme 16

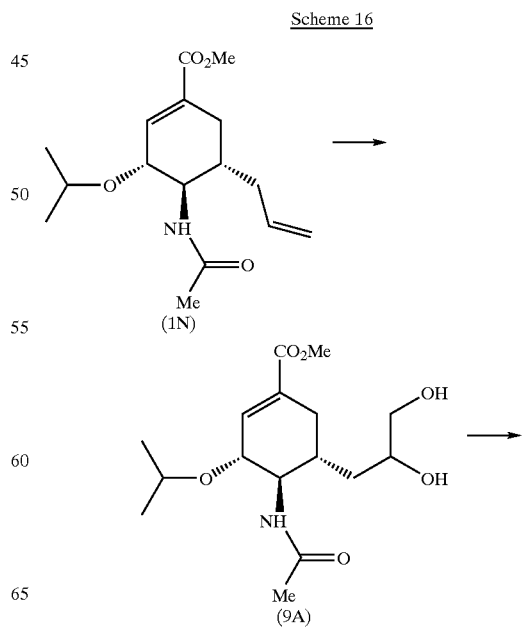

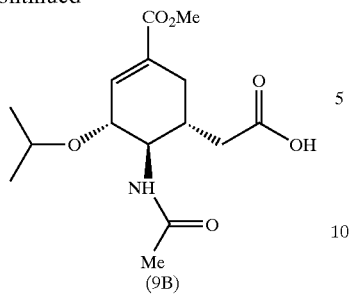

(9B)

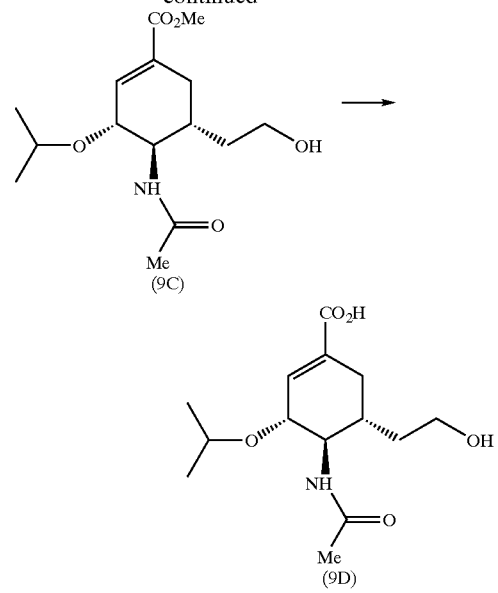

(9C)

As shown in Scheme 16, the conversion of (1N) to (9A) can be accomplished by treating the former with an oxidant in a solvent. Specific examples of oxidants include: $OsO_4$ and NMO and $KMnO_4$ and a base such as KOH, LiOH, and NaOH. Specific examples of solvents include toluene, benzene, xylene, acetone, and water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (1N) in room temperature acetone is treated with water, NMO and $OsO_4$ in toluene for about 3 hours.

The conversion of (9A) to (9B) can be accomplished by treating the former with an oxidizing agent in a solvent. Specific examples of oxidizing agents include $NaIO_4$, $HIO_4$, and $Pb(OAc)_4$. Specific examples of solvents include THF, methanol, ethanol, isopropanol, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (5A) in methanol at room temperature is treated with $NaIO_4$ in water for about three hours.

In an alternative synthesis, (9B) can be directly prepared from (1N) by treating the latter with a combination of oxidants in a solvent. Specific examples of oxidants include $OsO_4$, and $KMnO_4$ and a base such as KOH, LiOH, and NaOH, $NaIO_4$, $HIO_4$, and $Pb(OAc)_4$. Specific examples of solvents include toluene, benzene, xylene, acetone, water, and mixture thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (1N) in room temperature acetone is treated with water, $OsO_4$, and $NaIO_4$ for about three hours.

As shown in Scheme 17, the conversion of (9B) to (9C) can be accomplished by treating the former with a reducing agent in a solvent. Specific examples of reducing agents include $NaBH_4$, $NaBH_3CN$, and $BH_3 \cdot NH_2(C(CH_3)_3)$. Specific examples of solvents include methanol, ethanol, and isopropanol. Although the reaction generally proceeds at 0° C., it can be run at elevated temperatures, as needed. The reaction time is generally about 30 minutes to about 12 hours and can be selected depending on the reaction temperature. In a preferred embodiment, (9B) in methanol at 0° C. is treated with $NaBH_4$ for about 30 minutes.

The conversion of (9C) to (9D) can be accomplished by treating the former with a hydrolyzing agent in a solvent. Specific examples of hydrolyzing agents include acids and bases. More preferred are the following bases: LiOH, KOH and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (9C) in THF at room temperature is treated with aqueous LiOH for about 12 hours.

Scheme 17

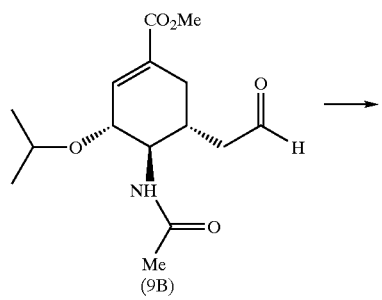

(9B)

Scheme 18

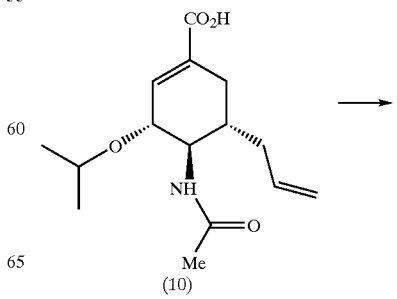

(10)

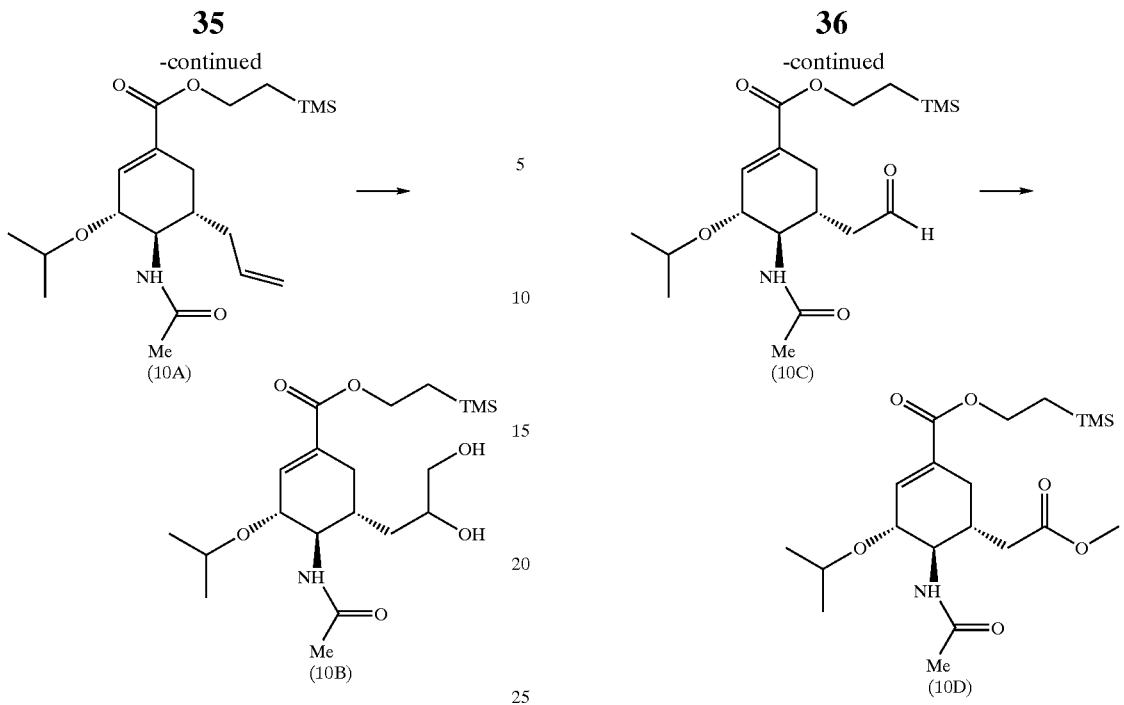

As shown in Scheme 18, the conversion of (1O) to (10A) can be accomplished by treating the former with a protecting group precursor, a base, and an additive in a solvent. A specific example of a protecting group precursor is 2-(trimethylsilyl)ethanol. A specific example of an additive is 2-chloro-1-methylpyridinium iodide. Specific examples of bases include TEA, diisopropylamine, and lutidine. Specific examples of solvents include DCM, THF, chloroform, and diethyl ether. Although the reaction generally proceeds at room temperature, it can be run at lower or elevated temperatures, as needed. The reaction time is generally about 30 minutes to about 24 hours and can be selected depending on the reaction temperature. In a preferred embodiment, (1O) in room temperature DCM is treated with 2-(trimethylsilyl)ethanol, TEA and 2-chloro-1-methylpyridinium iodide for about 16 hours.

The conversion of (10A) to (10B) can be accomplished by treating the former with an oxidant and bulk oxidant in a solvent. Specific examples of oxidant and bulk oxidants include: $OsO_4$ and NMO, and $KMnO_4$ and a base such as KOH, LiOH, and NaOH. Specific examples of solvents include toluene, benzene, xylene, acetone, and water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (10A) in room temperature acetone is treated with water, $OsO_4$ and NMO in toluene for about 3 hours.

Scheme 19

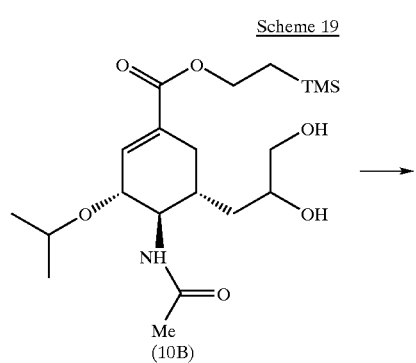

As shown in Scheme 19, the conversion of (10B) to (10C) can be accomplished by treating the former with an oxidizing agent in a solvent. Specific examples of oxidizing agents include $NaIO_4$, $HIO_4$, and $Pb(OAc)_4$. Specific examples of solvents include THF, methanol, ethanol, isopropanol, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a preferred embodiment, (10B) in methanol at room temperature is treated with $NaIO_4$ in water for about three hours.

The conversion of (10C) to (10D) can be accomplished by treating the former with an oxidizing agent and an additive in a solvent to generate the acid which can then be esterified. Specific examples of oxidizing agents include sodium chlorite in acidic buffer, $KMnO_4$, $H_2CrO_4$, AgO and $Na_2Cr_2O_7$. A specific example of an additive is 2-methyl-2-butene. Specific examples of solvents include THF, DCM, tertiary-butyl alcohol, methanol, ethanol, and isopropanol. Although the reaction generally proceeds at room temperature, it can be run at lower or elevated temperatures, as needed. The reaction time is generally about 30 minutes to about 24 hours and can be selected depending on the reaction temperature. In a preferred embodiment, (10C) in tertiary-butyl alcohol at room temperature is treated with sodium chlorite in $KH_2PO_4$ buffer and 2-methyl-2-butene for about 16 hours.

The acid can then be converted to (10D) by treating it with an esterifying reagent in a solvent. Specific examples of esterifying reagents include diazomethane, an alcohol and a mineral acid, and $SOCl_2$ followed by an alcohol. Specific examples of solvents include methanol, THF, DCM, TBME, and chloroform. Although the reaction generally proceeds at about 0° C., it can be run at elevated temperatures, as needed. The reaction time is generally about 5 minutes to about 6 hours and can be selected depending on the reaction temperature. In a preferred embodiment, (10D) in THF at 0° C. is treated with diazomethane for about 30 minutes.

Scheme 20

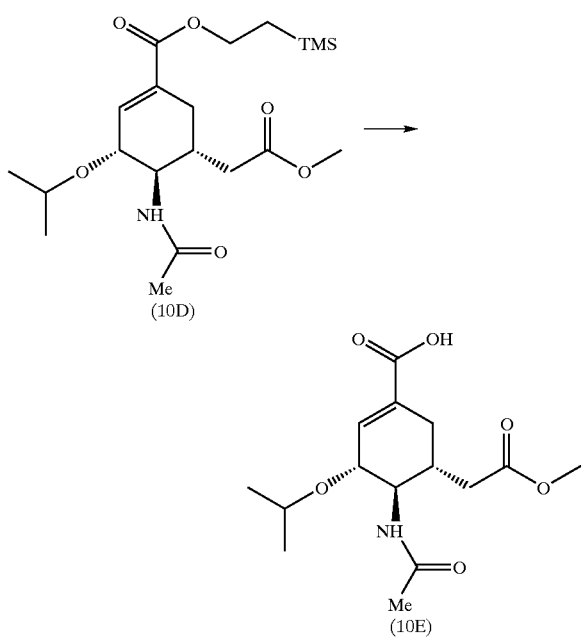

As shown in Scheme 20, the conversion of (10D) to (10E) can be accomplished by treating the former with a deprotecting agent in a solvent. Specific examples of deprotecting agents include TBAF, and HF. Specific examples of solvents include THF, DCM, chloroform, and diethyl ether. Although the reaction generally proceeds at room temperature, it can be run at lower or elevated temperatures, as needed. The reaction time is generally about 30 minutes to about 12 hours and can be selected depending on the reaction temperature. In a preferred embodiment, (10D) in THF at room temperature is treated TBAF for about three hours.

Scheme 21

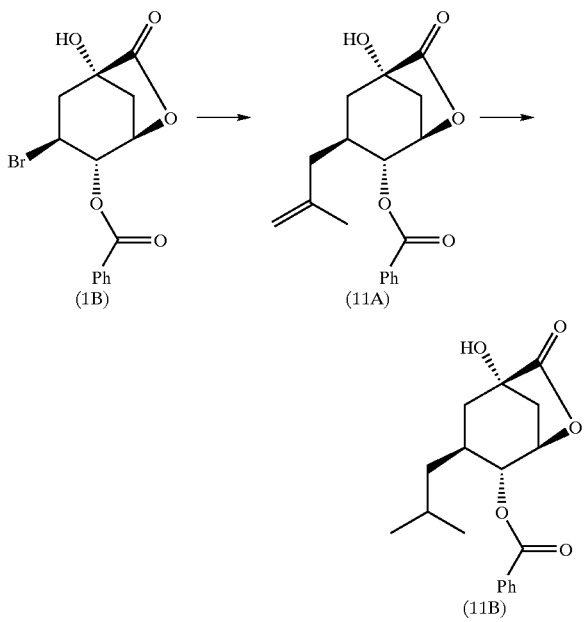

As shown in Scheme 21, the conversion of (1B) to (11A) can be accomplished by treating the former with an organostannane and a free radical initiator in a solvent. Specific examples of organostannanes include 2-(tributylstannyl)furan, tributyltin hydride, allyltributyltin, vinyltributyltin, and 2-(tributylstannyl)thiophene. Specific examples of free radical initiators include AIBN, and di-tertiary-butyl peroxide in the presence of ultraviolet light or heat. Specific examples of solvents include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, (1B), 2-methylallyl tributyltin and AIBN in benzene are refluxed for about 10 hours.

The conversion of (11A) to (11B) can be accomplished by treating the former with a catalyst and hydrogen, in a solvent. Specific examples of catalysts include palladium hydroxide, palladium on carbon, $PdCl_2$, and platinum on carbon. Specific sources of hydrogen include ammonium formate and hydrogen gas. Specific examples of solvents include EtOAc, isopropyl acetate, and THF. Although the reaction generally proceeds at room temperature, it can be run at lower or elevated temperatures, as needed. The reaction time is generally about 30 minutes to about 24 hours and can be selected depending on the reaction temperature. In a preferred embodiment, (11A) in ethyl acetate at room temperature is treated with palladium hydroxide and 40 PSI of hydrogen for about 10 hours.

Example 22

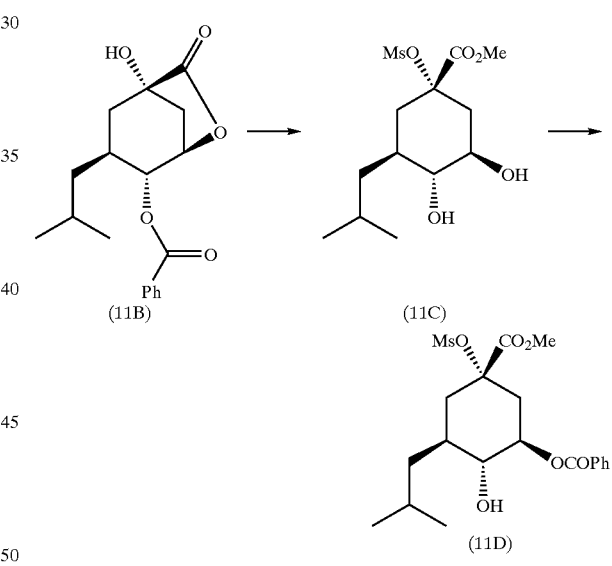

As shown in Scheme 22, the conversion of (11B) to (11C) can be accomplished by treating the former with sulfonyl chloride and a base in a solvent to generate an intermediate compound which can then be transesterified. Specific examples of sulfonyl chlorides include methanesulfonyl chloride, para-toluenesulfonyl chloride, and trifluoromethanesulfonyl chloride. Specific examples of bases include TEA, pyridine, pyrrolidine, and diisopropylethylamine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (11B) in DCM at 0° C. is treated with methanesulfonyl chloride and TEA for about 5 hours.

The intermediate compound is then converted to (11C) by treating the former with a base and an alcohol. Specific examples of bases include potassium carbonate, NaOMe, NaOEt, NaOH, and KOH. Specific examples of alcohols include methanol, ethanol, propanol and isopropanol. Co-solvents such as THF, TBME, DCM and chloroform can be added to the reaction mixture to enhance solubility of the starting materials and products. Although the reaction generally proceeds at room temperature, it can be run at lower or elevated temperatures, as needed. The reaction time is generally about 30 minutes to about 12 hours and can be selected depending on the reaction temperature. In a preferred embodiment, the intermediate compound in methanol at room temperature is treated with potassium carbonate for about one hour.

The conversion of (11C) to (11D) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine and pyridine. Specific examples of solvents include DCM, chloroform, THF, TBME, pyridine and diethyl ether. Although the reaction generally proceeds at about 0° C., it can be run at elevated temperatures, as needed. The reaction time is generally about 30 minutes to 24 hours and can be selected depending on the reaction temperature. In a preferred embodiment, (11C) in DCM at 0° C. is treated with benzoyl chloride, and pyridine for about 5 hours.

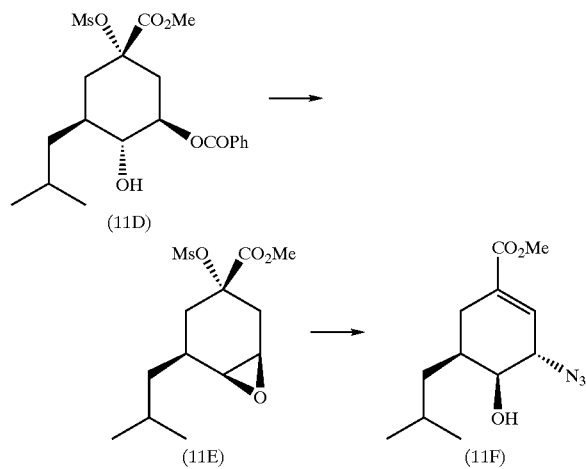

As shown in Scheme 23, the conversion of (11D) to (11E) can be accomplished by treating the former with sulfonyl chloride and a base in a solvent to generate an intermediate compound which can then be transesterified. Specific examples of sulfonyl chlorides include methanesulfonyl chloride, para-toluenesulfonyl chloride, and trifluoromethanesulfonyl chloride. Specific examples of bases include TEA, pyridine, pyrrolidine, and diisopropylethylamine. Specific examples of solvents include DCM, chloroform, THF, TBME and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (11D) in DCM at 0° C. is treated with methanesulfonyl chloride and TEA for about 10 hours.

The intermediate compound is then converted to (11E) by treating the former with a base and an alcohol. Specific examples of bases include potassium carbonate, NaOMe, NaOEt, NaOH, and KOH. Specific examples of alcohols include methanol, ethanol, propanol and isopropanol. Co-solvents such as THF, TBME, DCM and chloroform can be added to the reaction mixture to enhance solubility of the starting materials and products. Although the reaction generally proceeds at room temperature, it can be run at elevated temperatures, as needed. The reaction time is generally about 30 minutes to about 12 hours and can be selected depending on the reaction temperature. In a preferred embodiment, the intermediate compound in methanol is treated with potassium carbonate for about 10 hours.

The conversion of (11E) to (11F) can be accomplished by treating the former with a base to generate an intermediate which is then treated with a nucleophile. Specific examples of bases include DBU, potassium tertiary-butoxide, and diisopropylethylamine. Specific examples of solvents include THF, chloroform, TBME, and benzene. Although the reaction generally proceeds at reflux, it can be run at lower temperatures, as needed. The reaction time is generally about 30 minutes to about 12 hours and can be selected depending on the reaction temperature. In a preferred embodiment, (11E) in THF is treated with DBU and refluxed for about 6 hours to generate an intermediate compound.

The conversion of the intermediate compound to (11F) can be accomplished by treating the former with a nucleophile and an additive. Specific examples of nucleophiles include $NaN_3$, $TMSN_3$, TMSCl, TMSBr, carbanions, thioacetate, and cyanide. More preferred are the following nucleophiles: $NaN_3$ and $TMSN_3$. Specific examples of additives include acids and bases. More preferred are the following acids: $NH_4Cl$, $(NH_4)_2SO_4$, and AcOH. Specific examples of solvents include MeOH, EtOH, i-PrOH, NMP, water, and mixtures thereof. Although the reaction generally proceeds at reflux, the temperature of which can be determined by using a solvent of known boiling point at atmospheric pressure, it can be run at lower temperatures as needed. The reaction time is generally about 30 minutes to about 24 hours and can be selected depending on the reaction temperature. In a particularly preferred embodiment, the intermediate compound in a methanol-water mixture is treated with $NaN_3$ and $NH_4Cl$ and refluxed for about 5 hours.

Example 24

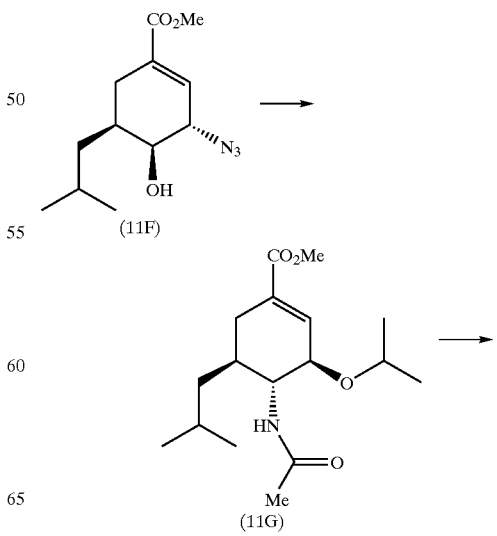

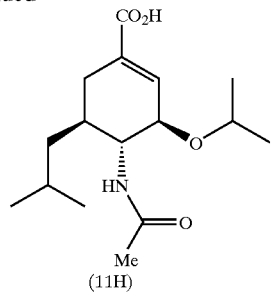

(11H)

As shown in Scheme 24, the conversion of (11F) to (11G) can be accomplished by treating the former with sulfonyl chloride and a base to generate an intermediate compound which can then be reduced to generate a second intermediate, protected to generate a third intermediate, treated with a Lewis acid and an alcohol to generate a fourth intermediate and acylated to generate 11H. Specific examples of sulfonyl chlorides include methanesulfonyl chloride, para-toluenesulfonyl chloride, and trifluoromethanesulfonyl chloride. Specific examples of bases include TEA, pyridine, pyrrolidine, and diisopropylethylamine. Specific examples of solvents include DCM, chloroform, THF, TBME and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (11F) in DCM at 0° C. is treated with methanesulfonyl chloride and TEA for about two hours to generate the first intermediate.

The conversion of the first intermediate to a second intermediate can be accomplished by treating the former with a reducing agent in a solvent. Specific examples of reducing agents include phosphines followed by water and a base, and H$_2$S and pyridine. More preferred are the following phosphines: PPh$_3$, and PEt$_3$. Specific examples of bases include TEA, NH$_4$OH, and NaOH. Specific examples of solvents include THF, MeOH, TBME and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (1K) in THF at room temperature is treated with PPh$_3$ for about two hours, followed by water and TEA for about 10 hours.

The conversion of the second intermediate to the third intermediate can be accomplished by treating the former with a protecting group and a base in a solvent. Specific examples of protecting groups include trityl, nosyl and brosyl. Specific examples of base include pyridine, TEA and 2,6-lutidine. Specific examples of solvents include DCM, THF, chloroform and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, the second intermediate in DCM at about 0° C. is treated with trityl chloride and TEA for about two hours.

The conversion of the third intermediate to the fourth intermediate can be accomplished by treating the former with a Lewis acid and an alcohol in a solvent to afford an intermediate which can then be treated with an acylating agent and a base. Specific examples of Lewis acids include ZnCl$_2$, TiCl$_4$, BF$_3$.OEt$_2$, and SnCl$_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, the third intermediate in about 75° C. isopropanol is treated with BF$_3$.OEt$_2$ for about two hours.

The conversion of the fourth intermediate to (11G) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, the fourth intermediate in pyridine at room temperature is treated with acetic anhydride and pyridine for about 12 hours.

The conversion of (11G) to (11H) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (11G) in THF at room temperature is treated with aqueous LiOH for about 12 hours.

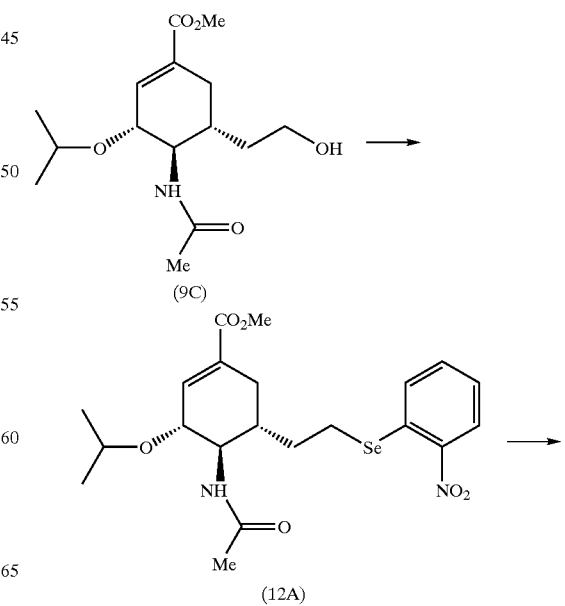

-continued

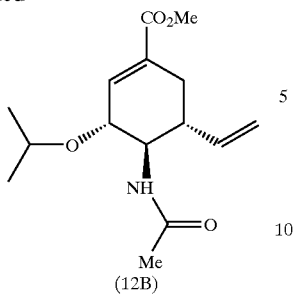

(12B)

As shown in Scheme 25, the conversion of (9C) to (12A) can be accomplished by treating the former with a phosphine, and a selenium compound in a solvent. Specific examples of phosphines include triphenylphosphine and tributylphosphine. A specific example of a selenium compound is ortho-nitrophenyl selenocyanate. Specific examples of solvents include THF, DCM, chloroform, and diethyl ether. Although the reaction generally proceeds at room temperature, it can be run at lower or elevated temperatures, as needed. The reaction time is generally about 30 minutes to about 12 hours and can be selected depending on the reaction temperature. In a preferred embodiment, (9C) in THF at room temperature is treated with tributylphosphine and ortho-nitrophenyl selenocyanate for about two hours.

The conversion of (12A) to (12B) can be accomplished by treating the former with a peroxide in a solvent. Specific examples of peroxides include hydrogen peroxide, di-tertiary-butyl peroxide, and ozone. Specific examples of solvents includes THF, DCM, chloroform, and diethyl ether. Although the reaction generally proceeds at room temperature, it can be run at lower or elevated temperatures, as needed. The reaction time is generally about 30 minutes to about 18 hours and can be selected depending on the reaction temperature. In a preferred embodiment, (12A) in THF at room temperature is treated with hydrogen peroxide for about 12 hours.

Scheme 26

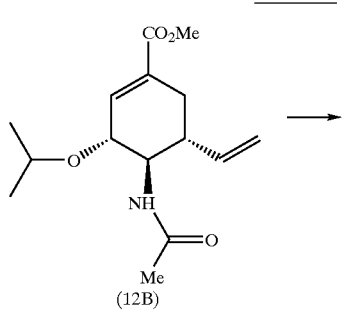

As shown in Scheme 26, the conversion of (12B) to (12C) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (12B) in THF at room temperature is treated with aqueous LiOH for about 12 hours.

Scheme 27

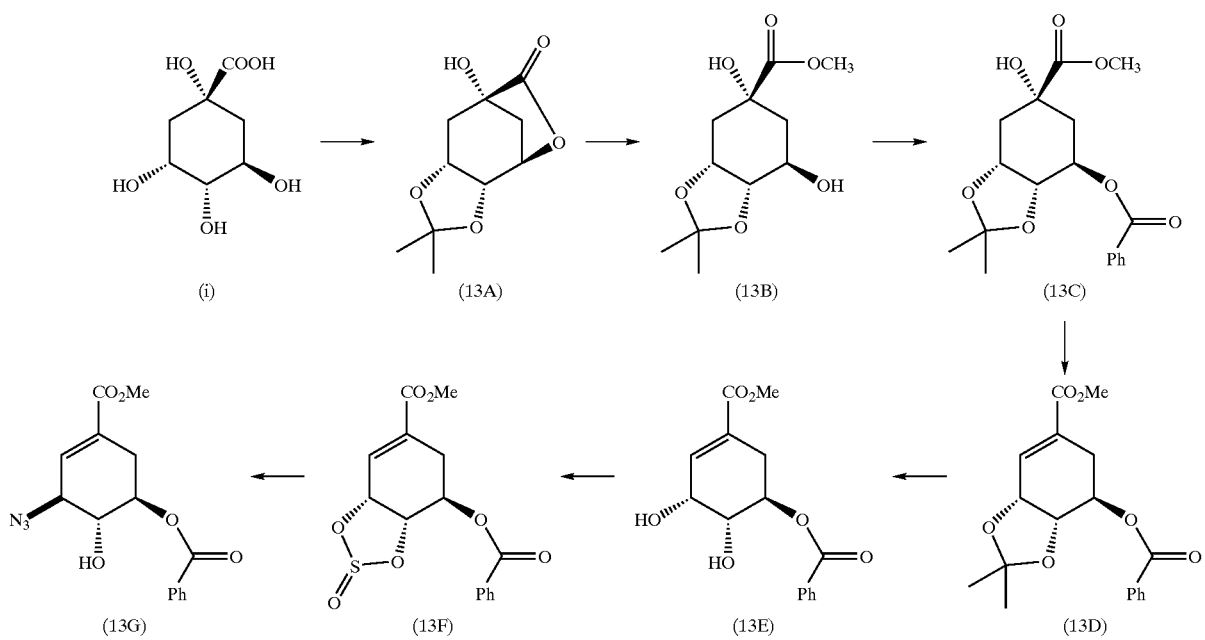

As shown in Scheme 27, conversion of (i) to (13A) can be accomplished by treating the former with an aldehyde, ketone or acetal in the presence of an acid. Specific examples of aldehydes, ketones, and acetals include benzaldehyde, 4-methoxybenzaldehyde, acetaldehyde, 3-pentanone, and 2,2-dimethoxy propane. Specific examples of acids include para-toluenesulfonic acid, trifluoroacetic acid, and concentrated hydrochloric acid. Specific examples of solvents include benzene, toluene, xylene, dichloromethane, acetone, and mixtures thereof. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, a solution of (i) in acetone is treated with 2,2-dimethoxy propane and para-toluenesulfonic acid and refluxed for about four hours.

The conversion of (13A) to (13B) can be achieved by treating the former with a base and an alcohol. Specific examples of bases include potassium carbonate, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials and products. Although the reaction generally proceeds at room temperature, it can be run at lower or elevated temperatures, as needed. The reaction time is generally about 30 minutes to about 12 hours and can be selected depending on the reaction temperature. In a preferred embodiment, (13A) in methanol at room temperature is treated with potassium carbonate for about one hour.

The conversion of (13B) to (13C) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (13B) in DCM at 0° C. is treated with benzoyl chloride, and pyridine for about 12 hours.

The conversion of (13C) to (13D) can be accomplished by treating the former with a chloride source and a base in a solvent. Specific examples of chloride sources include thionyl chloride and sulfuryl chloride. Specific examples of bases include pyridine, DBU, diisopropylethylamine, and TEA. Specific examples of solvents include DCM, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (13C) in DCM at 0° C. is treated with sulfuryl chloride and pyridine for about three hours.

The conversion of (13D) to (13E) can be accomplished by treating the former with an acid in an alcohol. Specific examples of acids include para-toluenesulfonic acid, trifluoroacetic acid, and concentrated hydrochloric acid. Specific examples of alcohols include methanol, ethanol, and isopropanol. Although the reaction generally proceeds at room temperature, it can be run at lower or elevated temperatures, as needed. The reaction time is generally about 30 minutes to about 18 hours and can be selected depending on the reaction temperature. In a preferred embodiment, (13D) in methanol at room temperature is treated with para-toluenesulfonic acid for about 16 hours.

The conversion of (13E) to (13F) can be accomplished by treating the former with an activating group and a base in a solvent. A specific example of an activating group is thionyl chloride. Specific examples of bases include TEA, diisopropylethylamine pyrrolidine, and pyridine. Specific examples of solvents include THF, DCM, TBME, and diethyl ether. Although the reaction generally proceeds at about 0° C., it can be run at elevated temperatures, as needed. The reaction time is generally about 15 minutes to about 12 hours and can be selected depending on the reaction temperature. In a preferred embodiment, (13E) in DCM at 0° C. is treated with thionyl chloride and TEA for about 30 minutes.

The conversion of (13F) to (13G) can be accomplished by treating the former with a nucleophile in a solvent. Specific examples of nucleophiles include $NaN_3$, $TMSN_3$, TMSCl, TMSBr, carbanions, thioacetate, and cyanide. More preferred are the following nucleophiles: $NaN_3$ and $TMSN_3$. Specific examples of solvents include MeOH, EtOH, i-PrOH, DMF, NMP, water, and mixtures thereof. Although the reaction generally proceeds at reflux, the temperature of which can be determined by using a solvent of known boiling point at atmospheric pressure, it can be run at lower temperatures as needed. The reaction time is generally about 30 minutes to about 24 hours and can be selected depending on the reaction temperature. In a particularly preferred embodiment, (13F) in room temperature DMF is treated with $NaN_3$ for about 16 hours.

Scheme 28

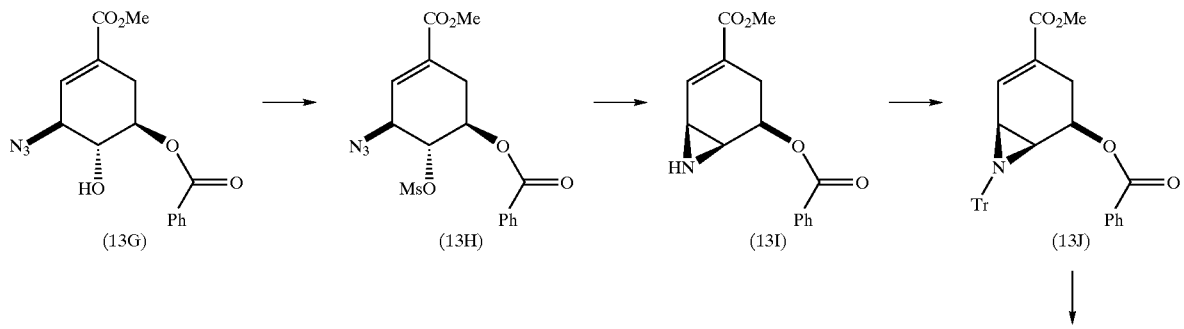

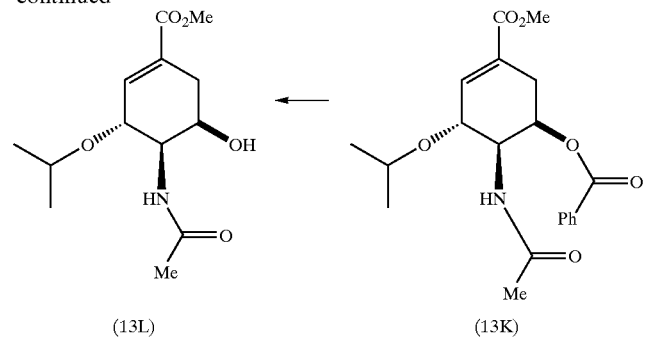

(13M)          (13L)          (13K)

As shown in Scheme 28, the conversion of (13G) to (13H) can be accomplished by treating the former with sulfonyl chloride and a base in a solvent. Specific examples of sulfonyl chlorides include methanesulfonyl chloride, para-toluenesulfonyl chloride, and trifluoromethanesulfonyl chloride. Specific examples of bases include TEA, pyridine, pyrrolidine, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (13G) in DCM at 0° C. is treated with methanesulfonyl chloride and TEA for about two hours.

The conversion of (13H) to (13I) can be accomplished by treating the former with a reducing agent in a solvent. Specific examples of reducing agents include phosphines followed by water and a base, and $H_2S$ and pyridine. More preferred are the following phosphines: $PPh_3$, and $PEt_3$. Specific examples of bases include TEA, $NH_4OH$, and NaOH. Specific examples of solvents include THF, MeOH, TBME, and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (13H) in THF at room temperature is treated with $PPh_3$ for about two hours, followed by water and TEA for about 10 hours.

The conversion (13I) to (13J) can be accomplished by treating the former with a protecting group and a base in a solvent. Specific examples of protecting groups include trityl, nosyl, and brosyl. Specific examples of base include pyridine, TEA, and 2,6-lutidine. Specific examples of solvents include DCM, THF, chloroform, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (13I) in DCM at about 0° C. is treated with trityl chloride and TEA for about two hours.

The conversion of (13J) to (13K) can be accomplished by treating the former with a Lewis acid and an alcohol in a solvent to afford an intermediate which can then be treated with an acylating agent and a base. Specific examples of Lewis acids include $ZnCl_2$, $TiCl_4$, $BF_3.OEt_2$, and $SnCl_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM, and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (13J) in isopropanol is treated with $BF_3.OEt_2$ and heated to about 75° C. for about two hours.

The conversion of (13K) to (13L) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (13K)in pyridine is treated with acetic anhydride for about 12 hours.

The conversion of (13L) to (13M) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (13L) in THF at room temperature is treated with aqueous LiOH for about 12 hours.

Scheme 29

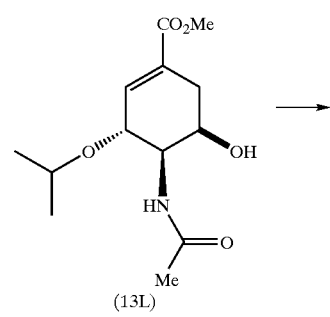

(13L)

-continued

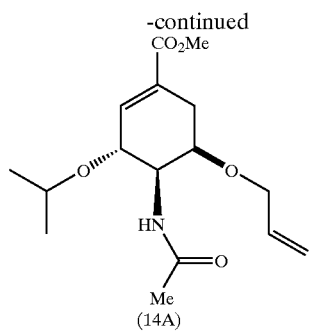
(14A)

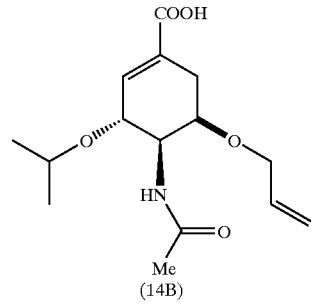
(14B)

-continued

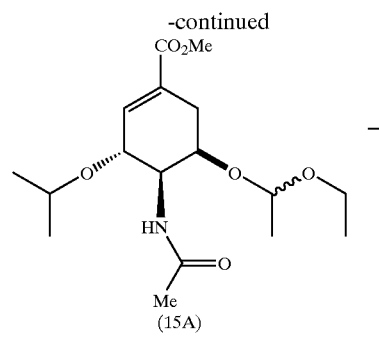
(15A)

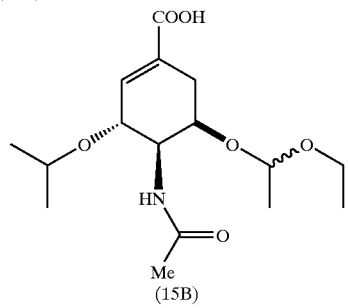
(15B)

As shown in Scheme 29, the conversion of (13L) to (14A) can be accomplished by treating the former with a base and an alkylating agent in a solvent. Specific examples of alkylating agents include MeI, EtBr, allyl bromide, benzyl bromide, and isopropyl bromide. Specific examples of bases include NaH, KH, $K_2CO_3$, pyridine, and DBU. Specific examples of solvents include THF, DMF, DCM, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (13L) in THF at 0° C. is treated with NaH and allyl bromide for about 5 hours.

The conversion of (14A) to (14B) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (14A) in THF at room temperature is treated with aqueous LiOH for about 12 hours.

As shown in Scheme 30, the conversion of (13L) to (15A) is accomplished by treating the former with a protecting group precursor and an additive in a solvent. Specific examples of protecting groups include vinyl ether, benzyl, TBS, and acetyl. Specific examples of additives include acids and bases. More preferred are the following acids: para-toluenesulfonic acid, triflic acid, TFA, and concentrated hydrochloric acid. Specific examples of solvents include vinyl ether, DCM, THF, and TBME. Although the reaction generally proceeds at room temperature, it can be run at lower or elevated temperatures, as needed. The reaction time is generally about 30 minutes to about 18 hours and can be selected depending on the reaction temperature. In a preferred embodiment, (13L) in room temperature vinyl ether is treated with TFA for about 16 hours.

The conversion of (15A) to (15B) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (15A) in THF at room temperature is treated with aqueous LiOH for about 10 hours.

Scheme 30

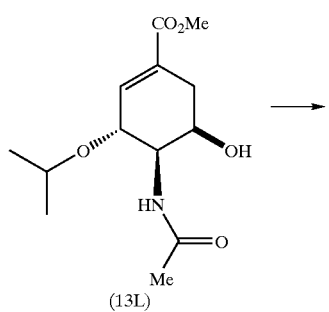
(13L)

Scheme 31

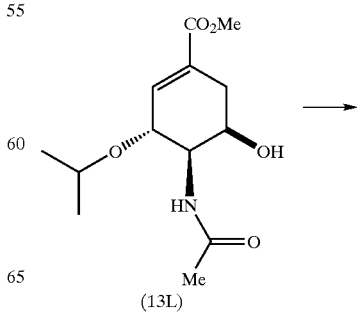
(13L)

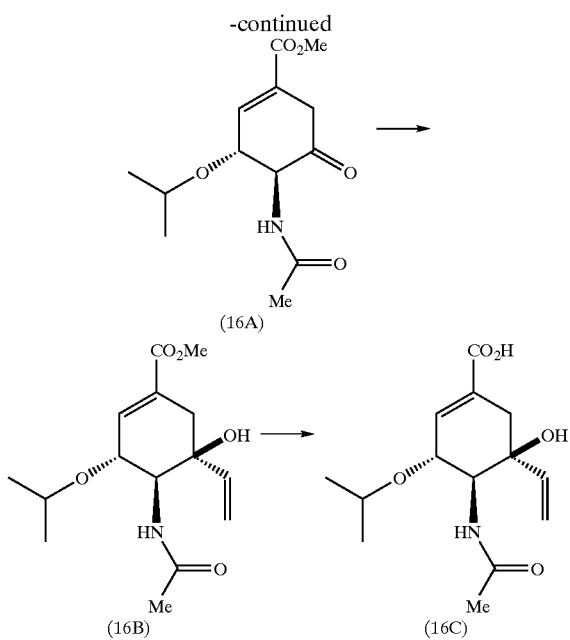

As shown in Scheme 31, the conversion of (13L) to (16A) can be accomplished by treating the former with an oxidizing agent in a solvent. Specific examples of oxidizing agents include PCC coated on $Al_2O_3$, oxalyl chloride and DMSO, $KMNO_4$, and $Cr_2O_7^{2-}$. Specific examples of solvents include DCM, THF, TBME, and diethyl ether.

Although the reaction generally proceeds at room temperature, it can be run at lower or elevated temperatures, as needed. The reaction time is generally about 30 minutes to about 12 hours and can be selected depending on the reaction temperature. In a preferred embodiment, a solution of (13L) in DCM can be treated with PCC on $Al_2O_3$ for about 8 hours.

The conversion of (16A) to (16B) can be accomplished by treating the former with a nucleophile in a solvent such as diethyl ether, THF, and TBME. Specific examples of nucleophiles include anions, Grignard reagents, azides, organozincates, organophosphorus compounds, tin enolates, and nitriles. More preferred are the following nucleophiles: ethyl magnesium bromide, n-propyl magnesium bromide, isopropyl magnesium bromide, 1-buten-4-yl magnesium bromide, isobutyl magnesium bromide, 2-butyl magnesium bromide, the anion of acetonitrile, the anion of ethyl ethoxyacetate, the anion of ethyl acetate, the anion of (ethoxyethyloxymethyl)tributylstannane, vinyl magnesium bromide, and methyl magnesium bromide. Although the reaction generally proceeds at $-78°$ C., it can be run at lower or elevated temperatures, as needed. The reaction time is generally about 15 minutes to about 4 hours and can be selected depending on the reaction temperature. In a particularly preferred embodiment, a room temperature solution of vinyl magnesium bromide in THF can be treated with (16A) in THF for about two hours.

The conversion of (16B) to (16C) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (16B) in THF at room temperature can be treated with aqueous LiOH for about 10 hours.

Scheme 32

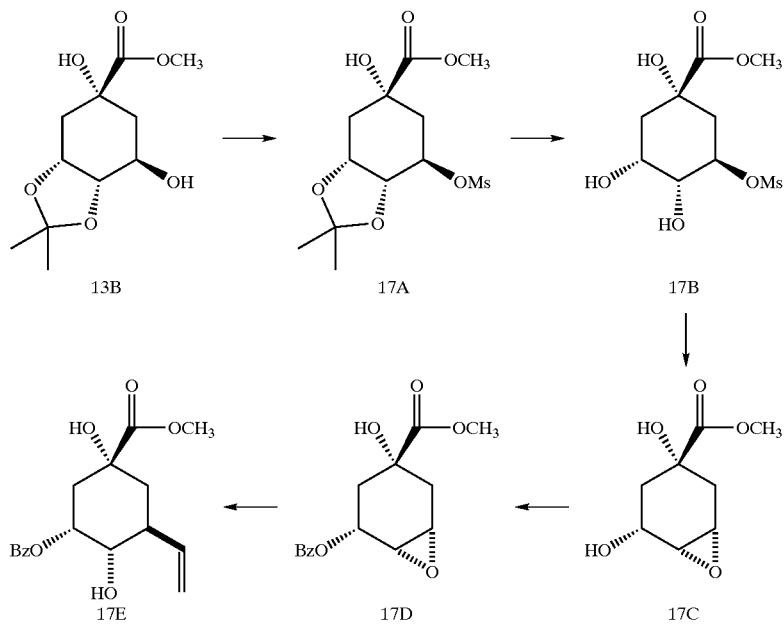

As shown in Scheme 32, the conversion of (13B) to (17A) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (13B) in DCM at about 0° C., is treated with methanesulfonyl chloride and TEA for about 10 hours.

The conversion of (17A) to (17B) is accomplished by treating the former with an acid in an alcohol. Specific examples of acids include para-toluenesulfonic acid, triflic acid, trifluoroacetic acid, and concentrated hydrochloric acid. Specific examples of alcohols include methanol, ethanol, and isopropanol. Although the reaction generally proceeds at room temperature, it can be run at lower or elevated temperatures, as needed. The reaction time is generally about 30 minutes to about 18 hours and can be selected depending on the reaction temperature. In a preferred embodiment, (17A) in methanol is treated with para-toluenesulfonic acid for about 16 hours.

The conversion of (17B) to (17C) is accomplished by treating the former with a base and an alcohol. Specific examples of bases include $K_2CO_3$, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials. Although the reaction generally proceeds at room temperature, it can be run at lower or elevated temperatures, as needed. The reaction time is generally about 30 minutes to about 12 hours and can be selected depending on the reaction temperature. In a preferred embodiment, (17B) in methanol at room temperature is treated with potassium carbonate for about 5 hours.

The conversion of (17C) to (17D) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, (17C) in DCM at about 0° C. is treated with benzoyl chloride and TEA for about 5 hours.

The conversion of (17D) to (17E) can be accomplished by treating the former with a Lewis acid, a nucleophile, and a transition metal halide. Specific examples of Lewis acids include $ZnCl_2$, $TiCl_4$, $BF_3.OEt_2$, and $SnCl_4$. Specific examples of nucleophiles include anions, Grignard reagents, azides, organozincates, organophosphorus compounds, tin enolates, and nitriles. More preferred are the following Grignard reagents: vinyl magnesium bromide, methylmagnesium bromide, and ethylmagnesium bromide. Specific examples of transition metal halides include CuI, and CuBr. Specific examples of solvents include THF, diethyl ether, and TBME. Although the reaction generally proceeds at about −78° C., it can be run at elevated temperatures, as needed. The reaction time is generally about 30 minutes to about 12 hours and can be selected depending on the reaction temperature. In a particularly preferred embodiment, a suspension of CuI and vinyl magnesium bromide in −78° C. THF can be treated with a solution of (17D) and $BF_3.OEt_2$ in THF.

Scheme 33

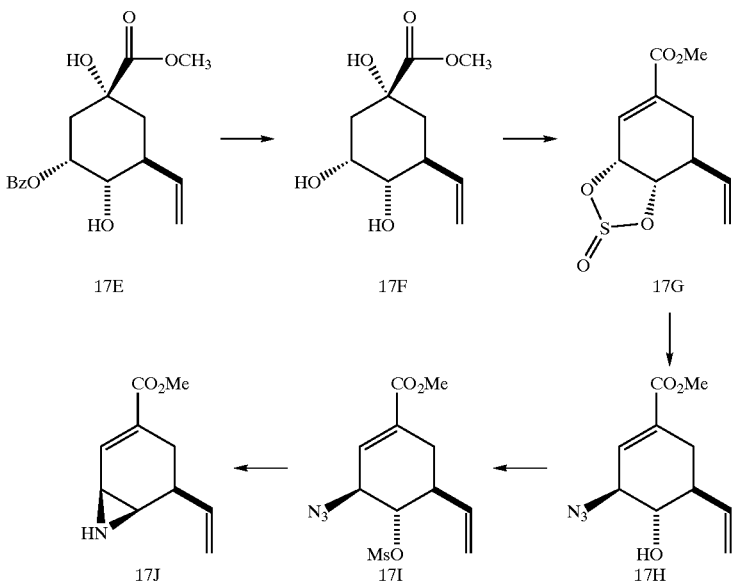

As shown in Scheme 33, the conversion of (17E) to (17F) is accomplished by treating the former with a base and an alcohol. Specific examples of bases include $K_2CO_3$, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials. Although the reaction generally proceeds at room temperature, it can be run at lower or elevated temperatures, as needed. The reaction time is generally about 30 minutes to about 12 hours and can be selected depending on the reaction temperature. In a preferred embodiment, (17E) in methanol at room temperature can be treated with potassium carbonate for about one hour.

The conversion of (17F) to (17G) can be accomplished by treating the former with an activating group and a base in a solvent. A specific example of an activating group is thionyl chloride. Specific examples of bases include TEA, diisopropylethylamine pyrrolidine, and pyridine. Specific examples of solvents include THF, DCM, TBME, and diethyl ether. Although the reaction generally proceeds at about 0° C., it can be run at elevated temperatures, as needed. The reaction time is generally about 15 minutes to about 12 hours and can be selected depending on the reaction temperature. In a preferred embodiment, (17F) in DCM at 0° C. can be treated with thionyl chloride and TEA for about 30 minutes.

The conversion of (17G) to (17H) can be accomplished by treating the former with a nucleophile in a solvent. Specific examples of nucleophiles include $NaN_3$, $TMSN_3$, TMSCl, TMSBr, carbanions, thioacetate, and cyanide. More preferred are the following nucleophiles: $NaN_3$ and $TMSN_3$. Specific examples of solvents include MeOH, EtOH, i-PrOH, NMP, DMF, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (17G) in room temperature DMF can be treated with $NaN_3$ for about 16 hours.

The conversion of (17H) to (17I) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (17H) in DCM at about 0° C., is treated with methanesulfonyl chloride and TEA for about two hours.

The conversion of (17I) to (17J) can be accomplished by treating the former with a reducing agent in a solvent. Specific examples of reducing agents include phosphines followed by water and a base, and $H_2S$ and pyridine. More preferred are the following phosphines: $PPh_3$, and $PEt_3$. Specific examples of bases include TEA, $NH_4OH$, and NaOH. Specific examples of solvents include THF, MeOH, TBME, and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (17I) in THF at room temperature can be treated with $PPh_3$ for about two hours, followed by water and TEA for about 10 hours.

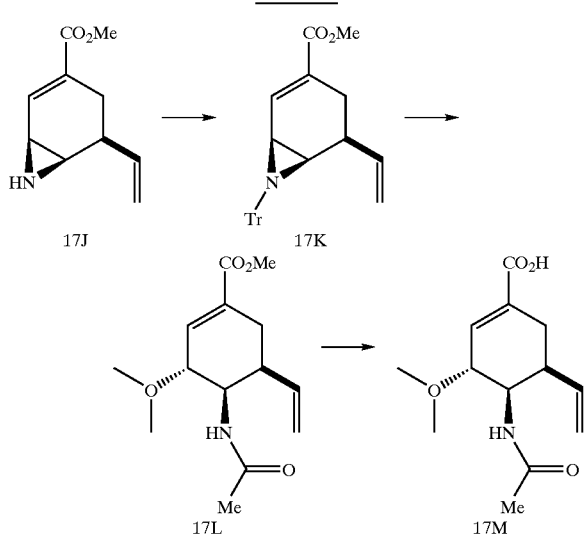

Scheme 34

As shown in Scheme 34, the conversion of (17J) to (17K) can be accomplished by treating the former with a protecting group and a base in a solvent. Specific examples of protecting groups include trityl, nosyl, and brosyl. Specific examples of base include pyridine, TEA, and 2,6-lutidine. Specific examples of solvents include DCM, THF, chloroform, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (17J) in DCM at about 0° C. can be treated with trityl chloride and TEA for about two hours.

The conversion of (17K) to (17L) can be accomplished by treating the former with a Lewis acid and an alcohol in a solvent to afford an intermediate which can then be treated with an acylating agent and a base. Specific examples of Lewis acids include $ZnCl_2$, $TiCl_4$, $BF_3.OEt_2$, and $SnCl_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM, and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (17K) in isopropanol can be treated with $BF_3.OEt_2$ and heated to about 75° C. for about two hours.

The conversion of the intermediate to (17L) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, the intermediate in pyridine at room temperature can be treated with acetic anhydride and pyridine for about 12 hours.

The conversion of (17L) to (17M) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (17L) in THF at room temperature can be treated with aqueous LiOH for about 10 hours.

2,6-lutidine. Specific examples of solvents include DCM, THF, chloroform, DMF, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (18A) in DMF at 0° C. can be treated with TBDMSCl and imidazole for about 16 hours.

The conversion of (18B) to (18C) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, Scheme 35

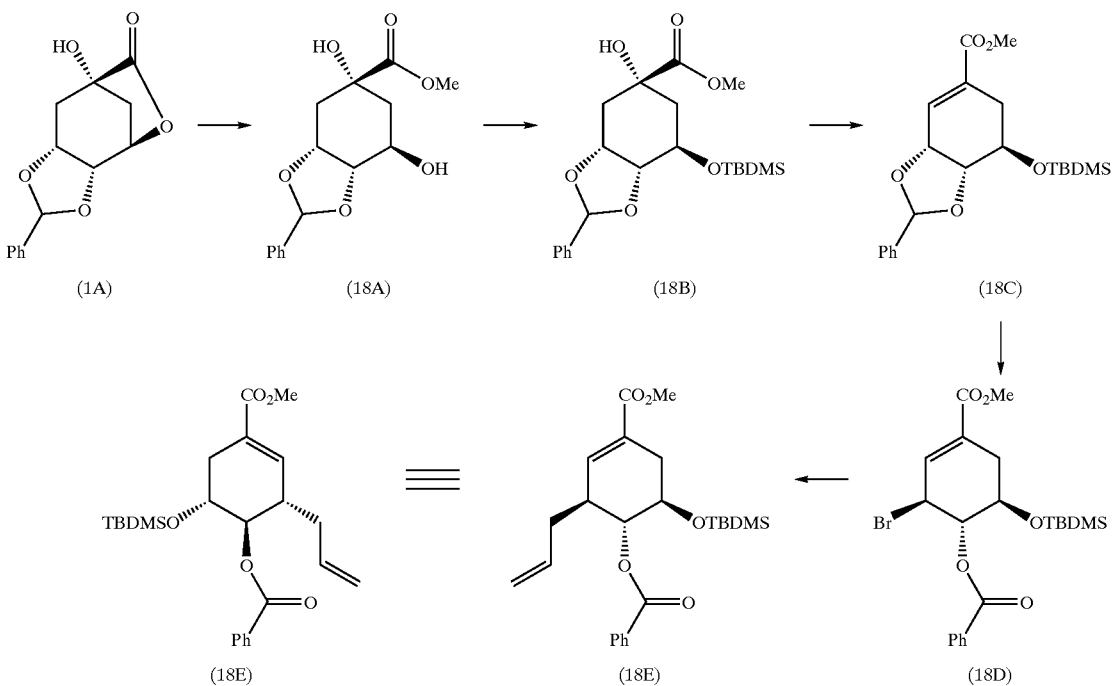

As shown in Scheme 35, the conversion of (1A) to (18A) can be accomplished by treating the former with a base and an alcohol. Specific examples of bases include potassium carbonate, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials. Although the reaction generally proceeds at room temperature, it can be run at lower or elevated temperatures, as needed. The reaction time is generally about 30 minutes to about 12 hours and can be selected depending on the reaction temperature. In a preferred embodiment, (1A) in methanol at room temperature can be treated with potassium carbonate for about one hour.

The conversion of (18A) to (18B) can be accomplished by treating the former with a protecting group precursor and an additive in a solvent. Specific examples of protecting groups include benzyl, TMS, TES, and TBDMS. Specific examples of additives include acids and bases. More preferred are the following bases: pyridine, TEA, DMAP, imidazole, and and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (18B) in DCM at about 0° C., is treated with methanesulfonyl chloride and TEA for about 16 hours.

Conversion of (18C) to (18D) can be accomplished by treating the former with a free radical precursor and a free radical initiator in a solvent. Specific examples of free radical precursors include N-bromosuccinimide, N-chlorosuccinimide, $Br_2$, and $Cl_2$. Specific examples of free radical initiators include AIBN, and di-tertiary-butyl peroxide in the presence of ultraviolet light or heat. Specific examples of solvents include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, (18C) can be treated with AIBN and N-bromosuccinimide in refluxing benzene for about four hours.

The conversion of (18D) to (18E) can be accomplished by treating the former with an organostannane and a free radical initiator in a solvent. Specific examples of organostannanes include 2-(tributylstannyl)furan, tributyltin hydride, allyltributyltin, vinyltributyltin, and 2-(tributylstannyl) thiophene. Specific examples of free radical initiators include AIBN, and di-tertiary-butyl peroxide in the presence of ultraviolet light or heat. Specific examples of solvents include benzene, toluene, and xylene. The reaction generally proceeds at reflux, the temperature of which can be determined by using a solvent of known boiling point at atmospheric pressure. The reaction time is generally about 1 hour to about 24 hours and can be selected depending on the reaction temperature. In a preferred embodiment, (18D), allyltributyltin and AIBN in benzene can be refluxed for about 10 hours.

reaction temperature. In a preferred embodiment, (18E) in methanol at room temperature can be treated with potassium carbonate for about 16 hours.

The conversion of the first intermediate to the second intermediate can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, the first intermediate in DCM at about 0° C., is treated with methanesulfonyl chloride, and TEA for about 12 hours.

Scheme 36

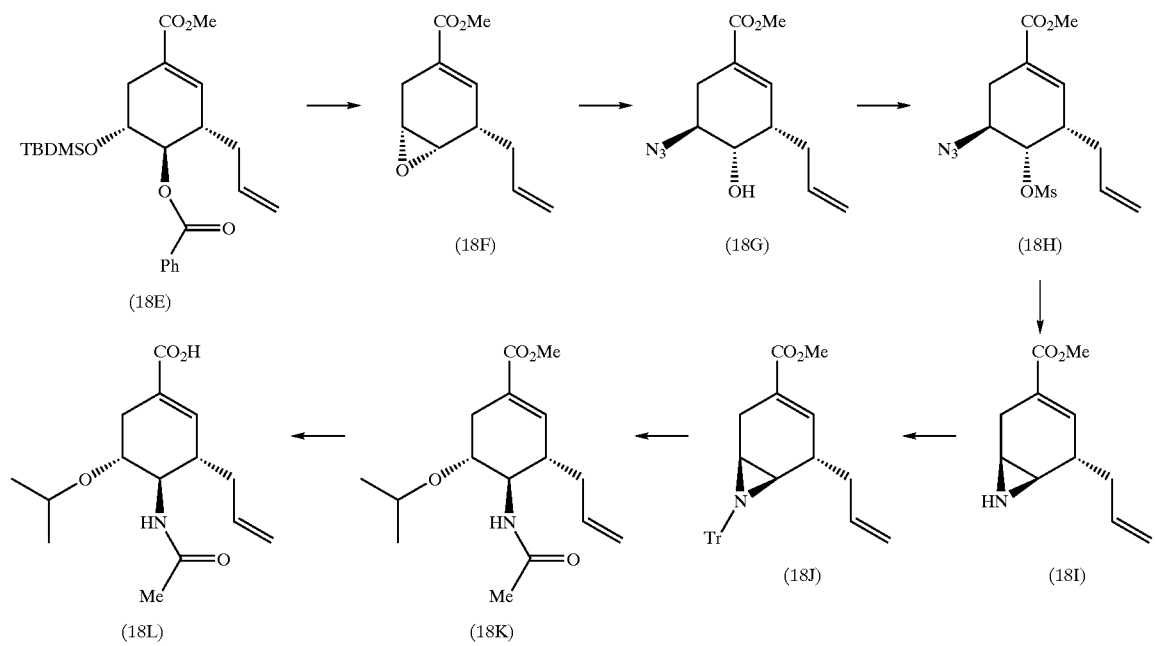

As shown in Scheme 36, the conversion of (18E) to (18F) can be accomplished by first, treating the former with a base and an alcohol to form the first intermediate, which can then be treated with a sulfonyl chloride and base to yield the second intermediate, which can be treated with a deprotecting agent to yield (18F). Specific examples of bases include potassium carbonate, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials. Although the reaction generally proceeds at room temperature, it can be run at lower or elevated temperatures, as needed. The reaction time is generally about 30 minutes to about 18 hours and can be selected depending on the The conversion of the third intermediate to (18F) can be accomplished by treating the former with a deprotecting agent in a solvent. Specific examples of deprotecting agents include HF and TBAF. Specific examples of solvents include THF, DCM, TBME, and diethylether. Although the reaction generally proceeds at room temperature, it can be run at lower or elevated temperatures, as needed. The reaction time is generally about 30 minutes to about 18 hours and can be selected depending on the reaction temperature. In a preferred embodiment, the third intermediate in THF at room temperature can be treated with TBAF for about 12 hours.

The conversion of (18F) to (18G) can be accomplished by treating the former with a nucleophile in a solvent. Specific examples of nucleophiles include $NaN_3$, $TMSN_3$, TMSCl, TMSBr, carbanions, thioacetate, and cyanide. More preferred are the following nucleophiles: NaN$_3$ and TMSN$_3$. Specific examples of solvents include MeOH, EtOH, i-PrOH, NMP, DMF, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (18F) in room temperature DMF can be treated with NaN$_3$ for about 16 hours.

The conversion of (18G) to (18H) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as PPh$_3$, and PBu$_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (18G) in DCM at about 0° C., is treated with methanesulfonyl chloride and TEA for about two hours.

The conversion of (18H) to (18I) can be accomplished by treating the former with a reducing agent in a solvent. Specific examples of reducing agents include phosphines followed by water and a base, and H$_2$S and pyridine. More preferred are the following phosphines: PPh$_3$, and PEt$_3$. Specific examples of bases include TEA, NH$_4$OH, and NaOH. Specific examples of solvents include THF, MeOH, TBME, and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (18H) in THF at room temperature can be treated with PPh$_3$ for about two hours, followed by water and TEA for about 10 hours.

The conversion of (18I) to (18J) can be accomplished by treating the former with a protecting group and a base in a solvent. Specific examples of protecting groups include trityl, nosyl, and brosyl. Specific examples of base include pyridine, TEA, and 2,6-lutidine. Specific examples of solvents include DCM, THF, chloroform, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (18I) in DCM at about 0° C. can be treated with trityl chloride and TEA for about two hours.

The conversion of (18J) to (18K) can be accomplished by treating the former with a Lewis acid and an alcohol in a solvent to afford an intermediate which can then be treated with an acylating agent and a base. Specific examples of Lewis acids include ZnCl$_2$, TiCl$_4$, BF$_3$.OEt$_2$, and SnCl$_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM, and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (18J) in isopropanol can be treated with BF$_3$.OEt$_2$ and heated to about 75° C. for about two hours.

The conversion of the intermediate to (18K) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, the intermediate in pyridine at room temperature can be treated with acetic anhydride and pyridine for about 12 hours.

The conversion of (18K) to (18L) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (18K) in THF at room temperature can be treated with aqueous LiOH for about 10 hours.

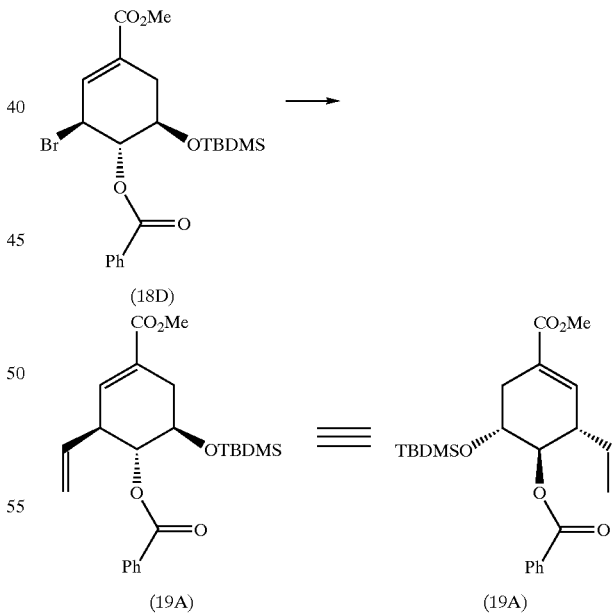

Scheme 37

As shown in Scheme 37, the conversion of (18D) to (19A) can be accomplished by treating the former with a transition metal catalyst and an organostannane in a solvent. Specific examples of a transition metal catalysts include palladium on carbon, platinum on carbon, PdCl$_2$, Pd(PPh$_3$)$_4$, and bis(dibenzylidenacetone)palladium(O). It can be necessary to add a ligand for the transition metal catalyst. Specific examples include triphenylphosphine, dba, and dppf. Specific examples of organostannanes include vinyltributyltin, (ethoxyethyloxymethyl)tributylstannane, and allyltributyltin. Specific examples of solvents include THF, TBME,, and diethylether. Although the reaction generally proceeds at about 55° C., it can be run at lower or elevated temperatures, as needed. The reaction time is generally about 24 hours to about 48 hours and can be selected depending on the types of starting materials and the reaction temperature. In a preferred embodiment, (18D) in THF can be treated with triphenylphosphine, vinyltributyltin, and bis(dibenzylideneacetone)palladium(0) and heated to about 55° C. for about 24 hours.

Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, the first intermediate in DCM at about 0° C., is treated with methanesulfonyl chloride and TEA for about 12 hours.

The conversion of the third intermediate to (19B) can be accomplished by treating the former with a deprotecting Scheme 38

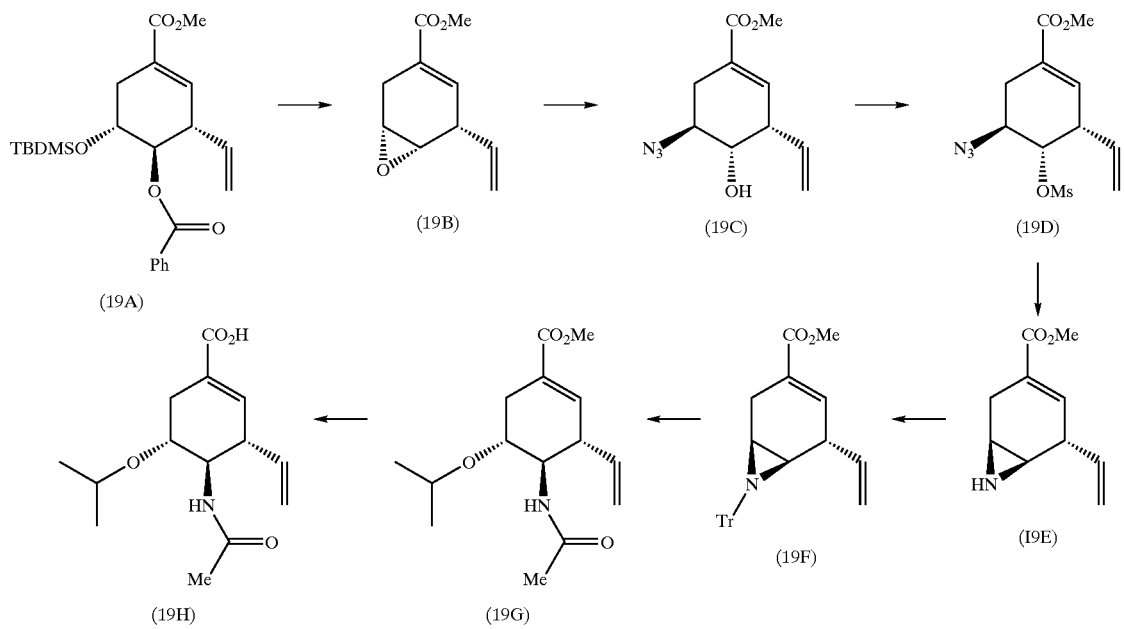

As shown in Scheme 38, the conversion of (19A) to (19B) can be accomplished by first, treating the former with a base and an alcohol to form the first intermediate, which can then be treated with a sulfonyl chloride and base to yield the second intermediate, which can be treated with a deprotecting agent to yield (19B). Specific examples of bases include potassium carbonate, NaOMe, NaOEt, NaOH, and KOH. Specific examples of alcohols include methanol, ethanol, propanol, and isopropanol. Co-solvents such as THF, TBME, DCM, and chloroform can be added to the reaction mixture to enhance solubility of the starting materials. Although the reaction generally proceeds at room temperature, it can be run at lower or elevated temperatures, as needed. The reaction time is generally about 30 minutes to about 18 hours and can be selected depending on the reaction temperature. In a preferred embodiment, (19A) in methanol at room temperature can be treated with potassium carbonate for about 16 hours.

The conversion of the first intermediate to the second intermediate can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride.

agent in a solvent. Specific examples of deprotecting agents include HF and TBAF. Specific examples of solvents include THF, DCM, TBME, and diethylether. Although the reaction generally proceeds at room temperature, it can be run at lower or elevated temperatures, as needed. The reaction time is generally about 30 minutes to about 18 hours and can be selected depending on the reaction temperature. In a preferred embodiment, the third intermediate in THF at room temperature can be treated with TBAF for about 12 hours.

The conversion of (19B) to (19C) can be accomplished by treating the former with a nucleophile in a solvent. Specific examples of nucleophiles include $NaN_3$, $TMSN_3$, TMSCl, TMSBr, carbanions, thioacetate, and cyanide. More preferred are the following nucleophiles: $NaN_3$ and $TMSN_3$. Specific examples of solvents include MeOH, EtOH, i-PrOH, NMP, DMF, water, and mixtures thereof. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (19B) in room temperature DMF can be treated with $NaN_3$ for about 16 hours.

The conversion of (19C) to (19D) can be accomplished by treating the former with a hydroxyl activating group precursor and an additive in a solvent. Specific examples of hydroxyl activating group precursors include trifluoroacetic anhydride, azo compounds such as DEAD, DIAD, and AIBN and phosphines such as $PPh_3$, and $PBu_3$, trifluoromethanesulfonic anhydride, methanesulfonyl chloride, and para-toluenesulfonyl chloride. Specific examples of additives include acids and bases. More preferred are the following bases: KOH, TEA, pyridine, pyrrolidine, DMAP, DBU, and diisopropylethylamine. Specific examples of solvents include DCM, chloroform, THF, TBME, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (19C) in DCM at about 0° C., is treated with methanesulfonyl chloride and TEA for about two hours.

The conversion of (19D) to (19E) can be accomplished by treating the former with a reducing agent in a solvent. Specific examples of reducing agents include phosphines followed by water and a base, and $H_2S$ and pyridine. More preferred are the following phosphines: $PPh_3$, and $PEt_3$. Specific examples of bases include TEA, $NH_4OH$, and NaOH. Specific examples of solvents include THF, MeOH, TBME, and DCM. Although the reaction generally proceeds at room temperature, it can be run at lower or elevated temperatures, as needed. The reaction time is generally about 30 minutes to about 12 hours and can be selected depending on the reaction temperature. In a preferred embodiment, (19D) in THF at room temperature can be treated with $PPh_3$ for about two hours, followed by water and TEA for about 10 hours.

The conversion of (19E) to (19F) can be accomplished by treating the former with a protecting group and a base in a solvent. Specific examples of protecting groups include trityl, nosyl, and brosyl. Specific examples of base include pyridine, TEA, and 2,6-lutidine. Specific examples of solvents include DCM, THF, chloroform, and diethyl ether. Although the reaction generally proceeds at about 0° C., it can be run at elevated temperatures, as needed. The reaction time is generally about 30 minutes to about 12 hours and can be selected depending on the reaction temperature. In a preferred embodiment, (19E in DCM at about 0° C. can be treated with trityl chloride and TEA for about two hours.

The conversion of (19F) to (19G) can be accomplished by treating the former with a Lewis acid and an alcohol in a solvent to afford an intermediate which can then be treated with an acylating agent and a base. Specific examples of Lewis acids include $ZnCl_2$, $TiCl_4$, $BF_3.OEt_2$, and $SnCl_4$. Specific examples of alcohols include methanol, ethanol, isopropanol, 3-pentanol, benzhydrol, and benzyl alcohol. Specific examples of solvents include an aforementioned alcohol, THF, 1,1,1-trichloroethane, DCM, and chloroform. Although the reaction generally proceeds at about 75° C., it can be run at lower or elevated temperatures, as needed. The reaction time is generally about 30 minutes to about 12 hours and can be selected depending on the reaction temperature. In a preferred embodiment, (19F) in isopropanol can be treated with $BF_3.OEt_2$ and heated to about 75° C. for about two hours.

The conversion of the intermediate to (19G) can be accomplished by treating the former with an acylating agent and a base in a solvent. Specific examples of acylating agents include acetyl chloride, benzoyl chloride, and acetic anhydride. Specific examples of bases include TEA, DMAP, pyrrolidine, diisopropylethylamine, and pyridine. Specific examples of solvents include DCM, chloroform, THF, TBME, pyridine, and diethyl ether. Although the reaction generally proceeds at about 0° C., it can be run at elevated temperatures, as needed. The reaction time is generally about 30 minutes to about 24 hours and can be selected depending on the reaction temperature. In a preferred embodiment, the intermediate in pyridine at room temperature can be treated with acetic anhydride and pyridine for about 12 hours.

The conversion of (19G) to (19H) can be accomplished by treating the former with a hydrolyzing agent in a solvent. Specific examples of hydrolyzing agents include acids and bases. More preferred are the following bases: LiOH, KOH, and NaOH. Specific examples of solvents include THF, MeOH, DCM, diethyl ether, and chloroform. Although the reaction generally proceeds at room temperature, it can be run at lower or elevated temperatures, as needed. The reaction time is generally about 30 minutes to about 12 hours and can be selected depending on the reaction temperature. In a particularly preferred embodiment, (19G) in THF at room temperature can be treated with aqueous LiOH for about 10 hours.

Compounds of formula Ia and Ib include compounds of formula Ia' and Ia'. Compounds of formula Ib include compounds of formula Ib' and Ib". Representative compounds of formulas Ia and Ib include:

(3R,4R,5S)-4-(acetylamino)-5-allyl-3-isopropoxy-1-cyclohexene-1-carboxylic acid;

(3R,4R,5S)-4-(acetylamino)-5-allyl-3-(1-ethylpropoxy)-1-cyclohexene-1-carboxylic acid;

(3R,4R,5R)-4-(acetylamino)-3-isopropoxy-5-(2-oxiranylmethyl)-1-cyclohexene-1-carboxylic acid;

(3R,4R,5R)-4-(acetylamino)-3-(1-ethylpropoxy)-5-(2-oxiranylmethyl)-1-cyclohexene-1-carboxylic acid;

(3R,4R,5R)-4-(acetylamino)-5-(2,3-dihydroxypropyl)-3-(1-ethylpropoxy)-1-cyclohexene-1-carboxylic acid;

(3R,4R,5R)-4-(acetylamino)-5-(3-azido-2-hydroxypropyl)-3-(1-ethylpropoxy)-1-cyclohexene-1-carboxylic acid;

[(1R,5R,6R)-6-(acetylamino)-5-(1-ethylpropoxy)-3-(methoxycarbonyl)-3-cyclohexen-1-yl]acetic acid;

(3R,4R,5R)-4-(acetylamino)-3-(1-ethylpropoxy)-5-(2-oxoethyl)-1-cyclohexene-1-carboxylic acid;

(3R,4R,5R)-4-(acetylamino)-5-(2-hydroxyethyl)-3-isopropoxy-1-cyclohexene-1-carboxylic acid;

(3R,4R,5R)-4-(acetylamino)-3-isopropoxy-5-(2-methoxy-2-oxoethyl)-1-cyclohexene-1-carboxylic acid;

(3R,4R,5R)-4-(acetylamino)-3-isopropoxy-5-isopropyl-1-cyclohexene-1-carboxylic acid;

(3R,4R,5R)-4-(acetylamino)-3-isopropoxy-5-vinyl-1-cyclohexene-1-carboxylic acid;

(3R,4R,5R)-4-(acetylamino)-5-hydroxy-3-isopropoxy-1-cyclohexene-1-carboxylic acid;

(3R,4R,5R)-4-(acetylamino)-5-(allyloxy)-3-isopropoxy-1-cyclohexene-1-carboxylic acid;

(3R,4R,5R)-4-(acetylamino)-5-(1-ethoxyethoxy)-3-isopropoxy-1-cyclohexene-1-carboxylic acid;

methyl (3R,4S,5S)-4-(acetylamino)-5-hydroxy-3-isopropoxy-5-vinyl-1-cyclohexene-1-carboxylate;

methyl (3R,4R,5S)-4-(acetylamino)-3-isopropoxy-5-vinyl-1-cyclohexene-1-carboxylate;

(3S,4R,5R)-4-(acetylamino)-3-allyl-5-isopropoxy-1-cyclohexene-1-carboxylic acid; and (3S,4R,5R)-4-(acetylamino)-5-isopropoxy-3-vinyl-1-cyclohexene-1-carboxylic acid.

Preferred compounds of formula Ia and Ib are those in which $R_1$ is $—CO_2H$, X is $—N(R*)—C(=O)—$, R* is hydrogen, —R$_2$ is C$_1$–C$_6$ alkyl, R$_{15}$ is —Oalkyl, and Y is C$_2$–C$_5$ alkenyl.

The compounds of the present invention can be used in the form of salts derived from inorganic or organic acids. These salts include but are not limited to the following: acetate, trifluoroacetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid. Other salts include salts with alkali metals or alkaline earth metals, such as sodium, potassium, lithium, calcium or magnesium or with ammonium or N(R)$_4$$^+$ salts (where R is loweralkyl).

In addition, salts of the compounds of this invention with one of the naturally occurring amino acids are also contemplated.

Preferred salts of the compounds of the invention include hydrochloride, methanesulfonate, sulfonate, phosphonate and isethinate.

The compounds of the formula Ia or Ib of this invention can have a substituent which is an acid group (for example, —CO$_2$H, —SO$_3$H, —SO$_2$H, —PO$_3$H$_2$, —PO$_2$H). Compounds of the formula Ia or Ib of this invention having a substituent which is an ester of such an acidic group are also encompassed by this invention. Such esters may serve as prodrugs. The prodrugs of this invention are metabolized in vivo to provide the above-mentioned acidic substituent of the parental compound of formula Ia or Ib. Prodrugs may also serve to increase the solubility of these substances and/or absorption from the gastrointestinal tract. These prodrugs may also serve to increase solubility for intravenous administration of the compounds. Prodrugs may also serve to increase the hydrophobicity of the compounds. Prodrugs may also serve to increase the oral bioavailability of the compounds by increasing absorption and/or decreasing first-pass metabolism. Prodrugs may also serve to increase tissue penetration of the compounds, thereby leading to increased activity in infected tissues and/or reduced rate of clearance.

Such esters contemplated by this invention include:

alkyl esters, especially loweralkyl esters, including, but not limited to, ethyl, n-propyl, isopropyl, n-butyl, sec-butyl, isobutyl, t-butyl, n-pentyl esters and the like;

alkoxyalkyl esters, especially, loweralkoxyloweralkyl esters, including, but not limited to, methoxymethyl, 1-ethoxyethyl, 2-methoxyethyl, isopropoxymethyl, t-butoxymethyl esters and the like;

alkoxyalkoxyalkyl esters, especially, alkoxyalkoxy-substituted loweralkyl esters, including, but not limited to, 2-methoxyethoxymethyl esters and the like;

aryloxyalkyl esters, especially, aryloxy-substituted loweralkyl esters, including, but not limited to, phenoxymethyl esters and the like, wherein the aryl group is unsubstituted or substituted as previously defined herein;

haloalkoxyalkyl esters, especially, haloalkoxy-substituted loweralkyl esters, including, but not limited to, 2,2,2-trichloroethoxymethyl esters and the like;

alkoxycarbonylalkyl esters, especially, loweralkoxycarbonyl-substituted loweralkyl esters, including, but not limited to, methoxycarbonylmethyl esters and the like;

cyanoalkyl esters, especially, cyano-substituted loweralkyl esters, including, but not limited to, cyanomethyl, 2-cyanoethyl esters and the like;

thioalkoxymethyl esters, especially, lowerthioalkoxy-substituted methyl esters, including, but not limited to, methylthiomethyl, ethylthiomethyl esters and the like;

alkylsulfonylalkyl esters, especially, loweralkylsulfonyl-substituted loweralkyl esters, including, but not limited to, 2-methanesulfonylethyl esters and the like;

arylsulfonylalkyl esters, especially, arylsulfonyl-substituted loweralkyl esters, including, but not limited to, 2-benzenesulfonylethyl and 2-toluenesulfonylethyl esters and the like;

acyloxyalkyl esters, especially, loweralkylacyloxy-substituted loweralkyl esters, including, but not limited to, formyloxymethyl, acetoxymethyl, pivaloyloxymethyl, acetoxyethyl, pivaloyloxyethyl esters and the like;

cycloalkylcarbonyloxyalkyl esters including, but not limited to, cyclopentanecarbonyloxymethyl, cyclohexanecarbonyloxymethyl, cyclopentanecarbonyloxyethyl, cyclohexanecarbonyloxyethyl esters and the like;

arylcarbonyloxyalkyl esters including, but not limited to, benzoyloxymethyl esters and the like;

(alkoxycarbonyloxy)alkyl esters, especially, (loweralkoxycarbonyloxy)-substituted loweralkyl esters, including, but not limited to, methoxycarbonyloxymethyl, ethoxycarbonyloxymethyl, 1-(methoxycarbonyloxy)ethyl, 2-(ethoxycarbonyloxy)ethyl esters and the like;

(cycloalkyloxycarbonyloxy)alkyl esters, especially, (cycloalkyloxycarbonyloxy)-substituted loweralkyl esters, including, but not limited to, cyclohexyloxycarbonyloxymethyl, cyclopentyloxycarbonyloxyethyl, cyclohexyloxycarbonyloxypropyl esters and the like;

oxodioxolenylmethyl esters including, but not limited to, (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-tluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, (5-butyl-2-oxo-1,3-dioxolen-4-yl)methyl esters and the like;

phthalidyl esters wherein the phenyl ring of the phthalidyl group is unsubstituted or substituted as defined previously herein, including, but not limited to, phthalidyl, dimethylphthalidyl, dimethoxyphthalidyl esters and the like;

aryl esters including, but not limited to, phenyl, naphthyl, indanyl esters and the like;

arylalkyl esters, especially, aryl-substitued loweralkyl esters, including, but not limited to, benzyl, phenethyl, 3-phenylpropyl, naphthylmethyl esters and the like, wherein the aryl part of the arylalkyl group is unsubstituted or substituted as previously defined herein;

dialkylaminoalkyl esters, especially dialkylamino-substituted loweralkyl esters, including, but not limited to, 2-(N,N-dimethylamino)ethyl, 2-(N,N-diethylamino)ethyl ester and the like (heterocyclic)alkyl esters, especially, heterocyclic-substituted loweralkyl esters wherein the heterocycle is a nitrogen-containing heterocycle, including, but not limited to, (heterocyclic)methyl esters and the like, wherein the heterocyclic part of the (heterocyclic)alkyl group is unsubstituted or substituted as previously defined herein; and carboxyalkyl esters, especially, carboxy-substituted loweralkyl esters, including, but not limited to carboxymethyl esters and the like;

and the like.

Preferred prodrug esters of acid-containing compounds of the Formula Ia or Ib are loweralkyl esters, including, but not limited to, ethyl, n-propyl,-isopropyl, n-butyl, sec-butyl, isobutyl, t-butyl, n-pentyl esters, 3-pentyl esters, cycloalkyl esters, cycloalkylalkyl esters and benzyl esters wherein the phenyl ring is unsubstituted or substituted as previously defined herein.

Methods for the preparation of prodrug esters of compounds of the Formula Ia or Ib are well-known in the art and include:

reacting the acid with the corresponding halide (for example, chloride or acyl chloride) and a base (for example, triethylamine, DBU, N,N-dimethylaminopyridine and the like) in an inert solvent (for example, DMF, acetonitrile, N-methylpyrrolidone and the like);

reacting an activated derivative of the acid (for example, an acid chloride, sulfonyl chloride, monochlorophosphonate and the like) with the corresponding alcohol or alkoxide salt; and the like.

Other examples of prodrugs of the present invention include amides derived from the substituent which is an acid group.

Such amides contemplated by this invention include:

simple amides, such as —C(O)NH$_2$ and the like;

alkylamino amides, especially, loweralkylamino amides, including, but not limited to, methylamino, ethylamino, n-propylamino, isopropylamino amides and the like;

cylcoalkylamino amides, including, but not limited to, cylopropylamino, cylcobutylamino, cyclopentylamino, cyclohexylamino amides and the like;

acylamino amides, including, but not limited to acetylamino, propionylamino, butanoylamino amides and the like;

cylcoalkylcarbonylamino amides, including, but not limited to, cyclopropylcarbonylamino, cyclobutylcarbonylamino amides and the like;

alkoxycarbonylalkylamino amides, including, but not limited to, ethoxycarbonylmethylamino, t-butyloxycarbonylmethylamino and the like;

aminoacylamino amides, including, but not limited to, aminoacetylamino amides and the like;

dialkylaminoacylamino amides, including, but not limited to, dimethylaminoacetylamino, diethylaminoacetylamino amides and the like;

(heterocyclic)acylamino amides, including, but not limited to, piperidin-1-ylacetylamino amides and the like;

amides derived from single naturally occuring L-amino acids (or from acid-protected L-amino acids, for example, esters of such amino acids and the like) or from dipeptides comprising two naturally occuring L-amino acids wherein each of the two amino acids is the same or is different (or from acid-protected dipeptides, for example, esters of such dipeptides and the like);

and the like.

Methods for preparation of prodrug amides of compounds of the invention are well-known in the art and include reacting the acid with the appropriate amine in the presence of an amide bond or peptide bond-forming coupling reagent or reacting an activated derivative of the acid with the appropriate amine and the like.

Other examples of prodrugs of the present invention include esters of hydroxyl-substituted compounds of formula Ia and Ib which have been acylated with a blocked or unblocked amino acid residue, a phosphate function, a hemisuccinate residue, an acyl residue of the formula $R^{100}C(O)$— or $R^{100}C(S)$— wherein $R^{100}$ is hydrogen, lower alkyl, haloalkyl, alkoxy, thioalkoxy, alkoxyalkyl, thioalkoxyalkyl or haloalkoxy, or an acyl residue of the formula $R^a$—$C(R^b)(R^d)$—$C(O)$— or $R^a$—$C(R^b)(R^d)$—$C(S)$— wherein $R^b$ and $R^d$ are independently selected from hydrogen or lower alkyl and $R^a$ is —$N(R^e)(R^f)$, —$OR^e$ or —$SR^e$ wherein $R^e$ and $R^f$ are independently selected from hydrogen, lower alkyl and haloalkyl, or an amino-acyl residue having the formula $R^{101}NH(CH_2)_2NHCH_2C(O)$— or $R^{101}NH(CH_2)_2OCH_2C(O)$— wherein $R^{101}$ is hydrogen, lower alkyl, (aryl)alkyl, (cycloalkyl)alkyl, acyl, benzoyl or an -amino acyl group. The amino acid esters of particular interest are of glycine and lysine; however, other amino acid residues can also be used, including any of the naturally occuring amino acids and also including those wherein the amino acyl group is —$C(O)CH_2NR^{102}R^{103}$ wherein $R^{102}$ and $R^{103}$ are independently selected from hydrogen and lower alkyl, or the group —$NR^{102}R^{103}$, where $R^{102}$ and $R^{103}$, taken together, forms a nitrogen containing heterocyclic ring.

Other prodrugs include a hydroxyl-substituted compound of formula Ia and Ib wherein the hydroxyl group is functionalized with a substituent of the formula —$CH(R^{104})OC(O)R^{105}$ or —$CH(R^{104})OC(S)R^{105}$ wherein $R^{105}$ is lower alkyl, haloalkyl, alkoxy, thioalkoxy or haloalkoxy and $R^{104}$ is hydrogen, lower alkyl, haloalkyl, alkoxycarbonyl, aminocarbonyl, alkylaminocarbonyl or dialkylaminocarbonyl. Such prodrugs can be prepared according to the procedure of Schreiber (*Tetrahedron Lett.* 1983, 24, 2363) by ozonolysis of the corresponding methallyl ether in methanol followed by treatment with acetic anhydride.

The preparation of esters of hydroxyl-substituted compounds of formula Ia and Ib is carried out by reacting a hydroxyl-substituted compound of formula formula Ia or Ib with an activated amino acyl, phosphoryl, hemisuccinyl or acyl derivative.

Prodrugs of hydroxyl-substituted-compounds of the invention can also be prepared by alkylation of the hydroxyl substituted compound of formula formula Ia or Ib with (halo)alkyl esters, transacetalization with bis-(alkanoyl) acetals or condensation of the hydroxyl group with an activated aldehyde followed by acylation of the intermediate hemiacetal.

In preparing prodrugs it often is necessary to protect other reactive functional groups, in order to prevent unwanted side reactions. After protection of the reactive groups the desired group can be functionalized. The resulting functionalized product is then deprotected, to remove the protecting groups that were added to prevent unwanted side reactions. This will provide the desired prodrug. Suitable reaction conditions for preparing protecting groups are well known in the art. One source for reaction conditions is found in T. H. Greene and P. G. M. Wuts, *Protective Groups in Organic Synthesis,* 2nd edition, John Wiley & Sons, New York (1991).

This invention also encompasses compounds of the Formula Ia or Ib which are esters or prodrugs and which are also salts. For example, a compound of the invention can be an ester of a carboxylic acid and also an acid addition salt of an amine or nitrogen-containing substituent in the same compound.

The compounds of the present invention are useful for inhibiting neuraminidase from disease-causing microorganisms which comprise a neuraminidase. The compounds of the invention are useful (in humans, other mammals and fowl) for treating or preventing diseases caused by microorganisms which comprise a neuraminidase.

The compounds of the present invention are useful for inhibiting influenza A virus neuraminidase and influenza B virus neuraminidase, in vitro or in vivo (especially in mammals and, in particular, in humans). The compounds of the present invention are also useful for the inhibition of influenza viruses, orthomyxoviruses, and paramyxoviruses in vivo, especially the inhibition of influenza A viruses and influenza B viruses in humans and other mammals. The compounds of the present invention are also useful for the treatment of infections caused by influenza viruses, orthomyxoviruses, and paramyxoviruses in vivo, especially the human diseases caused by influenza A and influenza B viruses.

The compounds of the present invention are also useful for the prophylaxis of infections caused by influenza viruses, orthomyxoviruses, and paramyxoviruses in vivo in humans and other mammals, especially the prophylaxis of influenza A and influenza B viral infections; and, in particular, the prophylaxis of influenza A and influenza B viral infections in human subjects who are at high risk of developing other respiratory diseases concurrent with or as a consequence of influenza virus infections, or who suffer from chronic respiratory illness, such as asthma, emphysema, or cystic fibrosis.

Total daily dose administered to a human or other mammal host in single or divided doses may be in amounts, for example, from 0.001 to 300 mg/kg body weight daily and more usually 0.1 to 10 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

Administration of a compound of this invention will begin before or at the time of infection or after the appearance of established symptoms and/or the confirmation of infection.

The compounds of the present invention may be administered orally, parenterally, sublingually, intranasally, by intrapulmonary administration, by inhalation or insufflation as a solution, suspension or dry powder (for example, in a spray), or rectally, in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

While the compounds of the invention can be administered as the sole active pharmaceutical agent, they can also be used in combination with one or more anti-infective agents and/or other agents used to treat other acute or chronic respiratory ailments. Other agents to be administered in combination with a compound of the present invention include: an influenza vaccine; other influenza inhibitors such as, for example, amantadine, rimantadine, ribavirin, and the like; another influenza neuraminidase inhibitor, such as, for example, zanamivir or GS 4104 and the like; agents used to treat respiratory bacterial infections and bronchitis, such as, for example, erythromycin, clarithromycin, azithromycin and the like; and agents used to treat asthma, such as, for example, zileuton, albuterol (salbutamol), salmeterol, formoterol, ipratropium bromide, inhaled steroids and the like, or anti-inflammatory agents for treating asthma such as, for example, beclomethasone dipropionate, fluticasone propionate, budesonide, triamcinolone acetonide, flunisolide, cromolyn, zafirlukast, montelukast used in combination with a compound of the present invention. When administered as a combination, the therapeutic agents can be formulated as separate compositions which are given at the same time or different times, or the therapeutic agents can be given as a single composition.

The ability of the compounds of the invention to inhibit neuraminidase in vitro can be determined according to the method described below.

Neuraminidase Inhibition Assay

Influenza virus A/N1/PR/8/34 was grown in the allantoic cavity of fertilized eggs and purified by sucrose density gradient centrifugation (Laver, W. G. (1969) in "Fundamental Techniques in Virology" (K. Habel and N. P. Salzman, eds.) pp. 92–86, Academic Press, New York). Influenza virus A/N2/Tokyo/3/67 was obtained from the tissue culture supernatents of virus grown on MDCK cells. Neuraminidase from B/Memphis/3/89 virus was prepared by digestion of the virus with TPCK-trypsin followed by centrifugation and then purification of the neuraminidase catalytic fragment using sucrose density gradient centrifugation and dialysis as described previously (Air, G. M., Laver, W. G., Luo, M., Stray, S. J., Legrone, G., and Webster, R. G. (1990) *Virology* 177, 578–587).

The neuraminidase inhibition assays used the neuraminidase enzymatic activity associated with the A/N1/PR/8/34 or A/N2/Tokyo/3/67 whole virus, or the B/Memphis/3/89 catalytic head fragment. The whole virus or catalytic fragment was diluted appropriately with 20 mM N-ethylmorpholine, 10 mM calcium choride, pH 7.5 buffer on the day of the experiment. Neuraminidase inhibition assays were conducted in 20 mM N-ethylmorpholine, 10 mM calcium choride, pH 7.5 buffer with 5% DMSO. Reaction mixtures included neuraminidase, inhibitor (test compound) and 20–30 µM 4-methylumbelliferyl sialic acid substrate in a total volume of 200 µL and were contained in white 96-well U-shaped plates. Typically, five to eight concentrations of inhibitor were used for each Ki value measurement. The reactions were initiated by the addition of enzyme and allowed to proceed for 30–60 minutes at room temperature. The fluorescence for each well of the plate was measured once each minute during the reaction period by a Fluoroskan II plate reader (ICN Biomedical) equipped with excitation and emission filters of 355+/−35 nm and 460+/−25 nm, respectively. The plate reader was under the control of DeltaSoft II software (Biometallics) and a Macintosh computer. If the compound exhibited linear reaction velocities during the reaction period, then the reaction velocities for the dose-response study were fit to equation 1 using a nonlinear regression program (Kaleidagraph) to determine the overall Ki value (Segel, I. H. (1975) in Enzyme Kinetics, pp. 105–106, Wiley-Interscience, New York).

$$(1-Vi/Vo)=[I]/\{[I]+Ki(1+[S]/Km)\} \qquad \text{eqn 1}$$

In equation 1, Vi and Vo represent inhibited and uninhibited reaction velocities, respectively, and Km=16–40 µM depending on the neuraminidase strain tested. For those compounds exhibiting slow-binding inhibition (Morrison, J. F. (1982) *Trends Biochem. Sci.* 7, 102–105), a second experiment was performed in a manner identical to the first except that neuraminidase and inhibitor were preincubated in the absence of substrate for 2 hours at room temperature prior to initiating the reactions with substrate. Data analysis for the resulting linear velocities was conducted as described above.

Equation 2 was used to measure Ki values in the subnanomolar range (Morrison, J. F. And Stone, S. R. (1985) *Comments Mol. Cell Biophys.* 2, 347–368).

$$V=A\{\text{sqrt}\{(Ki'+It-Et)^2+4Ki'Et\}-(Ki'+It-Et)\} \qquad \text{eqn. 2}$$

In equation 2, V=velocity; A=αkcat[S]/2(Km+[S]); α is a factor to convert fluorescence units to molar concentrations; Ki'=Ki(1+[S]/Km); It=total inhibitor concentration and Et=total active concentration of neuraminidase.

The compounds of the invention inhibit influenza A neuraminidase and influenza B neuraminidase with $K_i$ values between about 0.1 nanomolar and about 500 micromolar. Preferred compounds of the invention invention inhibit influenza A neuraminidase and influenza B neuraminidase with $K_i$ values between about 0.1 nanomolar and about 3.5 micromolar.

The ability of the compounds of the invention to inhibit plaque formation in cell culture can be determined by the method described below.

Cell Culture Plaque Formation Inhibition Assay

Cell Cultures: MDCK cells obtained from the American Type Culture Collection were grown in Dulbecco's Modified Eagle Medium (DMEM) high glucose (GibcoBRL) supplemented with 10% fetal calf serum (JRH Biosciences), 40 mM HEPES buffer (GibcoBRL) and antibiotics (GibcoBRL). Cells were routinely cultured in flasks or roller bottles at 37° C. and 5% $CO_2$. At confluence cells were reduced to a density of 500,000 cells in a ml using trypsin/EDTA (GibcoBRL) treatment of the monolayer followed by cell centrifugation, resuspension, and dilution into growth media. Cells were planted at a volume to surface area ratio of 1 ml over 1 $cm^2$ of growth surface.

Plaque Assay Protocol: On MDCK cell confluent 6 well plates growth media was removed and the cells were overlaid with 1.5 ml of assay media (DMEM with 1% fetal calf serum, 40 mM HEPES buffer and antibiotics) containing pre-mixed virus (influenza A/Tokyo/3/67 [H2N2]) (40–100 plaque forming units) and 2× concentration test compound. The plates were placed on a rocker and incubated for 2 hours at room temperature. During the virus adsorption period agar overlay media was prepared. In a microwave oven 2× agarose (final concentration of 0.6% agarose) in overlay media (DMEM with 40 mM HEPES buffer) was melted and then placed in a 48° C. water bath for temperature equilibration. After the virus adsorption period was completed 1.5 ml agar over media was added and mixed with the 1.5 ml virus and test compound containing media per well.

Cultures were incubated at 35° C. for the period required for plaque development, usually several days. Plaques were fixed with 3.7% formalin in PBS for 20 minutes followed by removal of the agar overlay and staining with 0.1% crystal violet in distilled water for 15 minutes. Plaques were counted and EC 50 concentration determined from multiple concentrations of the tested compound using regression analysis.

Viral Stocks: Stocks were prepared in MDCK confluent roller bottles incubated at 37° C. in DMEM supplemented with 1% FCS, 40 mM HEPES buffer, and antibiotics. Bottles were inoculated with a multiplicity of infection of approximately 0.1 plaque forming unit for each cell. Roller bottles were harvested after the cytopathic effect of the virus was observed to be complete. Stocks were prepared from the supernatant resulting from the low speed centrifugation of the media and cell lysate. Stocks were titered and stored at −80° C.

Compounds of the invention provided plaque formation inhibition for influenza virus A/N2/Tokyo in MDCK cells with EC50 values between about 100 micromolar and about 1 nanomolar. Preferred compounds of the invention provided plaque formation inhibition for influenza virus A/N2/Tokyo in MDCK cells with EC50 values between about 1 micromolar and about 1 nanomolar.

The compounds of the invention can be tested for in vivo antiviral activity using the method described below.

In Vivo Antiviral Efficacy Method

Female BALB/c mice were placed under anesthesia (sevoflurane) and inoculated intranasally (IN) with 0.1 ml of influenza A VR-95 (Puerto Rico PR8-34) at $10^{-2}$ (diluted from frozen stock). This viral concentration consistently produced disease in mice within 5 days of inoculation. Animals were treated 4 h. pre-infection and 4 h. post-infection, and periodically thereafter, with one of the following therapies: no treatment; test compound (100, 25, 6.25, 1.39 mg/kg/day BID, PO); or vehicle (sterile water BID, PO). A group of ten animals (designated as control) was inoculated with 0.9% saline. Percent survival was determined. On day five, lungs were harvested, weighed and assigned scores of 0, 1, 2, 3 or 4 based on percentage consolidation (0; 10–20; 25–50; 50–75; 75–100%, respectively). In addition, each lung pair was image analyzed to determine objective lung consolidation percentages.

The following Examples will serve to further illustrate the preparation of the compounds of the invention, without limitation.

EXAMPLES

General. Melting points are uncorrected. NMR spectra were recorded at 400 MHz for $^1$H NMR, 100 MHz for $^{13}$C NMR. THF was dried by distillation on sodium benzophenone ketyl, dichloromethane, benzene, toluene and triethylamine on calcium hydride. DBU was distilled under vacuum, then stored over 4 Å Linde molecular sieves.

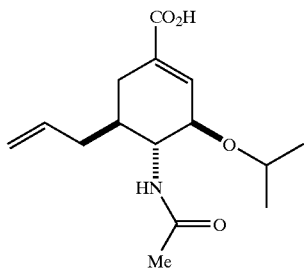

Example 1

(3R,4R,5S)-4-(acetylamino)-5-allyl-3-isopropoxy-1-cyclohexene-1-carboxylic acid

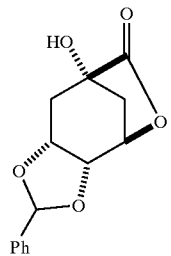

Example 1A (1R,2R,6R,8S)-8-hydroxy-4-phenyl-3,5,10-trioxatricyclo[6.2.1.0$^{2,6}$]undecan-9-one The procedure in J. Org. Chem. 1995, 50, 888–890 was followed. Briefly, a solution of quinic acid (20.0 g, 0.104 mol), benzaldehyde (16.6 g, 156 mmol) and para-toluenesulfonic acid monohydrate (1.0 g, 5.26 mmol) in toluene (350 mL) was refluxed for 10 hours in a flask equipped with a Dean-Stark trap. The reaction mixture was cooled, washed with saturated NaHCO$_3$ solution and brine, dried (MgSO$_4$). Filtered and concentrated. The concentrate was dissolved in 1:1 hexanes/ethyl acetate (100 mL) and cooled to −20° C. for 2 hours to provide 10.8 g (40%) of the desired product.

Purification of the mother liquor by flash chromatography (hexanes/ethyl acetate 3:2) gave 12.1 g (44%) of a 3:1 mixture of the diastereomers of Example 2.

m.p. 96–97° C.

$[\alpha]^P_{295}$ +5.43° (c 0.405, ethyl acetate).

$^1$H NMR (400 MHz, CDCl$_3$): δ7.51–7.44 (m, 5H), 5.76 (s, 1H), 4.81 (m, 1H), 4.55 (m, 1H), 4.38 (m, 1H), 3.20 (s, br., 1H), 2.78 (d, J=11.9 Hz, 1H), 2.46 (m, 1H), 2.38 (m, 2H).

$^{13}$C NMR (100.6 MHz, CDCl$_3$): δ178.88, 135.27, 129.82, 128.49, 126.51, 103.63, 75.48, 72.85, 72.58, 71.36, 37.51, 34.24.

HRMS (FAB/NBA): calcd (M+H)$^+$ for C$_{14}$H$_{15}$O$_5$: 263.09195. Found: 263.09260.

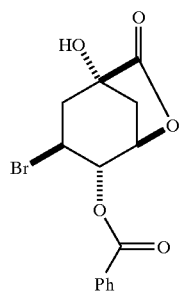

Example 1B (1R,3S,4S,5R)-3-bromo-1-hydroxy-7-oxo-6-oxabicyclo[3.2.1]oct-4-yl benzoate The procedure in J. Am. Chem. Soc. 1986, 108, 8068–8071 was followed. Briefly, a solution of Example 1A (10.0 g, 38.1 mmol), N-bromosuccinimide (9.5 g, 53.4 mmol) and AIBN (50 mg, 0.3 mmol) in benzene (200 mL) was refluxed for 4 hours. The reaction mixture was cooled to room temperature, washed with 20% aqueous $NaHSO_3$, saturated $Na_2CO_3$, and brine, dried ($MgSO_4$), filtered and concentrated. The concentrate was purified by flash column chromatography on silica gel using hexanes/ethyl acetate (3/2) to afford 10.1 g (80%) of the desired product as a white solid.

m.p. 142–143° C.

$[\alpha]^P{}_{295}$ +54.93° (c 0.730, ethyl acetate).

$^1$H NMR (400 MHz, $CDCl_3$): δ8.05–7.47 (m, 5H), 5.65 (d, J=3.8 Hz, 1H), 5.02 (m, 1H), 4.49 (m, 1H), 3.61 (s, br. 1H), 2.78 (m, 1H), 2.55 (m, 3H).

$^{13}$C NMR (100.6 MHz, $CDCl_3$): δ177.71, 164.37, 133.96, 129.69, 128.64, 128.32, 74.67, 71.20, 70.58, 41.78, 40.51, 37.46.

HRMS (FAB/NBA): calcd $(M+H)^+$ for $C_{14}H_{14}O_5Br$: 341.00247. Found: 341.00300.

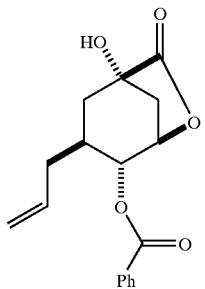

Example 1C (1S,3S,4R,5R)-3-allyl-1-hydroxy-7-oxo-6-oxabicyclo[3.2.1]oct-4-yl benzoate A solution of Example 1B (5.3 g, 16.1 mmol), allyltributyltin (8.0 g, 24.2 mmol) and AIBN (1.0 g, 6.1 mmol) in benzene (100 mL) was refluxed for 10 hours. The solution was concentrated and diluted with dichloromethane (100 mL). A 10% aqueous solution of $KF·2H_2O$ (50 mL) was added, and the mixture was stirred for 2 hours. A white precipitate formed and was filtered off. The organic phase was separated, dried ($MgSO_4$), filtered and concentrated. The concentrate was purified by flash column chromatography on silica gel using hexanes/ethyl acetate (2/3) to afford 4.0 g (82%) of the desired product as a colorless oil.

$[\alpha]^P{}_{295}$ +2.60° (c 0.730, ethyl acetate).

$^1$H NMR (400 MHz, $CDCl_3$): δ8.06–7.45 (m, 5H), 5.71 (m, 1H), 5.20–4.91 (m, 4H), 3.25 (s, br., 1H), 2.57–2.14 (m, 6H), 1.90 (m, 1H).

$^{13}$C NMR (100.6 MHz, $CDCl_3$): δ178.83, 165.08, 135.26, 133.51, 129.54, 129.18, 128.49, 118.11, 75.47, 71.90, 70.09, 38.54, 37.15, 36.36, 35.83.

HRMS (FAB/NBA): calcd $(M+H)^+$ for $C_{17}H_{19}O_5$: 303.12326. Found: 303.12170.

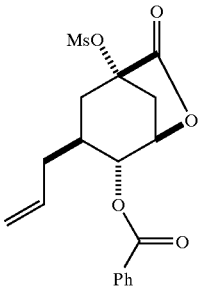

Example 1D (1S,3S,4R,5R)-3-allyl-1-[(methylsulfonyl)oxy]-7-oxo-6-oxabicyclo[3.2.1]oct-4-yl benzoate Methanesulfonyl chloride (4.6 mL, 59.4 mmol) was slowly added to a 0° C. solution of compound Example 1C (10.0 g, 33.1 mmol) and triethylamine (9.2 mL, 66.1 mmol) in dichloromethane (200 mL). The reaction mixture was stirred for 2 hours, and filtered. The resulting solid was washed with dichloromethane and discarded. The combined filtrates were washed with saturated $NaHCO_3$ solution and brine, dried ($MgSO_4$), filtered, and concentrated. The concentrate was purified by flash column chromatography on silica gel using hexanes/ethyl acetate (3/2) to afford 12.6 g (100%) of the desired product as a colorless oil.

$[\alpha]^P{}_{295}$ +3.33° (c 0.330, ethyl acetate).

$^1$H NMR (400 MHz, $CDCl_3$): δ8.03–7.46 (m, 5H), 5.69 (m, 1H), 5.18 (m, 3H), 4.98 (m, 1H), 3.28 (s, 3H), 3.24 (m, 1H), 2.84 (d, J=11.6 Hz, 1H), 2.49 (m, 3H), 2.15 (m, 2H).

$^{13}$C NMR (100.6 MHz, $CDCl_3$): δ172.31, 164.92, 134.83, 133.65, 129.57, 128.92, 128.54, 118.57, 82.62, 75.48, 69.58, 40.96, 38.24, 36.44, 36.12, 33.51.

HRMS (FAB/NBA): calcd $(M+H)^+$ for $C_{18}H_{21}O_7S$: 381.1008. Found: 381.1019.

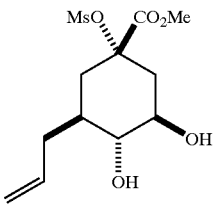

Example 1E methyl (1S,3S,4R,5R)-3-allyl-4,5-dihydroxy-1-[(methylsulfonyl)oxy]cyclohexanecarboxylate Potassium carbonate (100 mg, 0.72 mmol) was added to a solution of Example 1D (2.0 g, 5.3 mmol) in methanol (30 mL). The reaction mixture was stirred for 30 minutes at room temperature, filtered and concentrated. The concentrate was purified by flash column chromatography on silica gel using ethyl acetate to afford 1.6 g (99%) of the desired product as a colorless oil.

$[\alpha]^P{}_{295}$ +3.27° (c 0.275, ethyl acetate).

$^1$H NMR (400 MHz, $CDCl_3$): δ5.77 (m, 1H), 5.05 (m, 2H), 3.81 (m, 1H), 3.79 (s, 3H), 3.17 (m, 1H), 3.15 (s, 3H), 2.59 (m, 2H), 2.29 (m, 1H), 1.94 (m, 3H), 1.58 (m, 1H).

$^{13}$C NMR (100.6 MHz, $CDCl_3$): δ170.66, 135.19, 117.44, 87.90, 77.35, 70.43, 53.00, 40.43, 39.42, 37.45, 36.54, 35.39.

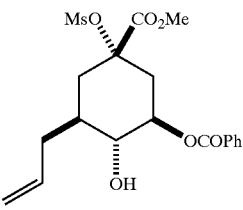

Example 1F (1R,2R,3S,5S)-3-allyl-2-hydroxy-5-(methoxycarbonyl)-5-[(methylsulfonyl)oxy] cyclohexyl benzoate Benzoyl chloride (2.3 mL, 19.8 mmol) was added dropwise to a 0° C. solution of Example 1E (6.1 g, 19.8 mmol) and pyridine (3.2 mL, 39.6 mmol) in dichloromethane (100 mL). The reaction mixture was stirred for 5 hours, washed with aqueous HCl (2N), saturated NaHCO$_3$ solution, and brine, dried (MgSO$_4$), filtered and concentrated. The concentrate was purified by flash column chromatography on silica gel using hexanes/ethyl acetate (3/2) to afford 6.9 g (85%) of the desired product as a white solid.

m.p. 46–47° C.

$[\alpha]^P_{295}$ +1.10° (c 0.455, ethyl acetate).

$^1$H NMR (400 MHz, CDCl$_3$): δ8.01–7.38 (m, 5H), 5.76 (m, 1H), 5.22 (m, 1H), 5.10 (m, 2H), 3.78 (s, 3H), 3.53 (m, 1H), 3.23 (s, 3H), 2.80 (m, 1H), 2.57 (m, 1H), 2.40 (m, 1H), 2.11 (m, 3H), 1.64 (m, 1H).

$^{13}$C NMR (100.6 MHz, CDCl$_3$): δ170.37, 166.34, 134.82, 133.25, 129.59, 129.46, 128.32, 117.72, 86.88, 74.67, 74.10, 53.04, 40.50, 37.13, 36.97, 36.47, 35.22.

HRMS (FAB/NBA): calcd (M+H)$^+$ for C$_{19}$H$_{25}$O$_8$S: 413.127015. Found: 413.124845.

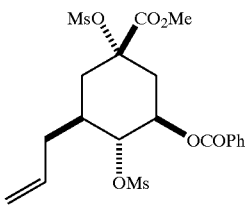

Example 1G (1R,2R,3S,5S)-3-allyl-5-(methoxycarbonyl)-2,5-bis[(methylsulfonyl)oxy]cyclohexyl benzoate Methanesulfonyl chloride (1.4 mL, 18.1 mmol) was added dropwise to a 0° C. solution of Example 1F (5.0 g, 12.6 mmol) and triethylamine (5.0 mL, 35.9 mmol) in dichloromethane (80 mL). The reaction mixture was stirred for 10 hours, washed with saturated NaHCO$_3$ solution, brine, dried (MgSO$_4$). Filtered and concentrated. The concentrate was purified by flash column chromatography on silica gel using hexanes/ethyl acetate (3/1) to afford 5.9 g (100%) of the desired product as a white solid.

m.p. 154–155° C.

$[\alpha]^P_{295}$ +20.00° (c 0.500, chloroform).

$^1$H NMR (400 MHz, CDCl$_3$): δ8.10–7.48 (m, 5H), 5.77 (m, 1H), 5.47 (m, 1H), 5.18 (m, 2H), 4.79 (m, 1H), 3.82 (s, 3H), 3.23 (s, 3H), 2.94 (m, 1H), 2.90 (s, 3H), 2.58 (m, 2H), 2.41 (m, 1H), 2.18 (m, 2H), 1.78 (m, 1H).

$^{13}$C NMR (100.6 MHz, CDCl$_3$): δ169.79, 165.24, 133.53, 133.32, 129.77, 128.97, 128.50, 118.89, 85.88, 82.74, 70.64, 53.20, 40.57, 38.88, 37.25, 37.00, 35.35, 35.05.

HRMS (FAB/NBA): calcd (M+H)$^+$ for C$_{20}$H$_{27}$O$_{10}$S$_2$: 491.10455. Found: 491.10600.

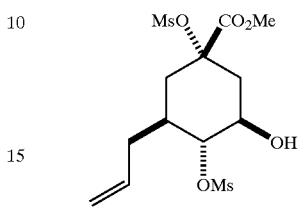

Example 1H methyl (1S,3S,4R,5R)-3-allyl-5-hydroxy-1,4-bis[(methylsulfonyl)oxy]cyclohexanecarboxylate Potassium carbonate (80 mg, 0.58 mmol) was added to a solution of Example 1G (2.0 g, 4.1 mmol) in methanol (40 mL). The reaction mixture was stirred for 30 minutes at room temperature, acidified to pH 5–6 with DOWEX® 50WX2-200 ion-exchange resin, filtered and concentrated. The concentrate was purified by flash column chromatography on silica gel using hexanes/ethyl acetate (1:1) to afford 1.26 g (80%) of the desired product as a colorless oil.

$[\alpha]^P_{295}$ +9.88° (c 0.405, chloroform).

$^1$H NMR (400 MHz, CDCl$_3$): δ5.74 (m, 1H), 5.14 (m, 2H), 4.38 (m, 1H), 4.14 (m, 1H), 3.82 (s, 3H), 3.18 (ss, 6H), 2.75 (m, 1H), 2.53 (m, 1H), 2.43 (m, 1H), 2.22 (m, 1H), 2.09 (m, 2H), 1.70 (m, 1H).

$^{13}$C NMR (100.6 MHz, CDCl$_3$): δ170.13, 133.73, 118.46, 87.12, 86.63, 68.32, 53.18, 40.44, 40.14, 38.57, 37.28, 35.10, 35.05.

HRMS (FAB/NBA): calcd (M+H)$^+$ for C$_{13}$H$_{23}$O$_9$S$_2$: 387.07834. Found: 387.07900.

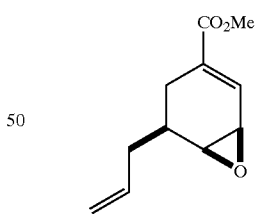

Example 1I methyl (1R,5S,6S)-5-allyl-7-oxabicyclo[4.1.0]hept-2-ene-3-carboxylate A solution of Example 1H (3.4 mg, 8.8 mmol) and DBU (2.9 mL, 19.4 mmol) in THF (60 mL) was refluxed for 6 hours, washed with brine, dried (MgSO$_4$), filtered and concentrated. The concentrate was passed through a short silica gel column using hexanes/ethyl acetate (4/1) to afford the desired product.

¹H NMR (400 MHz, CDCl₃): δ7.07 (m, 1H), 5.88 (m, 1H), 5.19 (m, 2H), 3.75 (s, 3H), 3.49 (m, 1H), 3.42 (m, 1H), 2.59 (m, 1H), 2.39 (m, 2H), 1.84 (m, 2H).

¹³C NMR (100.6 MHz, CDCl₃): δ165.94, 134.49, 129.56, 117.99, 78.48, 57.56, 52.13, 39.26, 38.39, 34.26, 33.52, 26.16.

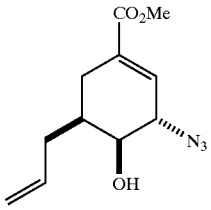

Example 1J methyl (3S,4S,5S)-5-allyl-3-azido-4-hydroxy-1-cyclohexene-1-carboxylate A solution of Example 1I, sodium azide (2.8 g, 43.1 mmol) and NH₄Cl (1.0 g, 18.8 mL) in methanol (30 mL) and H₂O (10 mL) was refluxed for 5 hours, diluted with H₂O and extracted with ethyl acetate. The combined ethyl acetate layers were dried (MgSO₄), filtered, and concentrated. The concentrate was purified by flash column chromatography on silica gel using hexanes/ethyl acetate (1/1) to afford 1.4 g (67% over steps I and J) of the desired product as a colorless oil.

$[\alpha]^P_{295}$ +233.45° (c 0.290, chloroform).

¹H NMR (400 MHz, CDCl₃): δ6.82 (m, 1H), 5.81 (m, 1H), 5.11 (m, 2H), 3.99 (m, 1H), 3.89 (m, 1H), 3.78 (s, 3H), 2.50–2.05 (m, 4H), 1.93 (m, 1H).

¹³C NMR (100.6 MHz, CDCl₃): δ166.42, 135.85, 134.11, 130.90, 117.08, 70.43, 60.30, 51.98, 34.61, 34.16, 26.10.

FT-IR: 2097.8 cm⁻¹, 1715.4 cm⁻¹.

HRMS (FAB/NBA): calcd (M+H)⁺ for C₁₁H₁₆O₃N₃: 238.11917. Found: 238.12010.

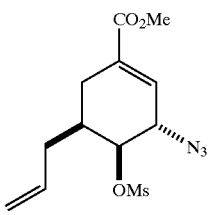

Example 1K methyl (3S,4S,5S)-5-allyl-3-azido-4-[(methylsulfonyl)oxy]-1-cyclohexene-1-carboxylate Methanesulfonyl chloride (0.7 mL, 9.0 mmol) was added dropwise to a 0° C. solution of Example 1J (1.45 g, 6.1 mmol) and triethylamine (2.5 mL, 18.0 mmol) in dichloromethane (40 mL). The reaction mixture was stirred for 2 hours, washed with saturated NaHCO₃ solution, brine, dried (MgSO₄), filtered and concentrated. The concentrate was purified by flash column chromatography on silica gel using hexanes/ethyl acetate (3/1) to afford 1.48 g (78%) of the desired product as a white solid.

m.p. 70–72° C.

$[\alpha]^P_{295}$ +120.54° (c 0.185, chloroform).

¹H NMR (400 MHz, CDCl₃): δ6.82 (m, 1H), 5.79 (m, 1H), 5.16 (m, 2H), 4.77 (m, 1H), 4.34 (m, 1H), 3.80 (s, 3H), 3.08 (s, 3H), 2.55 (m, 1H), 2.24 (m, 4H).

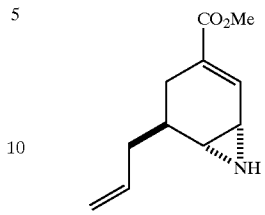

Example 1L methyl (1S,5S,6R)-5-allyl-7-azabicyclo[4.1.0]hept-2-ene-3-carboxylate Triphenylphosphine (1.14 g, 4.35 mmol) was slowly added to a room temperature solution of Example 1K (0.80 g, 2.54 mmol) in THF (30 mL). After stirring for 2 hours, water (3.0 mL) and triethylamine (1.0 mL, 7.19 mmol) were added. The mixture was stirred for 10 hours, and concentrated. The concentrate was chromatographed on silica gel using ethyl acetate to afford the desired product with Ph₃P as a contaminant.

¹H NMR (400 MHz, CDCl₃): δ7.7–7.4 (m, Ph₃P), 7.21 (m, 1H), 5.80 (m, 1H), 5.06 (m, 2H), 3.73 (s, 3H), 2.50 (m, 4H), 1.95 (m, 3H).

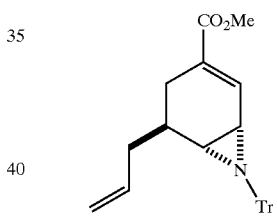

Example 1M methyl (1S,5S,6R)-5-allyl-7-trityl-7-azabicyclo[4.1.0]hept-2-ene-3-carboxylate Trityl chloride (0.85 g, 3.05 mmol) was added to a 0° C. solution of Example 1L and triethylamine (0.5 mL, 3.59 mmol) in dichloromethane (30 mL). After stirring for 2 hours at 0° C., the reaction mixture was concentrated. The concentrate was purified by flash chromatography on silica gel using hexanes/ethyl acetate (10/1) to afford 1.02 g (92%, over steps L and M) of the desired product as a white solid.

m.p. 58–60° C.

$[\alpha]^P_{295}$ −88.55° (c 0.585, chloroform).

¹H NMR (400 MHz, CDCl₃): δ7.47–7.21 (m, 16H), 5.72 (m, 1H), 4.95 (m, 2H), 3.80 (s, 3H), 2.72 (m, 2H), 2.50 (m, 1H), 1.86–1.65 (m, 4H).

¹³C NMR (100.6 MHz, CDCl₃): δ167.48, 144.60, 137.60, 136.44, 129.50, 129.19, 127.44, 126.65, 116.24, 74.09, 51.67, 39.73, 35.54, 29.75, 28.09, 25.06.

HRMS (FAB/NBA): calcd (M+H)+ for C30H30O2N: 436.22766. Found: 436.22850.

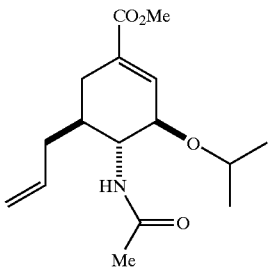

Example 1N methyl (3R,4R,5S)-4-(acetylamino)-5-allyl-3-isopropoxy-1-cyclohexene-1-carboxylate Boron trifluoride etherate (87 µL, 0.69 mmol) was added to a solution of Example 1M (0.200 g, 0.46 mmol) in isopropanol (10 mL). After stirring for 2 hours at 70–80° C., the reaction mixture was concentrated.

The concentrate was dissolved in dry pyridine (1.5 mL) and treated with acetic anhydride (15 mL, 159 mmol). The reaction mixture was stirred at room temperature for 12 hours and concentrated.

The concentrate was dissolved in ethyl acetate (30 mL), washed with aqueous HCl (2N), saturated NaHCO3 solution, and brine, dried (MgSO4), filtered and concentrated. The concentrate was purified by flash column chromatography on silica gel using hexanes/ethyl acetate (1/5) to afford 110 mg (81%) of the desired product as a white solid.

m.p. 105–106° C.

[α]$^P_{295}$ −27.62° (c 0.525, ethyl acetate).

1H NMR (400 MHz, CDCl3): δ6.76 (m, 1H), 5.76 (m, 1H), 5.48 (d, J=8.2 Hz, 1H), 5.05 (m, 2H), 4.20 (m, 1H), 3.76 (m, 1H), 3.74 (s, 3H), 3.49 (m, 1H), 2.52 (m, 1H), 2.32 (m, 1H), 2.08 (m, 3H), 2.00 (s, 3H), 1.17 (2×d, J=6.1 Hz, 6H).

13C NMR (100.6 MHz, CDCl3): δ170.05, 166.93, 137.85, 135.53, 130.33, 116.99, 74.92, 71.14, 55.32, 51.74, 36.18, 35.95, 29.43, 23.46, 23.00, 22.21.

HRMS (FAB/NBA): calcd (M+H)+ for C16H26O4N: 296.18619. Found: 296.18510.

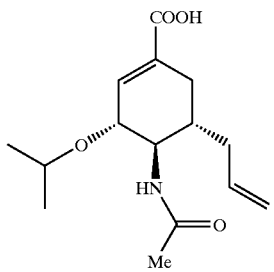

Example 1O (3R,4R,5S)-4-(acetylamino)-5-allyl-3-isopropoxy-1-cyclohexene-1-carboxylic acid Aqueous lithium hydroxide solution (0.1N, 15 mL) was added to a room temperature solution of Example 1N (40 mg, 0.136 mmol) in THF (5 mL). After stirring for 10 hours, the reaction mixture was acidified to pH 5–6 with DOWEX® 50WX2-200 ion-exchange resin, filtered and concentrated. The concentrate was purified by flash chromatography using acetic acid/ethyl acetate (1/5) to afford 34 mg (90%) of the desired product as a white solid.

m.p. 202–203° C.

[α]$^P_{295}$ −11.66° (c 0.180, methanol).

1H NMR (400 MHz, CD3OD): δ6.73 (m, 1H), 5.78 (m., 1H), 5.07 (m, 2H), 4.03 (m, 1H), 3.79 (h, J=6.1 Hz, 1H), 3.66 (m, 1H), 2.54 (m, 1H), 2.30 (m, 1H), 2.01 (m, 2H), 1.99 (s, 3H), 1.87 (m, 1H), 1.15 (2×d, J=6.1 Hz, 6H).

13C NMR (100.6 MHz, CD3OD): δ173.36, 169.99, 139.42, 137.05, 132.03, 117.24, 77.89, 73.47, 55.72, 38.19, 37.46, 31.07, 23.33, 22.82, 22.70.

HRMS (FAB/NBA): calcd (M+H)+ for C15H24O4N 282.17053. Found: 282.16970.

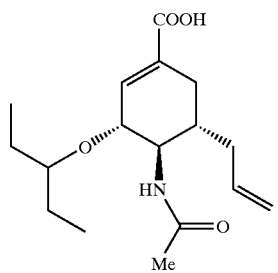

Example 2

(3R,4R,5S)-4-(acetylamino)-5-allyl-3-(1-ethylpropoxy)-1-cyclohexene-1-carboxylic acid

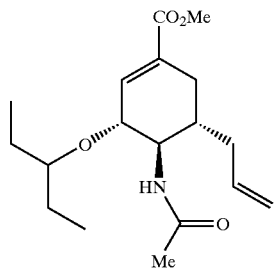

methyl (3R,4R,5S)-4-(acetylamino)-5-allyl-3-(1-ethylpropoxy)-1-cyclohexene-1-carboxylate Boron trifluoride etherate (218 µL, 1.72 mmol) was added to a solution of Example 1M (0.50 g, 1.15 mmol) in 3-pentanol (15 mL). After stirring for 2 hours at 70–80° C., the reaction mixture was concentrated.

The concentrate was dissolved in dry pyridine (1.5 mL) and treated with acetic anhydride (15 mL, 159 mmol). After stirring for 10 hours, the reaction mixture was concentrated.

The concentrate was dissolved in ethyl acetate (30 mL), washed with aqueous HCl (2N), saturated NaHCO3 solution, and brine, dried (MgSO4), filtered and concentrated. The concentrate was purified by flash chromatography on silica gel using hexanes/ethyl acetate (1/5) to afford 315 mg (85%) of the desired product as a white solid.

m.p. 102–103° C.

[α]$^P_{295}$ −41.03° (c 0.290, ethyl acetate).

1H NMR (400 MHz, CDCl3): δ6.77 (m, 1H), 5.76 (m, 1H), 5.46 (d, J=8.4 Hz, 1H), 5.05 (m, 2H), 4.18 (m, 1H), 3.74 (s, 3H), 3.55 (m, 1H), 3.33 (qn, J=5.7 Hz, 1H), 2.48 (m, 1H), 2.31 (m, 1H), 2.07 (m, 3H), 1.99 (s, 3H), 1.49 (m, 4H), 0.90 (m, 6H).

$^{13}$C NMR (100.6 MHz, CDCl$_3$): δ169.99, 167.00, 137.83, 135.62, 130.19, 116.93, 81.38, 75.20, 55.62, 51.74, 36.15, 29.48, 26.05, 25.49, 23.49, 9.44, 9.15.

HRMS (FAB/NBA): calcd (M+H)$^+$ for C$_{18}$H$_{30}$O$_4$N: 324.2175. Found: 324.2186.

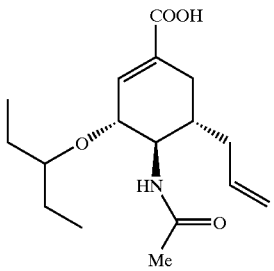

Example 2B (3R,4R,5S)-4-(acetylamino)-5-allyl-3-(1-ethylpropoxy)-1-cyclohexene-1-carboxylic acid Aqueous lithium hydroxide solution (0.1N, 15 mL) was added to a room temperature solution of Example 2A (150 mg, 0.464 mmol) in THF (5 mL). The solution was stirred for 10 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 143 mg (100%) of the desired product as a white solid.

m.p. 229–230° C.

[α]$^D_{295}$ −63.68° (c 0.190, methanol).

$^1$H NMR (400 MHz, CD$_3$OD): δ6.75 (m, 1H), 5.78 (m., 1H), 5.02 (m, 2H), 4.02 (m, 1H), 3.69 (m, 1H), 3.38 (p, J=5.6 Hz, 1H), 2.52 (m, 1H), 2.30 (m, 1H), 2.01 (m, 2H), 1.98 (s, 3H), 1.84 (m, 1H), 1.52 (m, 4H), 0.92 (m, 6H).

$^{13}$C NMR (100.6 MHz, CD$_3$OD): δ173.32, 139.04, 137.21, 117.13, 83.44, 77.99, 55.90, 38.56, 37.50, 31.26, 27.17, 26.66, 22.96, 9.90, 9.57.

HRMS (FAB/NBA): calcd (M+H)$^+$ for C$_{17}$H$_{28}$O$_4$N: 310.2018. Found: 310.2012.

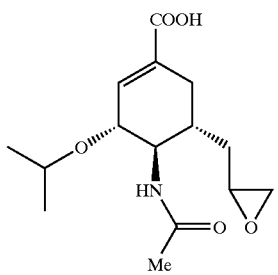

Example 3

(3R,4R,5R)-4-(acetylamino)-3-isopropoxy-5-(2-oxiranylmethyl)-1-cyclohexene-1-carboxylic acid

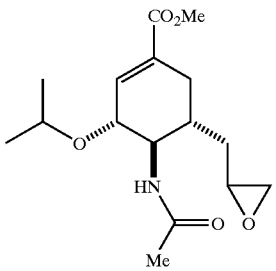

Example 3A methyl (3R,4R,5R)-4-(acetylamino)-3-isopropoxy-5-(2-oxiranylmethyl)-1-cyclohexene-1-carboxylate Meta-chloro perbenzoic acid (66 mg, 0.267 mmol) was added to a room temperature solution of Example 1N (52.6 mg, 0.178 mmol) in dichloromethane (10 mL). After stirring for 16 hours, the reaction mixture was concentrated. The concentrate was purified by flash chromatography on silica gel using ethyl acetate to afford 37.4 mg (68%) of the desired product as a white solid.

m.p. 130–131° C.

[α]$^D_{295}$ −32.34° (c 0.773, ethyl acetate).

$^1$H NMR (400 MHz, CDCl$_3$): δ6.78 (m, 1H), 5.70, 5.55 (m, 1H), 4.30, 4.09 (m, 1H), 3.76 (m, 1H), 3.74 (2×s, 3H), 3.64, 3.45 (m, 1H), 2.98 (m, 1H), 2.75 (m, 2H), 2.48 (m, 1H), 2.42 (m, 2H), 2.00 (2×s, 3H), 1.62 (m, 2H), 1.16 (2×d, J=6.1 Hz, 6H).

$^{13}$C NMR (100.6 MHz, CDCl$_3$): δ170.22, 166.76, 138.14, 138.03, 130.08, 129.94, 75.39, 74.28, 71.22, 54.70, 51.82, 50.32, 50.03, 47.82, 46.35, 34.86, 34.60, 29.96, 29.92, 23.49, 23.42, 23.00, 22.24, 22.16.

HRMS (FAB/NBA): calcd (M+H)$^+$ for C$_{16}$H$_{26}$O$_5$N: 312.18109. Found: 312.18030

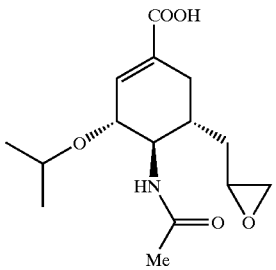

Example 3B (3R,4R,5R)-4-(acetylamino)-3-isopropoxy-5-(2-oxiranylmethyl)-1-cyclohexene-1-carboxylic acid Aqueous lithium hydroxide solution (0.1N, 15 mL) was added to a room temperature solution of Example 3A (30 mg, 0.096 mmol) in THF (5 mL). The solution was stirred for 10 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 25 mg (88%) of the desired product as a white solid.

m.p. 156–157° C.

$[\alpha]^P{}_{295}$ −12.57° (c 0.350, methanol).

$^1$H NMR (400 MHz, CD$_3$OD): δ6.68 (m, 1H), 4.07 (m, 2H), 3.78 (m, 1H), 2.96 (m, 1H), 2.72 (m, 2H), 2.48 (m, 1H), 2.10 (m, 2H), 1.98 (s, 3H), 1.70 (m, 1H), 1.40 (m, 1H), 1.15 (2×d, J=8.1 Hz, 6H).

$^{13}$C NMR (100.6 MHz, CD$_3$OD): δ173.61, 172.25, 138.08, 137.98, 78.09, 77.91, 73.47, 56.14, 55.88, 52.23, 51.31, 47.49, 37.76, 36.87, 36.50, 36.18, 31.88, 23.86, 23.56, 23.00, 22.90.

HRMS (FAB/NBA): calcd (M)$^+$ for C$_{15}$H$_{23}$O$_5$N: 297.15762. Found: 297.15620.

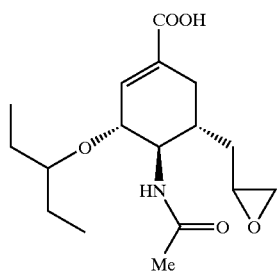

Example 4

(3R,4R,5R)-4-(acetylamino)-3-(1-ethylpropoxy)-5-(2-oxiranylmethyl)-1-cyclohexene-1-carboxylic acid

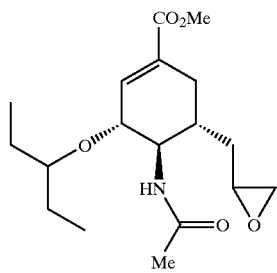

Example 4A methyl (3R,4R,5R)-4-(acetylamino)-3-(1-ethylpropoxy)-5-(2-oxiranylmethyl)-1-cyclohexene-1-carboxylate Meta-chloro perbenzoic acid (200 mg, 0.811 mmol) was added to a room temperature solution of Example 2A (150 mg, 0.464 mmol) in dichloromethane (30 mL). After stirring for 16 hours, the reaction mixture was concentrated. The concentrate was purified by flash chromatography on silica gel using ethyl acetate to afford 134 mg (85%) of the desired product as a mixture of two diastereomers.

$^1$H NMR (400 MHz, CDCl$_3$): δ6.76 (m, 1H), 5.83–5.69 (m, 1H), 4.24–4.05 (m, 1H), 3.74 (ss, 3H), 3.69–3.52 (m, 1H), 3.30 (m, 1H), 2.96 (m, 1H), 2.72 (m, 2H), 2.44 (m, 1H), 2.15 (m, 2H), 1.98 (ss, 3H), 1.88 (m, 1H), 1.52 (m, 1H), 1.48 (m, 4H), 0.84 (m, 6H).

$^{13}$C NMR (100.6 MHz, CDCl$_3$): δ170.16, 166.89, 166.81, 138.12, 138.01, 129.95, 129.76, 81.47, 81.41, 75.60, 74.66, 55.83, 54.86, 51.78, 50.38, 50.01, 47.76, 46.31, 35.08, 34.80, 34.74, 34.59, 30.01, 29.89, 26.02, 25.46, 23.46, 23.40, 9.40, 9.13, 9.10.

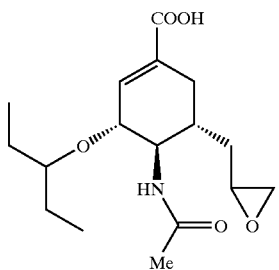

Example 4B (3R,4R,5R)-4-(acetylamino)-3-(1-ethylpropoxy)-5-(2-oxiranylmethyl)-1-cyclohexene-1-carboxylic acid Aqueous lithium hydroxide solution (0.1N, 15 mL) was added to a room temperature solution of Example 4A (40 mg, 0.118 mmol) in THF (5 mL). The solution was stirred for 10 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 37 mg (96%) of the desired product as a white solid.

m.p. 115–116° C.

$[\alpha]^P{}_{295}$ +50.00° (c 0.180, methanol).

$^1$H NMR (400 MHz, CD$_3$OD): δ6.79 (m, 1H), 4.05 (m, 1H), 3.74 (m, 1H), 3.39 (qu, J=5.6 Hz, 1H), 3.00 (m, 1H), 2.74 (m, 2H), 2.50 (m, 1H), 2.08 (m, 2H), 1.99 (2×s, 3H), 1.66 (m, 1H), 1.53 (m, 5H), 0.93 (m, 6H).

$^{13}$C NMR (100.6 MHz, CD$_3$OD): δ175.46, 173.40, 170.21, 139.09, 138.94, 132.24, 132.07, 83.41, 83.37, 77.78, 77.61, 56.00, 55.71, 52.10, 51.11, 48.40, 47.25, 37.86, 36.88, 36.25, 35.90, 31.83, 31.38, 27.18, 26.67, 22.97, 20.90, 9.89, 9.58. HRMS (FAB/NBA): calcd (M+H)$^+$ for C$_{17}$H$_{28}$O$_5$N: 326.1967. Found: 326.1976.

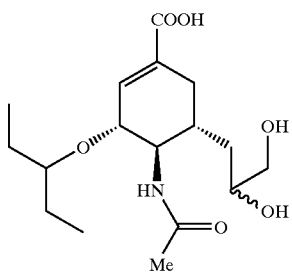

Example 5 (3R,4R,5R)-4-(acetylamino)-5-(2,3-dihydroxypropyl)-3-(1-ethylpropoxy)-1-cyclohexene-1-carboxylic acid

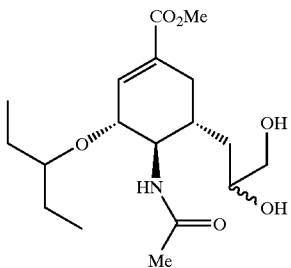

Example 5A methyl (3R,4R,5R)-4-(acetylamino)-5-(2,3-dihydroxypropyl)-3-(1-ethylpropoxy)-1-cyclohexene-1-carboxylate Water (1.6 mL), NMO (28 mg, 0.239 mmol), and OsO$_4$ (25 mg/ml in toluene, 16 μL, 1.57 μmol) were added to a room temperature solution of Example 2A (51 mg, 0.158 mmol) in acetone (15 mL). After stirring for 3 hours, the reaction mixture was concentrated. The concentrate was purified by flash chromatography on silica gel using acetone to afford 23 mg (40%) of the desired product as a white solid.

m.p. 125–126° C.

$[\alpha]^P_{295}$ +51.82° (c 0.110, methanol).

$^1$H NMR (400 MHz, CD$_3$OD): δ8.00 (2×d, J=9.5 Hz, 1H), 6.78 (m, 1H), 4.00 (m, 1H), 3.75 (2×s, 3H), 3.72 (m, 2H), 3.44 (m, 3H), 2.72 (m, 1H), 2.10 (m, 1H), 1.99 (s, 3H), 1.82 (m, 1H), 1.62 (m, 1H), 1.52 (m, 4H), 1.30 (m, 1H), 0.89 (m, 6H). $^{13}$C NMR (100.6 MHz, CD$_3$OD): δ173.44, 173.35, 168.53, 168.49, 139.67, 139.42, 131.48, 131.26, 83.39, 83.35, 77.80, 77.55, 72.04, 69.56, 68.11, 67.22, 56.34, 55.99, 52.43, 36.69, 36.40, 36.11, 34.91, 32.12, 30.89, 27.18, 26.65, 23.06, 23.01, 9.93, 9.60.

HRMS (FAB/NBA): calcd (M+H)$^+$ for C$_{18}$H$_{32}$O$_6$N: 358.22296. Found: 358.22209.

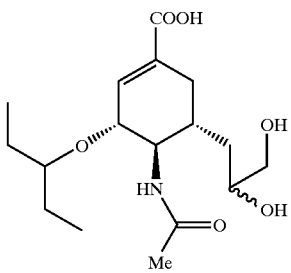

Example 5B (3R,4R,5R)-4-(acetylamino)-5-(2,3-dihydroxypropyl)-3-(1-ethylpropoxy)-1-cyclohexene-1-carboxylic acid Aqueous lithium hydroxide solution (0.1N, 15 mL) was added to a room temperature solution of Example 5A (20 mg, 0.056 mmol) in THF (5 mL). The solution was stirred for 10 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 19 mg (100%) of the desired product as a white solid.

m.p. 189–190° C.

$[\alpha]^P_{295}$ +35.59° (c 0.340, methanol).

$^1$H NMR (400 MHz, CD$_3$OD): δ6.76 (m, 1H), 4.01 (m, 1H), 3.73 (m, 2H), 3.44 (m, 3H), 2.72 (m, 1H), 2.05 (m, 1H), 1.99 (s, 3H), 1.83 (m, 1H), 1.56 (m, 1H), 1.51 (m, 4H), 1.29 (m, 1H), 0.90 (m, 6H).

$^{13}$C NMR (100.6 MHz, CD$_3$OD): δ173.47, 173.40, 138.69, 138.43, 83.37, 83.34, 78.05, 77.80, 71.97, 69.63, 68.13, 67.15, 56.49, 56.17, 36.77, 36.40, 36.21, 35.01, 32.36, 31.17, 27.20, 26.68, 23.01, 9.91, 9.62.

HRMS (FAB/NBA): calcd (M+H)$^+$ for C$_{17}$H$_{30}$O$_6$N: 344.20731. Found: 344.20790.

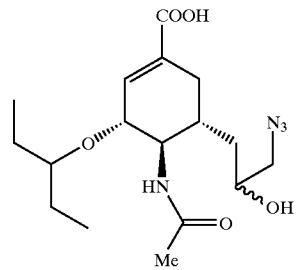

Example 6

(3R,4R,5R)-4-(acetylamino)-5-(3-azido-2-hydroxyoropyl)-3-(1-ethylpropoxy)-1-cyclohexene-1-carboxylic acid

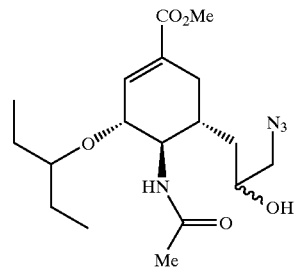

Example 6A methyl (3R,4R,5R)-4-(acetylamino)-5-(3-azido-2-hydroxypropyl)-3-(1-ethylpropoxy)-1-cyclohexene-1-carboxylate Water (5 mL), sodium azide (100 mg, 1.53 mmol), ammonium chloride (40 mg, 0.747 mmol) and Example 4A (120 mg, 0.354 mmol) were refluxed in methanol (15 mL) for 5 hours. The reaction mixture was cooled to room temperature, diluted with H$_2$O, and extracted with ethyl acetate. The ethyl acetate was dried (MgSO$_4$), filtered and concentrated. The concentrate was purified by flash chromatography on silica gel using acetone/ethyl acetate (1:5) to afford 122 mg (90%) of the desired product as a colorless oil.

m.p. 92–93° C.

$[\alpha]D_{295}$ −51.54° (c 0.130, methanol).

$^1$H NMR (400 MHz, CDCl$_3$): δ6.79 (m, 1H), 5.69 (2×d, J=9.4 Hz, 1H), 4.04 (m, 1H), 3.87 (m, 1H), 3.75 (s, 3H), 3.65 (m, 1H), 3.32–3.19 (m, 3H), 2.70 (m, 1H), 2.20 (m, 1H), 2.01 (m, 4H), 1.77 (m, 1H), 1.51 (m, 5H), 0.88 (m, 6H).

$^{13}$C NMR (100.6 MHz, CDCl$_3$): δ171.05, 170.48, 166.85, 137.93, 137.20, 130.29, 129.78, 81.54, 81.25, 77.09, 75.72, 75.27, 68.40, 67.53, 57.77, 57.23, 55.10, 55.03, 51.85, 35.66, 34.88, 33.89, 33.18, 29.72, 29.26, 26.02, 25.50, 25.44, 23.48, 9.46, 9.41, 9.12.

HRMS (FAB/NBA): calcd (M+H)$^+$ for C$_{17}$H$_{28}$O$_5$N: 383.22943. Found: 383.23080.

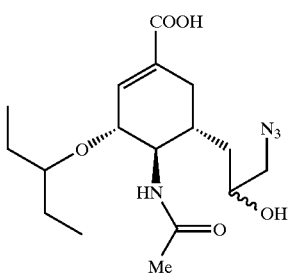

Example 6B

(3R,4R,5R)-4-(acetylamino)-5-(3-azido-2-hydroxypropyl)-3-(1-ethylpropoxy)-1-cyclohexene-1-carboxylic acid Aqueous lithium hydroxide solution (0.1N, 15 mL) was added to a room temperature solution of Example 6A (50 mg, 0.131 mmol) in THF (5 mL). The solution was stirred for 10 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 48 mg (100%) of the desired product as a white solid.

m.p. 126–127° C.

[α]$^P_{295}$ +54.37° (c 0.160, methanol).

$^1$H NMR (400 MHz, CD$_3$OD): δ6.80 (m, 1H), 4.02 (m, 1H), 3.83 (m, 1H), 3.71 (m, 1H), 3.39 (m, 1H), 3.21 (m, 2H), 2.68 (m, 1H), 2.07 (m, 1H), 1.99 (s, 3H), 1.83 (m, 1H), 1.54 (m, 4H), 1.34 (m, 1H), 0.89 (m, 6H).

$^{13}$C NMR (100.6 MHz, CD$_3$OD): δ173.46, 173.39, 169.91, 139.45, 139.14, 131.81, 131.65, 83.41, 83.38, 77.80, 77.42, 70.61, 68.28, 58.65, 57.59, 56.24, 55.91, 37.71, 37.07, 36.16, 34.99, 31.93, 30.71, 27.18, 26.68, 22.92, 9.87, 9.60.

HRMS (FAB/NBA): calcd (M+H)$^+$ for C$_{17}$H$_{29}$O$_5$N$_4$: 369.213795. Found: 369.212407.

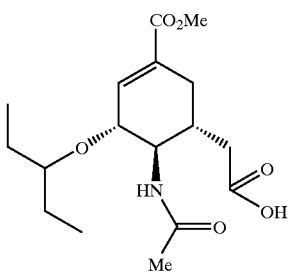

Example 7

[(1R,5R,6R)-6-(acetylamino)-5-(1-ethylpropoxy)-3-(methoxycarbonyl)-3-cyclohexen-1-yl]acetic acid

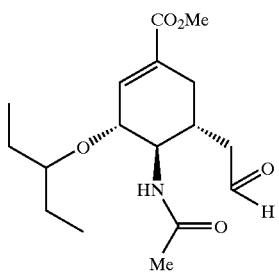

Example 7A methyl (3R,4R,5R)-4-(acetylamino)-3-(1-ethylpropoxy)-5-(2-oxoethyl)-1-cyclohexene-1-carboxylate Sodium periodate (46 mg, 0.215 mmol) and water (1.0 mL) were added to a room temperature solution of Example 5A (52 mg, 0.146 mmol) in methanol (10 mL). After stirring for 3 hours, the reaction mixture was filtered, and then concentrated. The concentrate was purified by flash chromatography on silica gel using ethyl acetate to afford 37 mg (78%) of the desired product.

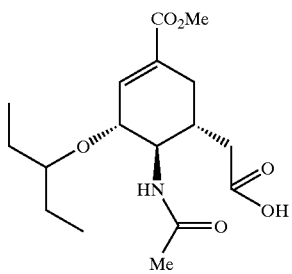

Example 7B

[(1R,5R,6R)-6-(acetylamino)-5-(1-ethylpropoxy)-3-(methoxycarbonyl)-3-cyclohexen-1-yl]acetic acid Sodium chlorite (commercial 80%, 16 mg, 0.142 mmol) in 2 mL of KH$_2$PO$_4$ buffer (pH 3–4) was added dropwise to a room temperature solution of Example 7A (36 mg, 0.110 mmol) and 2-methyl-2-butene (118 μL, 1.10 mmol) in tert-butyl alcohol (15 mL). After stirring for 16 hours, the reaction mixture was concentrated. The concentrate was purified by flash chromatography on silica gel using acetic acid/ethyl acetate (1/5) to afford 32 mg (84%) of the desired product as a white solid.

m.p. 164–165° C.

[α]$^P_{295}$ −34.66° (c 0.150, methanol).

$^1$H NMR (400 MHz, CD$_3$OD): δ6.78 (m, 1H), 4.06 (m, 1H), 3.77 (m, 1H), 3.75 (s, 3H), 3.39 (qn, J=5.6 Hz, 1H), 2.68 (m, 1H), 2.54 (m, 1H), 2.16 (m, 3H), 1.97 (s, 3H), 1.54 (m, 4H), 0.90 (2×t, J=7.4 Hz, 6H).

$^{13}$C NMR (100.6 MHz, CD$_3$OD): δ176.12, 173.54, 168.28, 139.64, 131.08, 83.50, 77.32, 55.60, 52.41, 37.95, 36.29, 31.44, 27.16, 26.65, 22.85, 9.82, 9.57.

HRMS (FAB/NBA): calcd (M+H)$^+$ for $C_{17}H_{28}O_6N$: 342.191663. Found: 342.190501.

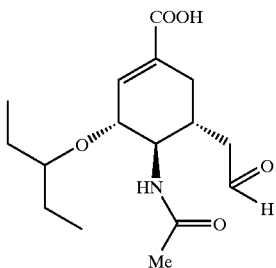

Example 8

(3R,4R,5R)-4-(acetylamino)-3-(1-ethylpropoxy)-5-(2-oxoethyl)-1-cyclohexene-1-carboxylic acid

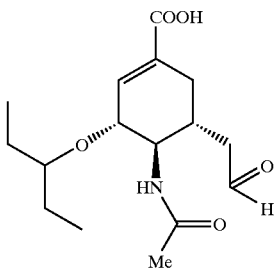

Example 8A (3R,4R,5R)-4-(acetylamino)-3-(1-ethylpropoxy)-5-(2-oxoethyl)-1-cyclohexene-1-carboxylic acid Aqueous lithium hydroxide solution (0.1N, 15 mL) was added to a room temperature solution of Example 7A (30 mg, 0.092 mmol) in THF (3 mL). The solution was stirred for 12 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 23 mg (100%) of the desired product as a white solid.

m.p. 70–71° C.

$[\alpha]^P_{295}$ −27.50° (c 0.160, methanol).

$^1$H NMR (400 MHz, CD$_3$OD): δ6.78 (m, 1H), 4.01 (m, 1H), 3.70 (m, 1H), 3.37 (m, 1H), 2.62 (m, 1H), 2.07 (m, 1H), 1.99 (s, 3H), 1.83 (m, 2H), 1.50 (m, 4H), 1.40 (m, 1H), 0.92 (m, 6H). $^{13}$C NMR (100.6 MHz, CD$_3$OD): δ175.31, 173.36, 170.06, 139.20, 131.92, 83.39, 77.71, 55.90, 35.44, 31.39, 27.18, 26.67, 22.90, 20.79, 9.87, 9.59.

HRMS (FAB/NBA): calcd (M+H)+ for $C_{16}H_{26}O_5N$: 312.181098. Found: 312.179866.

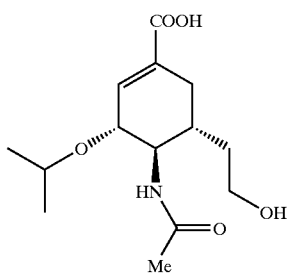

Example 9

(3R,4R,5R)-4-(acetylamino)-5-(2-hydroxyethyl)-3-isopropoxy-1-cyclohexene-1-carboxylic acid

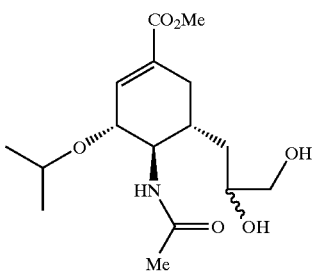

Example 9A methyl (3R,4R,5R)-4-(acetylamino)-5-(2,3-dihydroxypropyl)-3-isopropoxy-1-cyclohexene-1-carboxylate Water (3 mL), NMO (86 mg, 0.735 mmol), and OsO$_4$ (25 mg/ml in toluene, 50 μL, 4.92 μmol) were added to a room temperature solution of Example 1N (145 mg, 0.492 mmol) in acetone (30 mL). After stirring for 3 hours, the reaction mixture was concentrated. The concentrate was purified by flash chromatography on silica gel using acetone to afford 72 mg (45%) of the desired product as a white solid.

$^1$H NMR (400 MHz, CD$_3$OD): δ6.75 (m, 1H), 4.01 (m, 1H), 3.80 (m, 1H), 3.77 (2×s, 3H), 3.70 (m, 1H), 3.44 (m, 3H), 2.76 (m, 1H), 2.05 (m, 2H), 2.00 (2×s, 3H), 1.63 (m, 1H), 1.31 (m, 1H), 1.15 (m, 6H).

$^{13}$C NMR (100.6 MHz, CD$_3$OD): δ173.40, 168.50, 139.74, 139.44, 131.54, 131.34, 77.84, 77.44, 73.41, 73.31, 72.00, 69.59, 68.11, 67.26, 56.16, 55.93, 52.42, 36.80, 36.21, 36.04, 34.64, 34.64, 32.10, 30.94, 23.42, 23.38, 22.90, 22.77.

HRMS (FAB/NBA): calcd (M+H)$^+$ for $C_{16}H_{28}O_6N$: 330.191663. Found: 330.190688.

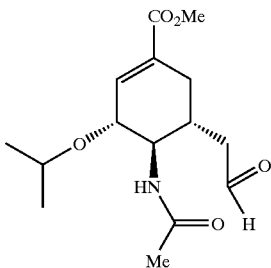

Example 9B methyl (3R,4R,5R)-4-(acetylamino)-3-isopropoxy-5-(2-oxoethyl)-1-cyclohexene-1-carboxylate Procedure A: Sodium periodate (70 mg, 0.327 mmol) and water (1.5 mL) were added to a room temperature solution of Example 9A (71 mg, 0.216 mmol) in methanol (15 mL). After stirring for 3 hours, the reaction mixture was filtered and concentrated. The concentrate was purified by flash chromatography on silica gel using ethyl acetate to afford 45 mg (71%) of the desired product as a white solid.

Procedure B: Sodium periodate (0.174 g, 0.814 mmol), water (1.0 mL) and OsO$_4$ (25 mg/ml in toluene, 70 µL, 6.89 µmol) were added to a room temperature solution of Example 1N (0.200 g, 0.678 mmol) in acetone (15 mL). After stirring for 3 hours, the reaction mixture was concentrated. The concentrate was purified by flash chromatography on silica gel using hexanes/ethyl acetate (1/6) to afford 0.120 g (60%) of the desired product as a white solid.

m.p. 116–117° C.

$[\alpha]^P{}_{295}$ –30.50° (c 0.400, ethyl acetate).

$^1$H NMR (400 MHz, CDCl$_3$): δ9.75 (t, J=1.1 Hz, 1H), 6.76 (m, 1H), 5.71 (d, J=8.9 Hz, 1H), 4.08 (m, 1H), 3.73 (m, 2H), 3.72 (s, 3H), 2.76 (m, 1H), 2.56 (m, 2H), 2.46 (m, 1H), 2.15 (m, 1H), 1.94 (s, 3H), 1.14 (2×d, J=6.1 Hz, 6H).

$^{13}$C NMR (100.6 MHz, CDCl$_3$): δ201.53, 170.32, 166.55, 138.20, 129.86, 75.20, 71.38, 54.50, 51.81, 46.83, 31.56, 30.47, 23.27, 22.94, 22.21.

HRMS (FAB/NBA): calcd (M+H)$^+$ for C$_{15}$H$_{24}$O$_5$N: 298.165448. Found: 298.166321.

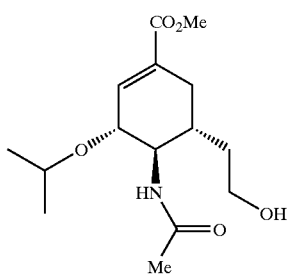

Example 9C methyl (3R,4R,5R)-4-(acetylamino)-5-(2-hydroxyethyl)-3-isopropoxy-1-cyclohexene-1-carboxylate Sodium borohydride (20 mg, 0.529 mmol) was added to a 0° C. solution of Example 9B (45 mg, 0.152 mmol) in methanol (10 mL). After stirring for 30 minutes, the reaction mixture was quenched with aqueous NH$_4$Cl, and concentrated. The concentrate was purified by flash chromatography on silica gel using acetone/ethyl acetate (1/4) to afford 41.7 mg (92%) of the desired product as a white solid.

m.p. 118–119° C.

$[\alpha]^P{}_{295}$ –35.06° (c 0.770, methanol).

$^1$H NMR (400 MHz, CD$_3$OD): δ6.74 (m, 1H), 4.03 (m, 1H), 3.79 (m, 1H), 3.75 (s, 3H), 3.67 (m, 3H), 2.63 (m, 1H), 2.00 (s, 3H), 1.96 (m, 1H), 1.88 (m, 2H), 1.36 (m, 1H), 1.16 (2×d, J=6.1 Hz, 6H).

$^{13}$C NMR (100.6 MHz, CD$_3$OD): δ173.33, 168.46, 139.68, 131.35, 77.67, 73.37, 60.20, 55.85, 52.39, 35.51, 35.34, 31.08, 23.37, 22.83, 22.72.

HRMS (FAB/NBA): calcd (M+H)$^+$ for C$_{15}$H$_{26}$O$_5$N: 300.181098. Found: 300.182440.

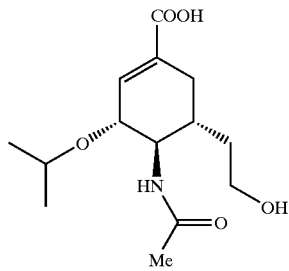

Example 9D (3R,4R,5R)-4-(acetylamino)-5-(2-hydroxyethyl)-3-isopropoxy-1-cyclohexene-1-carboxylic acid Aqueous lithium hydroxide solution (0.1N, 15 mL) was added to a room temperature solution of Example 9C (30 mg, 0.10 mmol) in THF (3 mL). The solution was stirred for 12 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 27 mg (96%) of the desired product as a white solid.

m.p. 114–115° C.

$[\alpha]^P{}_{295}$ –26.66° (c 0.210, methanol).

$^1$H NMR (400 MHz, CD$_3$OD): δ6.68 (m, 1H), 4.00 (m, 1H), 3.79 (h, J=6.1 Hz, 1H), 3.61 (m, 3H), 2.62 (m, 1H), 2.00 (s, 3H), 1.88 (m, 3H), 1.38 (m, 1H), 1.16 (2×d, J=6.1 Hz, 6H).

$^{13}$C NMR (100.6 MHz, CD$_3$OD): δ173.35, 137.83, 78.03, 73.24, 60.28, 56.03, 35.64, 35.50, 31.55, 23.39, 22.82, 22.75.

HRMS (FAB/NBA): calcd (M+H)$^+$ for C$_{14}$H$_{24}$O$_5$N: 286.165448. Found: 286.165897.

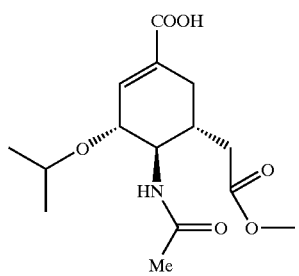

Example 10

(3R,4R,5R)-4-(acetylamino)-3-isopropoxy-5-(2-methoxy-2-oxoethyl)-1-cyclohexene-1-carboxylic acid

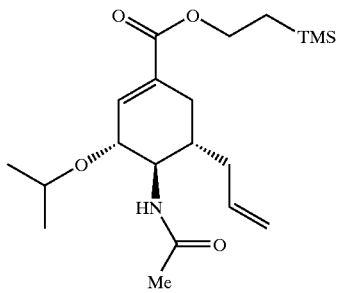

Example 10A 2-(trimethylsilyl)ethyl (3R,4R,5S)-4-(acetylamino)-5-allyl-3-isopropoxy-1-cyclohexene-1-carboxylate Triethylamine (0.4 mL, 2.88 mmol) and 2-chloro-1-methylpyridinium iodide (350 mg, 1.37 mmol) were added to a room temperature solution of Example 10 (188 mg, 0.670 mmol) and 2-(trimethylsilyl)ethanol (165 mg, 1.40 mmol) in dichloromethane (30 mL). After stirring for 16 hours, the reaction was quenched with water and extracted with ethyl acetate. The combined ethyl acetate layers were dried (MgSO$_4$), filtered and concentrated. The concentrate was purified by flash chromatography on silica gel using ethyl acetate to afford 170 mg (67%) of the desired product as a white solid.

m.p. 64–65° C.

$[\alpha]^D_{295}$ –34.54° (c 0.110, ethyl acetate).

$^1$H NMR (400 MHz, CD$_3$OD): δ6.71 (m, 1H), 5.94 (d, J=8.6 Hz, 1H), 5.72 (m, 1H), 5.00 (m, 2H), 4.20 (m, 2H), 4.12 (m, 1H), 3.73 (h, J=6.1 Hz, 1H), 3.55 (m, 1H), 2.45 (m, 1H), 2.29 (m, 1H), 2.04 (m, 3H), 1.97 (s, 3H), 1.13 (2×d, J=6.1 Hz, 6H), 1.00 (m, 2H), 0.01 (s, 9H).

$^{13}$C NMR (100.6 MHz, CD$_3$OD): δ170.10, 166.65, 137.59, 135.57, 130.66, 116.88, 75.26, 71.17, 62.81, 55.04, 36.20, 29.50, 23.36, 22.98, 22.24, 17.11, –1.60.

HRMS (FAB/NBA): calcd (M+H)$^+$ for C$_{20}$H$_{36}$O$_4$NSi: 382.241362. Found: 382.243564.

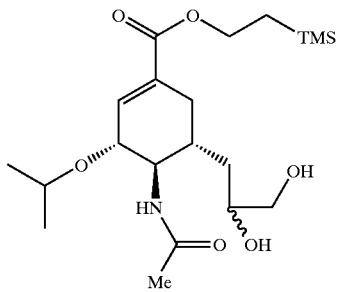

Example 10B 2-(trimethylsilyl)ethyl (3R,4R,5R)-4-(acetylamino)-5-(2,3-dihydroxypropyl)-3-isopropoxy-1-cyclohexene-1-carboxylate Water (1.5 mL), NMO (32 mg, 0.274 mmol), and OsO$_4$ (25 mg/ml in toluene, 20 μL, 1.97 μmol) were added to a room temperature solution of Example 10A (70 mg, 0.183 mmol) in acetone (15 mL). After stirring for 3 hours, the reaction mixture was concentrated. The concentrate was purified by flash chromatography on silica gel using acetone to afford 33 mg (43%) of the desired product.

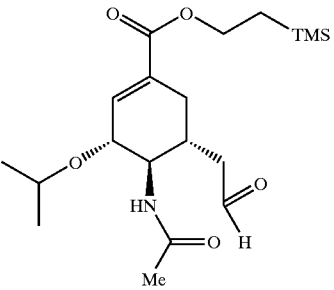

Example 10C 2-(trimethylsilyl)ethyl (3R,4R,5R)-4-(acetylamino)-3-isopropoxy-5-(2-oxoethyl)-1-cyclohexene-1-carboxylate Sodium periodate (54 mg, 0.252 mmol) and water (1.5 mL) were added to a room temperature solution of Example 10B (70 mg, 0.168 mmol) in methanol (15 mL). After stirring for 3 hours, the reaction mixture was filtered and concentrated. The concentrate was purified by flash chromatography on silica gel using ethyl acetate to afford 57 mg (92%) of the desired product.

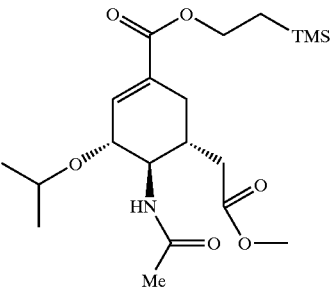

Example 10D ((1R,5R,6R)-6-(acetylamino)-5-isopropoxy-3-{[2-(trimethylsilyl)ethoxy]carbonyl}-3-cyclohexen-1-yl)ethaneperoxoic acid Sodium chlorite (commercial 80%, 80 mg, 0.708 mmol) in 10 mL of KH$_2$PO$_4$ buffer (pH 3–4) was added dropwise to a room temperature solution of Example 10C (194 mg, 0.528 mmol) and 2-methyl-2-butene (560 μL, 5.28 mmol) in tert-butyl alcohol (30 mL). After stirring for 16 hours, the reaction mixture was concentrated. The concentrate was passed through a short pad of silica gel using acetic acid/ethyl acetate (1/5) affording the crude acid.

Diazomethane in ether was added to the crude acid in 0° C. THF. After stirring for 30 minutes, the concentrate was purified by flash chromatography on silica gel using ethyl acetate to afford 84 mg (40%) of the desired product.

$[\alpha]^D_{295}$ –35.00° (c 0.200, ethyl acetate).

$^1$H NMR (400 MHz, CDCl$_3$): δ6.73 (m, 1H), 5.69 (d, J=9.0 Hz, 1H), 4.20 (m, 2H), 4.03 (m, 1H), 3.70 (m, 2H), 3.64 (s, 3H), 2.50 (m, 2H), 2.40 (m, 1H), 2.30 (m, 1H), 2.11 (m, 1H), 1.94 (s, 3H), 1.13 (2×d, J=6.1 Hz, 6H), 1.01 (m, 2H), 0.02 (s, 9H).

$^{13}$C NMR (100.6 MHz, CDCl$_3$): δ173.43, 170.11, 166.31, 137.80, 130.25, 75.52, 71.34, 62.93, 54.39, 51.54, 36.74, 33.88, 30.25, 23.20, 22.93, 22.21, 17.13, −1.62.

HRMS (FAB/NBA): calcd (M+H)$^+$ for C$_{20}$H$_{36}$O$_6$NSi: 414.231192. Found: 414.230313.

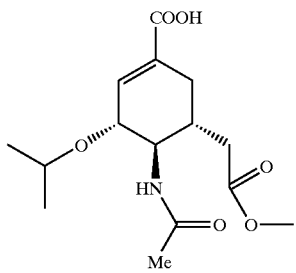

Example 10E (3R,4R,5R)-4-(acetylamino)-3-isopropoxy-5-(2-methoxy-2-oxoethyl)-1-cyclohexene-1-carboxylic acid Tetrabutylammonium fluoride in THF (1.0 M, 0.2 mL, 0.2 mmol) was added to a room temperature solution of Example 10D (50 mg, 0.126 mmol) in THF (15 mL). After stirring for 3 hours, the reaction mixture was concentrated. The concentrate was purified by flash chromatography using acetic acid/ethyl acetate (1/5) to afford 38 mg (97%) of the desired product as a white solid.

m.p. 163–164° C.

[α]$^P_{295}$ −51.90° (c 0.210, methanol).

$^1$H NMR (400 MHz, CD$_3$OD): δ6.76 (m, 1H), 4.07 (m, 1H), 3.80 (m, 2H), 3.68 (s, 3H), 2.56 (m, 2H), 2.26 (m, 2H), 2.07 (m, 1H), 1.97 (s, 3H), 1.16 (2×d, J=6.1 Hz, 6H).

$^{13}$C NMR (100.6 MHz, CD$_3$OD): δ174.56, 173.53, 169.63, 139.38, 131.65, 77.32, 73.40, 55.46, 52.13, 37.86, 35.98, 31.42, 23.34, 22.75.

HRMS (FAB/NBA): calcd (M+H)$^+$ for C$_{15}$H$_{24}$O$_6$N: 314.160363. Found: 314.159553.

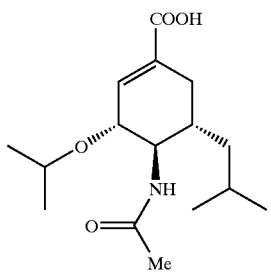

Example 11

(3R,4R,5R)-4-(acetylamino)-3-isopropoxy-5-isopropyl-1-cyclohexene-1-carboxylic acid

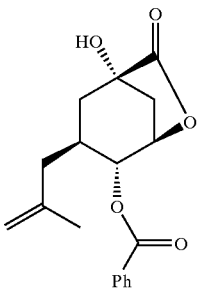

Example 11A (1S,3S,4R,5R)-1-hydroxy-3-(2-methyl-2-propenyl)-7-oxo-6-oxabicyclo[3.2.1]oct-4-yl benzoate n-Butyllithium (16.5 mL of a 2.5 M hexanes solution, 41.2 mmol) was added to a 0° C. solution of diisopropylamine (5.4 mL, 41.3 mmol) in THF (40 mL). After stirring for 5 minutes, tributyltin hydride (10 g, 34.4 mmol) was added. After stirring for 15 minutes at 0° C., the reaction mixture was cooled to −78° C. and 3-bromo-2-methylpropene (4.0 mL, 39.7 mmol) was added dropwise. After stirring for an additional hour, the cold reaction mixture was quenched with dilute ammonium chloride solution and extracted with ethyl acetate. The ethyl acetate layer was dried (MgSO$_4$), filtered and concentrated to afford a colorless liquid, 2-methylallyl tributyltin (11.6 g, 98%) which was used without purification for the next step.

2-Methylallyl tributyltin (11.6 g, 33.6 mmol), Example 1B (8.0 g, 24.3 mmol) and ACN (3.0 g, 12.3 mmol) were refluxed in toluene (150 mL) for 10 hours. The reaction mixture was concentrated and diluted with dichloromethane (100 mL). Aqueous KF.2H$_2$O (10%, 50 mL) was added, and the mixture was stirred for 2 hours at room temperature. The reaction mixture was filtered, dried (MgSO$_4$), filtered, and concentrated. The concentrate was purified by flash chromatography on silica gel hexanes/ethyl acetate (2/3) to afford 4.7 g (62%) of the desired product as a colorless oil.

[α]$^P_{295}$ −11.82° (c 0.880, ethyl acetate).

$^1$H NMR (400 MHz, CDCl$_3$): δ8.06–7.46 (m, 5H), 5.18 (m, 1H), 4.93 (m, 1H), 4.85 (m, 2H), 4.73 (m, 1H), 3.08 (m, 1H), 2.50 (m, 3H), 2.20 (m, 3H), 1.90 (m, 1H), 1.67 (s, 3H).

$^{13}$C NMR (100.6 MHz, CDCl$_3$): δ178.70, 165.06, 141.78, 133.51, 129.55, 129.19, 128.49, 114.08, 75.40, 71.89, 70.45, 42.46, 37.26, 35.47, 21.51.

HRMS (FAB/NBA): calcd (M+H)$^+$ for C$_{18}$H$_{21}$O$_5$: 317.13889. Found: 317.14010.

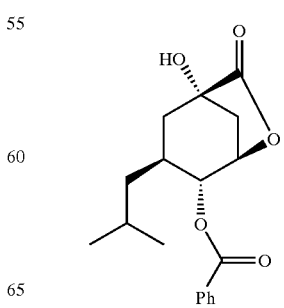

Example 11B (1S,3S,4R,5R)-1-hydroxy-3-isobutyl-7-oxo-6-oxabicyclo[3.2.1]oct-4-yl benzoate Example 11A (4.0 g, 12.6 mmol), and Pearlman's catalyst (50 mg) in ethyl acetate (20 mL) were stirred for 10 hours under 40 PSI of hydrogen. The reaction mixture was filtered and concentrated to afford (100%) of the desired product as a white solid.

m.p. 71–72° C.

$[\alpha]^{p}_{295}$ +15.00° (c 0.160, ethyl acetate).

$^1$H NMR (400 MHz, CDCl$_3$): δ8.05–7.46 (m, 5H), 5.14 (m, 1H), 4.90 (m, 1H), 3.04 (s, 1H), 2.50 (m, 2H), 2.34 (m, 2H), 1.82 (m, 1H), 1.68 (m, 1H), 1.50 (m, 1H), 1.32 (m, 2H), 0.88 (2×d, J=5.3 Hz, 6H).

$^{13}$C NMR (100.6 MHz, CDCl$_3$): δ178.82, 165.10, 133.47, 129.54, 128.48, 75.54, 71.97, 71.14, 43.60, 37.25, 34.67, 25.73, 22.57, 21.83.

HRMS (FAB/NBA) calcd (M+H)$^+$ for $C_{18}H_{23}O_5$: 319.15454. Found: 319.15310.

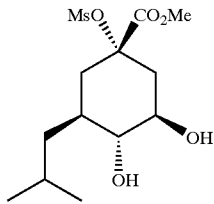

Example 11C methyl (1S,3R,4R,5S)-3,4-dihydroxy-5-isobutyl-1-[(methylsulfonyl)oxy]cyclohexanecarboxylate Methanesulfonyl chloride (1.5 mL, 19.4 mmol) was added dropwise to a 0° C. solution of Example 11B (4.0 g, 12.6 mmol) and triethylamine (3.5 mL, 25.2 mmol) in dichloromethane (50 mL). The reaction mixture was stirred for 5 hours, washed with saturated NaHCO$_3$ solution, brine, dried (MgSO$_4$), filtered and concentrated.

The concentrate was dissolved in methanol (30 mL) and K$_2$CO$_3$ (100 mg) was added. After stirring for 1 hour the reaction mixture was filtered, and concentrated. The concentrate was purified by flash chromatography on silica gel using ethyl acetate to afford 3.7 g (92%) of the desired product as a white solid.

m.p. 122–123° C.

$[\alpha]^{p}_{295}$ +42.22° (c 0.180, ethyl acetate).

$^1$H NMR (400 MHz, CDCl$_3$): δ3.85 (m, 1H), 3.81 (s, 3H), 3.17 (s, 3H), 3.10 (m, 1H), 2.61 (m, 1H), 2.40 (m, 1H), 1.90 (m, 2H), 1.66 (m, 2H), 1.52 (m, 1H), 1.05 (m, 1H), 0.91 (2×d, J=6.1 Hz, 6H).

$^{13}$C NMR (100.6 MHz, CDCl$_3$): δ170.77, 87.93, 78.83, 70.47, 52.99, 40.79, 40.41, 39.52, 37.64, 34.73, 24.74, 23.99, 21.15.

HRMS (FAB/NBA): calcd (M+H)$^+$ for $C_{13}H_{25}O_7S$: 325.13211. Found: 325.13070.

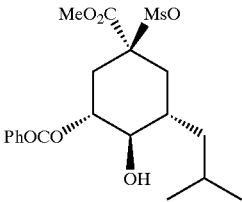

Example 11D (1R,2R,3S,5S)-2-hydroxy-3-isobutyl-5-(methoxycarbonyl)-5-[(methylsulfonyl)oxy] cyclohexyl benzoate Benzoyl chloride (0.68 mL, 5.86 mmol) was added dropwise to a 0° C. solution of Example 11C (1.9 g, 5.86 mmol) and pyridine (1.0 mL, 12.4 mmol) in dichloromethane (30 mL). After stirring for 5 hours, the reaction mixture was washed with aqueous HCl (2N), saturated NaHCO$_3$ solution, brine, dried (MgSO$_4$), filtered and concentrated. The concentrate was purified by flash chromatography on silica gel using hexanes/ethyl acetate (3/2) to afford 2.1 g (86%) of the desired product as a white solid.

m.p. 161–162° C.

$[\alpha]^{p}_{295}$ +18.75° (c 0.160, ethyl acetate).

$^1$H NMR (400 MHz, CDCl$_3$): δ8.05–7.34 (m, 5H), 5.25 (m, 1H), 3.85 (s, 3H), 3.48 (m, 1H), 3.28 (s, 3H), 2.81 (m, 1H), 2.52 (m, 1H), 2.25 (d, J=6.2 Hz, 1H), 2.08 (m, 2H), 1.70 (m, 3H), 1.10 (m, 1H), 0.97 (m, 6H).

$^{13}$C NMR (100.6 MHz, CDCl$_3$): δ170.46, 166.37, 133.27, 129.58, 128.34, 128.21, 86.97, 76.23, 74.17, 53.03, 40.85, 40.51, 37.46, 36.66, 35.31, 24.76, 23.97, 21.18.

HRMS (FAB/NBA): calcd (M+H)$^+$ for $C_{20}H_{29}O_8S$: 429.15833. Found: 429.15920.

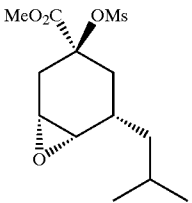

Example 11E methyl (1R,3S,5S,6S)-5-isobutyl-3-[(methylsulfonyl)oxy]-7-oxabicyclo[4.1.0]heptane-3-carboxylate Methanesulfonyl chloride (1.0 mL, 12.9 mmol) was added dropwise to a 0° C. solution of Example 11D (2.7 g, 6.3 mmol) and triethylamine (2.6 mL, 18.7 mmol) in dichloromethane (40 mL). After stirring for 10 hours, the reaction mixture was washed with saturated NaHCO$_3$ solution, brine, dried (MgSO$_4$), filtered and concentrated.

The concentrate was dissolved in dichloromethane (30 mL), and K$_2$CO$_3$ (100 mg) and methanol (15 mL) were added. After stirring for 10 hours, the reaction mixture was acidified to pH 5–6 with DOWEX® 50WX2-200 ion-exchange resin, filtered and concentrated. The concentrate was purified by flash chromatography on silica gel using hexanes/ethyl acetate (1/1) to afford 1.5 g (78%) of the desired product as a white solid.

m.p. 120–121° C.

[α]$^P_{295}$ −15.79° (c 0.190, ethyl acetate).

$^1$H NMR (400 MHz, CDCl$_3$): δ3.79 (s, 3H), 3.25 (m, 2H), 3.16 (s, 3H), 2.54 (m, 1H), 2.39 (m, 1H), 2.28 (m, 1H), 2.10 (m, 1H), 1.77 (h, J=6.7 Hz, 1H), 1.50 (m, 2H), 1.30 (m, 1H), 0.94 (2×d, J=6.6 Hz, 6H).

$^{13}$C NMR (100.6 MHz, CDCl$_3$): δ171.19, 86.41, 55.15, 52.94, 49.38, 41.79, 40.45, 33.26, 32.17, 27.88, 24.55, 22.81, 22.22.

HRMS (FAB/NBA): calcd (M+H)$^+$ for C$_{13}$H$_{23}$O$_6$S: 307.12152. Found: 307.12060.

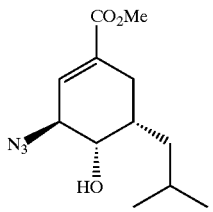

Example 11F methyl (3S,4S,5S)-3-azido-4-hydroxy-5-isobutyl-1-cyclohexene-1-carboxylate A solution of Example 11E (0.78 g, 2.5 mmol) and DBU (0.8 mL, 5.4 mmol) in THF (30 mL) was refluxed for 6 hours. The reaction mixture was cooled, washed with brine, dried (MgSO$_4$) filtered and concentrated. The concentrate was chromatographed through a plug of silica gel using hexanes/ethyl acetate (4/1) to afford the crude unsaturated ester.

Methanol (30 mL), H$_2$O (2 mL), sodium azide (0.5 g, 7.7 mmol) and NH$_4$Cl (0.2 g, 3.7 mmol) were added to the crude unsaturated ester dissolved in methanol (20 mL). The reaction mixture was refluxed for 5 hours, diluted with H$_2$O and extracted with ethyl acetate. The ethyl acetate layer was dried (MgSO$_4$), filtered and concentrated. The concentrate was purified by flash chromatography on silica gel using hexanes/ethyl acetate (1/1) to afford 0.52 g (81%) of the desired product as a colorless oil.

[α]$^P_{295}$ +250.00° (c 0.310, ethyl acetate).

$^1$H NMR (400 MHz, CDCl$_3$): δ6.79 (m, 1H), 3.96 (m, 1H), 3.80 (m, 1H), 3.76 (s, 3H), 2.41 (m, 1H), 2.17 (m, 1H), 2.10 (m, 2H), 1.71 (m, 1H), 1.34 (m, 1H), 1.25 (m, 1H), 0.91 (m, 6H). $^{13}$C NMR (100.6 MHz, CDCl$_3$): δ166.61, 134.23, 131.00, 70.94, 60.24, 51.97, 38.82, 32.24, 26.46, 24.81, 23.11, 21.99. HRMS (FAB/NBA): calcd (M+H)$^+$ for C$_{12}$H$_{20}$O$_3$N$_3$: 254.15047. Found: 254.15120.

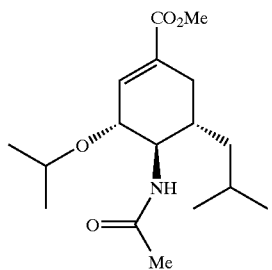

Example 11G methyl (3R,4R,5S)-4-(acetylamino)-5-isobutyl-3-isopropoxy-1-cyclohexene-1-carboxylate Methanesulfonyl chloride (0.24 mL, 3.1 mmol) was added dropwise to 0° C. a solution of Example 11F (0.5 g, 2.0 mmol) and triethylamine (0.6 mL, 4.3 mmol) in dichloromethane (20 mL). After stirring for 2 hours, the reaction mixture was washed with saturated NaHCO$_3$ solution, brine, dried (MgSO$_4$), filtered and concentrated to afford the crude mesylate.

Triphenylphosphine (0.8 g, 3.05 mmol) was slowly added to a room temperature solution of the crude mesylate in THF (30 mL). After stirring for stirring for 2 hours, water (0.5 mL) and triethylamine (0.6 mL, 4.3 mmol) were added. After stirring for 10 hours, the reaction mixture was concentrated. The concentrate was chromatographed on silica gel using ethyl acetate to afford the crude aziridine with Ph$_3$P=O as a contaminant.

Trityl chloride (0.85 g, 3.05 mmol) was added to a 0° C. solution of the crude aziridine and triethylamine (0.6 mL, 4.3 mmol) in dichloromethane (20 mL). After stirring for 2 hours, the reaction mixture was concentrated. The concentrate was chromatographed on silica gel using hexanes/ethyl acetate (10/1) to afford the crude tritylated aziridine with trityl chloride as a contaminant.

BF$_3$.Et$_2$O (0.3 mL, 2.4 mmol) was added to the crude tritylated aziridine in isopropanol (10 mL). After stirring for 2 hours at 70–80° C., the reaction mixture was cooled and concentrated to afford the crude isopropoxide.

Acetic anhydride (15 mL, 159 mmol) was added to the crude isopropoxide in room temperature pyridine (1.5 mL). After stirring for 12 hours, the reaction mixture was concentrated. The concentrate was dissolved in ethyl acetate (30 mL), washed with aqueous HCl (2N), saturated NaHCO$_3$ solution, and brine, dried (MgSO$_4$), filtered and concentrated. The concentrate was purified by flash chromatography on silica gel using hexanes/ethyl acetate (1/5) to afford 0.38 g (63%) of the desired product as a colorless oil.

[α]$^P_{295}$ +4.16° (c 0.120, ethyl acetate).

$^1$H NMR (400 MHz, CDCl$_3$): δ6.75 (m, 1H), 5.58 (d, J=8.7 Hz, 1H), 4.10 (m, 1H), 3.74 (m, 1H), 3.72 (s, 3H), 3.56 (m, 1H), 2.56 (m, 1H), 1.99 (s, 3H), 1.95 (m, 2H), 1.67 (m, 1H), 1.33 (m, 2H), 1.15 (2×d, J=6.1 Hz, 6H), 0.87 (2×d, J=6.6 Hz, 6H).

$^{13}$C NMR (100.6 MHz, CDCl$_3$): δ169.97, 167.04, 137.97, 130.20, 75.18, 71.12, 55.33, 51.74, 40.94, 34.06, 29.65, 24.42, 23.89, 23.44, 22.94, 22.27, 21.03.

HRMS (FAB/NBA): calcd (M+H)$^+$ for C$_{17}$H$_{30}$O$_4$N: 312.21750. Found: 312.21690.

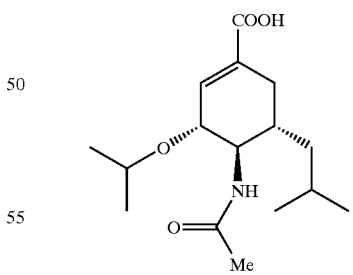

Example 11H (3R,4R,5R)-4-(acetylamino)-3-isopropoxy-5-isopropyl-1-cyclohexene-1-carboxylic acid Aqueous lithium hydroxide solution (0.1N, 20 mL) was added to a room temperature solution of Example 11G (160 mg, 0.51 mmol) in THF (6 mL). The solution was stirred for 12 hours, acidified to pH 5–6 with DOWEX® 50WX2-200 ion-exchange resin, filtered and concentrated. The concentrate was purified by flash chromatography on silica gel using acetic acid/ethyl acetate (1/5) to afford 145 mg (95%) of the desired product as a white solid.

m.p. 214–215° C.

[α]$^P_{295}$ −12.10° (c 0.595, methanol).

$^1$H NMR (400 MHz, CD$_3$OD): δ6.75 (m, 1H), 4.00 (m, 1H), 3.79 (h, J=6.1 Hz, 1H), 3.61 (m, 1H), 2.59 (m, 1H), 1.99 (s, 3H), 1.85 (m, 2H), 1.70 (m, 1H), 1.35 (m, 1H), 1.17 (2×d, J=6.1 Hz, 6H), 1.11 (m, 1H), 0.92 (2×d, J=6.6 Hz, 6H).

$^{13}$C NMR (100.6 MHz, CD$_3$OD): δ173.31, 170.07, 139.36, 131.96, 77.74, 73.34, 56.47, 42.46, 36.07, 31.33, 25.78, 24.51, 23.33, 22.76, 22.70, 21.48.

HRMS (FAB/NBA): calcd (M+H)$^+$ for C$_{16}$H$_{28}$O$_4$N: 298.20184. Found: 298.20110.

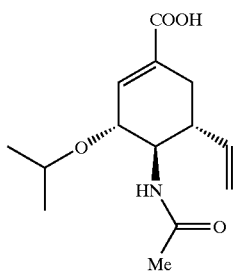

Example 12

(3R,4R,5R)-4-(acetylamino)-3-isopropoxy-5-vinyl-1-cyclohexene-1-carboxylic acid

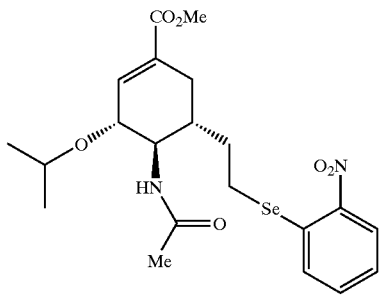

Example 12A methyl (3R,4R,5R)-4-(acetylamino)-3-isopropoxy-5-{2-[(2-nitrophenyl)selanyl]ethyl}-1-cyclohexene-1-carboxylate Tributylphosphine (73 μL, 0.29 mmol) was added dropwise to a solution of Example 9C (72 mg, 0.24 mmol) and ortho-nitrophenyl selenocyanate (66 mg, 0.29 mmol) in THF (8 mL). The reaction mixture was stirred for 2 hours, concentrated and the concentrate was purified by flash chromatography on silica gel using hexanes/ethyl acetate (1/3) to afford 110 mg (95%) of the desired product as a light yellow solid.

m.p. 170–171° C.

[α]$^P_{295}$ −28.12° (c 0.160, ethyl acetate).

$^1$H NMR (400 MHz, CDCl$_3$): δ8.27 (m, 1H), 7.52 (m, 2H), 7.32 (m, 1H), 6.80 (m, 1H), 5.52 (d, J=11.0 Hz, 1H), 4.15 (m, 1H), 3.79 (m, 1H), 3.76 (s, 3H), 3.61 (m, 1H), 3.08 (m, 1H), 2.87 (m, 1H), 2.70 (m, 1H), 2.09 (m, 3H), 1.97 (s, 3H), 1.75 (m, 1H), 1.19 (2×d, J=8.1 Hz, 6H).

$^{13}$C NMR (100.6 MHz, CDCl$_3$): δ170.19, 166.78, 138.03, 133.56, 129.68, 129.11, 126.29, 125.36, 74.79, 71.27, 55.01, 51.83, 36.45, 30.14, 29.24, 23.42, 22.99, 22.94, 22.17.

HRMS (FAB/NBA): calcd (M+H)$^+$ for C$_{21}$H$_{29}$O$_6$N$_2$$^{80}$Se: 485.11908. Found: 485.12120.

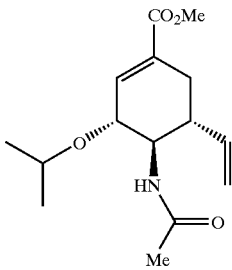

Example 12B methyl (3R,4R,5R)-4-(acetylamino)-3-isopropoxy-5-vinyl-1-cyclohexene-1-carboxylate Hydrogen peroxide (30%, 1.0 mL, 8.8 mmol) was added dropwise to a solution of Example 12A (58 mg, 0.12 mmol) in THF (10 mL). The reaction mixture was stirred for 12 hours, diluted with water, and extracted with ethyl acetate. The ethyl acetate was washed with brine, dried (MgSO$_4$), filtered, and concentrated. The concentrate was purified by flash column chromatography on silica gel (hexanes/ethyl acetate 1:4) to afford 30 mg (89%) of the desired product as a white solid.

m.p. 132–133° C.

[α]$^P_{295}$ −71.78° (c 0.350, ethyl acetate).

$^1$H NMR (400 MHz, CD$_3$OD): δ6.76 (m, 1H), 5.80 (s, br., 1H), 5.71 (m, 1H), 5.05 (m, 2H), 4.21 (m, 1H), 3.77 (m, 1H), 3.73 (s, 3H), 3.60 (m, 1H), 2.63 (m, 1H), 2.50 (m, 1H), 2.21 (m, 1H), 1.97 (s, 3H), 1.16 (2×d, J=6.1 Hz, 6H).

$^{13}$C NMR (100.6 MHz, CD$_3$OD): δ170.33, 166.74, 138.50, 138.35, 129.98, 116.48, 74.98, 71.35, 54.84, 51.79, 42.59, 30.75, 23.23, 23.02, 22.24.

HRMS (FAB/NBA): calcd (M+H)$^+$ for C$_{15}$H$_{24}$O$_4$N: 282.17053. Found: 282.17000.

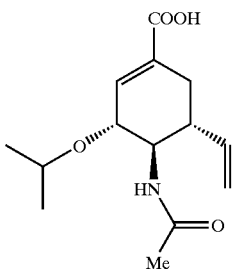

Example 12C (3R,4R,5R)-4-(acetylamino)-3-isopropoxy-5-vinyl-1-cyclohexene-1-carboxylic acid Aqueous lithium hydroxide (0.1N, 15 mL, 1.5 mmol) was added to a solution of Example 12B (28 mg, 0.10 mmol) in methanol (3 mL). After stirring for 12 hours, the reaction mixture was acidified to pH 5–6 with DOWEX® 50WX2-200 ion-exchange resin, filtered and concentrated. The concentrate was purified by flash column chromatography on silica gel (acetic acid/ethyl acetate 1:5) to afford 25.5 mg (96%) of the desired product as a white solid.

m.p. 206–207° C.

[α]$^D_{295}$ −90.95° (c 0.210, methanol).

$^1$H NMR (400 MHz, CD$_3$OD): δ6.69 (m, 1H), 5.69 (m., 1H), 5.08 (m, 2H), 4.08 (m, 1H), 3.80 (m, 2H), 2.47 (m, 2H), 2.17 (m, 1H), 1.93 (s, 3H), 1.15 (2×d, J=6.1 Hz, 6H).

$^{13}$C NMR (100.6 MHz, CD$_3$OD): δ173.12, 140.45, 138.25, 133.82, 116.73, 77.49, 73.28, 55.25, 45.05, 32.53, 23.38, 22.78, 22.73.

HRMS (FAB/NBA): calcd (M+H)$^+$ for C$_{14}$H$_{22}$O$_4$N: 268.15488. Found: 268.15560.

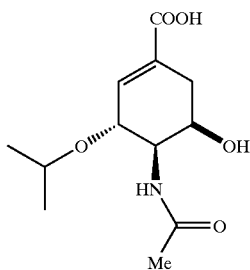

Example 13

(3R,4R,5R)-4-(acetylamino)-5-hydroxy-3-isopropoxy-1-cyclohexene-1-carboxylic acid

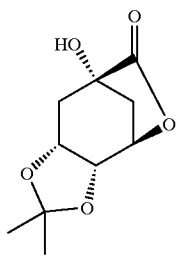

Example 13A (1R,2R,6R,8S)-8-hydroxy-4,4-dimethyl-3,5,10-trioxatricyclo[6.2.1.0$^{2,6}$]undecan-9-one A solution of quinic acid (10.0 g, 52.0 mmol), para-toluenesulfonic acid monohydrate (100 mg, 0.526 mmol) and 2,2-dimethoxypropane (20 mL, 162.9 mmol) in acetone (150 mL) was refluxed for 4 hours. The reaction mixture was concentrated, and the concentrate was dissolved in ethyl acetate (150 mL). The ethyl acetate layer was washed with saturated sodium bicarbonate and brine, dried (MgSO$_4$), filtered and concentrated. The concentrate was stored at 0° C. for several hours to afford 9.6 g (86%) of the desired product as white crystals.

$^1$H NMR (400 MHz, CDCl$_3$): δ4.71 (m, 1H), 4.50 (m, 1H), 4.30 (m, 1H), 2.89 (s, br, 1H), 2.65 (m, 1H), 2.34 (m, 2H), 2.18 (m, 1H), 1.52 (s, 3H), 1.33 (s, 3H).

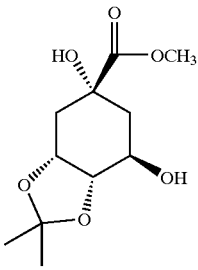

Example 13B methyl (3aR,5R,7R,7aS)-5,7-dihydroxy-2,2-dimethylhexahydro-1,3-benzodioxole-5-carboxylate Sodium methoxide (1.7 g, 29.9 mmol) was added to a room temperature solution of Example 13A (5.0 g, 26.3 mmol) in methanol (100 mL). After stirring for 1 hour, the reaction mixture was neutralized with acetic acid to pH 7. The reaction mixture was concentrated and the concentrate was purified by flash chromatography using ethyl acetate to afford 5.0 g (78%) of the desired product as a colorless oil.

$^1$H NMR (400 MHz, CDCl$_3$): 4.42 (m, 1H), 4.11 (m, 2H), 3.96 (m, 1H), 3.78 (s, 3H), 3.50 (s, br, 1H), 3.10 (s, br, 1H), 2.20 (m, 2H), 2.02 (m, 1H), 1.80 (m, 1H), 1.50 (s, 3H), −1.32 (s, 3H).

$^{13}$C NMR (100.6 MHz, CDCl$_3$): δ175.44, 109.05, 79.87, 73.79, 73.25, 67.90, 52.95, 38.85, 34.55, 28.05, 25.55.

HRMS (FAB/NBA): calcd (M+H)$^+$ for C$_{11}$H$_{19}$O$_6$: 247.11816. Found 247.11700.

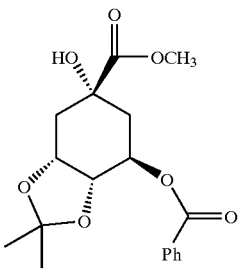

Example 13C methyl (3aR,5S,7R,7aR)-7-(benzoyloxy)-5-hydroxy-2,2-dimethylhexahydro-1,3-benzodioxole-5-carboxylate Benzoyl chloride (0.78 mL, 6.7 mmol) was added dropwise to 0° C. a solution of Example 13B (1.65 g, 6.7 mmol) and pyridine (0.82 mL, 10.1 mmol) in dichloromethane (40 mL). After stirring for 12 hours, the reaction mixture was washed with aqueous HCl (2N), saturated NaHCO$_3$ solution, and brine, dried (MgSO$_4$), filtered and concentrated. The concentrate was purified by flash chromatography using hexanes/ethyl acetate (3/2) to afford 2.02 g (86%) of the desired product as a white solid.

m.p. 109–110° C.

$^1$H NMR (400 MHz, CDCl$_3$): δ8.04–7.40 (m, 5H), 5.57 (m, 1H), 4.58 (m, 1H), 4.29 (m, 1H), 3.74 (s, 3H), 3.48 (s, 1H), 2.35 (m, 3H), 2.04 (m, 1H), 1.60 (s, 3H), 1.37 (s, 3H).

$^{13}$C NMR (100.6 MHz, CDCl3): δ174.56, 165.46, 132.93, 129.90, 129.58, 128.18, 109.48, 76.44, 73.61, 73.42, 70.91, 52.88, 36.70, 34.24, 27.80, 25.60.

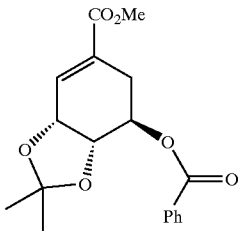

Example 13D
methyl (3aR,7R,7aS)-7-(benzoyloxy)-2,2-dimethyl-3a,6,7,7a-tetrahydro-1,3-benzodioxole-5-carboxylate Sulfuryl chloride (0.69 mL, 8.57 mmol) was added dropwise to a 0° C. solution of Example 13C (2.0 g, 5.71 mmol) and pyridine (2 mL, 24.8 mmol) in dichloromethane (60 mL). The reaction mixture was stirred for 3 hours, washed with HCl (1N), saturated sodium bicarbonate, and brine, dried (MgSO$_4$), filtered and concentrated to afford the crude desired product.

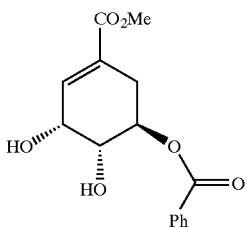

Example 13E
(1R,5R,6R)-5,6-dihydroxy-3-(methoxycarbonyl)-3-cyclohexen-1-yl benzoate Para-toluenesulfonic acid monohydrate (100 mg, 0.526 mmol) was added to a room temperature solution of Example 13D in methanol (50 mL). After stirring overnight, the reaction mixture was concentrated and the concentrate was purified by flash chromatography using ethyl acetate to afford 0.90 g (54%) of the desired product as a colorless oil.

$^1$H NMR (400 MHz, CDCl$_3$): δ8 02–7.42 (m, 5H), 6.93 (m, 1H), 5.48 (m, 1H), 4.54 (m, 1H), 4.06 (m, 1H), 3.77 (s, 3H), 2.99 (m, 1H), 2.52 (m, 1H).

$^{13}$C NMR (100.6 MHz, CDCl$_3$): δ166.31, 136.21, 133.29, 129.60, 129.48, 128.35, 70.37, 69.36, 66.09, 52.02, 28.10.

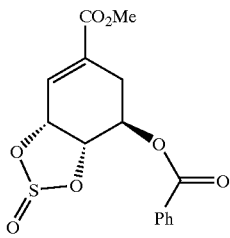

Example 13F
methyl (3aR,7R,7aS)-7-(benzoyloxy)-3a,6,7,7a-tetrahydro-1,3,2-benzodioxathiole-5-carboxylate 2-oxide Thionyl chloride (1.0 μL, 14.4 mmol) was added dropwise to a 0° C. solution of Example 13E (3.5 g, 12.0 mmol) and triethylamine (3.3 mL, 24.0 mmol) in dichloromethane (60 mL). After stirring for 30 minutes, the reaction mixture was washed with saturated NaHCO$_3$ solution, and brine, dried (MgSO$_4$) filtered and concentrated to afford the crude desired product.

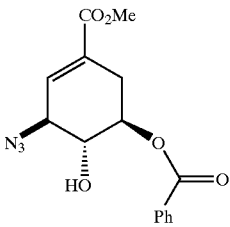

Example 13G
(1R,5S,6R)-5-azido-6-hydroxy-3-(methoxycarbonyl)-3-cyclohexen-1-yl benzoate Sodium azide (2.3 g, 36.0 mmol) was added to a solution of Example 13F in DMF (30 mL). After stirring at room temperature overnight, the reaction mixture was diluted with EtOAc, washed with brine, dried (MgSO$_4$), filtered and concentrated. The concentrate was purified by flash chromatography using hexanes/ethyl acetate (3/2) to afford 1.36 g (36%) of the desired product as a colorless oil.

IR (cm$^{-1}$): 2103.0 (N$_3$), 1731.5 (CO), 1714.9 (CO).

$^1$H NMR (400 MHz, CDCl$_3$): δ8.05–7.42 (m, 5H), 6.69 (m, 1H), 5.25 (m, 1H), 4.27 (m, 1H), 4.03 (m, 1H), 3.76 (s, 3H), 3.13 (m, 1H), 2.45 (m, 1H).

$^{13}$C NMR (100.6 MHz, CDCl$_3$): δ166.20, 165.49, 134.05, 133.38, 129.71, 129.63, 128.43, 128.38, 73.37, 71.77, 63.13, 52.20, 29.60.

HRMS (FAB, NBA): calcd (M+H)$^+$ for C$_{15}$H$_{15}$O$_5$N$_3$: 318.10901. Found 318.11040.

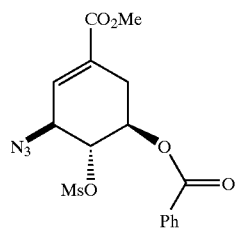

Example 13H
(1R,5S,6R)-5-azido-3-(methoxycarbonyl)-6-[(methylsulfonyl)oxy]-3-cyclohexen-1-yl benzoate Methanesulfonyl chloride (0.57 mL, 7.36 mmol) was added dropwise to a 0° C. sollution of Example 13G (1.54 g, 4.86 mmol) and triethylamiine (1.4 mL, 10.0 mmol) in dichloromethane (40 mL). After stirring for 2 hours, the reaction mixture was washed with saturated NaHCO$_3$ solution, brine, dried (MgSO$_4$), filte red and concentrated. The concentrate was purified by flash chromatography using hexanes/ethyl acetate (3/2) to afford 1.92 g (100%) of the desired product as a colorles is oil.

$^1$H NMR (400 MHz, CDCl$_3$): δ811–743 (m, 5H), 6.79 (m, 1H), 5.40 (m, 1H), 4.95 (m, 1H), 4.41 (m, 1H), 3.78 (s, 3H), 3.23 (m, 1H), 3.06 (s, 3H), 2.52 (m, 1H).

$^{13}$C NMR (100.6 MHz, CDCl$_3$): δ165.44, 164.87, 133.48, 132.25, 130.39, 129.87, 128.91, 128.41, 79.50, 68.22, 61.03, 52.38, 39.03, 29.78.

HRMS (FAB/NBA): calcd (M+H)+ for $C_{16}H_{18}O_7N_3S$: 396.08655. Found: 396.08530.

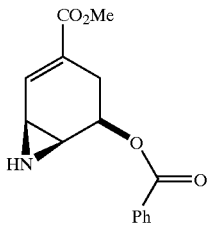

Example 13I methyl (1S,5R,6S)-5-(benzoylboxy)-7-azabicyclo[4.1.0]hept-2-ene-3-carboxylate Triphenylphosphine (2.0 g, 7.63 mmol) was slowly added to a solution of Example 13H (2.1 g, 5.31 mmol) in THF (30 mL). After stirring for 2 hours at room temperature, water (3.0 mL) and triethylamine (2.2 mL, 15.8 mmol) were added. After stirring for an additional 10 hours, the reaction mixture was concentrated. The concentrate was chromatographed using ethyl acetate to afford the desired product with $Ph_3P$ as a contaminant.

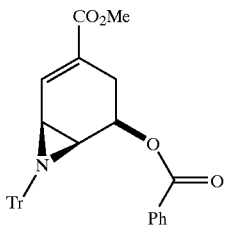

Example 13J methyl (1S,5R,6S)-5-(benzoyloxy)-7-trityl-7-azabicyclo[4.1.0]hept-2-ene-3-carboxylate Trityl chloride (1.78 g, 6.38 mmol) was added dropwise to Example 13I and triethylamine (1.4 mL, 10.0 mmol) in 0° C. dichloromethane (30 mL). After stirring for 2 hours, the reaction mixture was concentrated and the concentrate was chromatographed on silica gel using hexanes/ethyl acetate (9/1) to afford the desirled product with some trityl chloride as a contaminant.

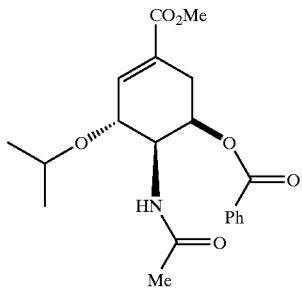

Example 13K (1R,5R,6R)-6-(acetylamino)-5-isopropoxy-3-(methoxycarbonyl)-3-cyclohexen-1-yl benzoate Example 13J and $BF_3 \cdot Et_2O$ (1.0 mL, 7.97 mmol) in isopropanol (20 mL) were heated to 70–80° C. for 2 hours and then concentrated. The concentrate was dissolved in dry pyridine (2.5 mL) and treated with acetic anhydride (3.0 mL). After stirring at room temperature for 12 hours, the reaction mixture was concentrated. The concentrate was dissolved in ethyl acetate (30 mL), washed with aqueous HCl (2N), saturated $NaHCO_3$ solution, and brine, dried ($MgSO_4$), filtered and concentrated. The concentrate was purified by flash chromatography using ethyl acetate to afford 0.645 g (34%) of the desired product as a colorless oil.

$[\alpha]^{25}_D$ −95.69° (c 1.160, EtOAc).

$^1$H NMR (400 MHz, $CDCl_3$): δ7.95–7.35 (m, 5H), 6.89 (m, 1H), 6.24 (d, J=8.4 Hz, 1H), 5.53 (m, 1H), 4.43 (m, 1H), 4.20 (m, 1H), 3.87 (hept, J=6.1 Hz, 1H), 3.69 (s, 3H), 2.81 (m, 1H), 2.64 (m, 1H), 1.93 (s, 3H), 1.19 (d, J=6.1 Hz, 6H).

$^{13}$C NMR (100.6 MHz, $CDCl_3$): δ170.37, 166.33, 165.57, 136.75, 133.11, 131.92, 131.83, 129.50, 128.46, 128.34, 128.30, 72.73, 71.57, 69.96, 51.92, 50.62, 28.33, 23.10, 22.74, 22.65.

HRMS (FAB, NBA): calcd (M+H)+ for $C_{20}H_{26}O_6N$: 376.17603. Found: 376.17730.

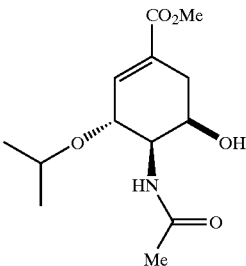

Example 13L methyl (3R,4R,5R)-4-(acetylamino)-5-hydroxy-3-isopropoxy-1-cyclohexene-1-carboxylate Potassium carbonate (40 mg, 0.29 mmol) was added to a room temperature solution of Example 13K (130 mg, 0.362 mmol) in methanol (30 mL). After stirring for 1 hour, the reaction mixture was filtered, and concentrated. The concentrate was purified by flash chromatography using ethyl acetate/acetone (4/1) to afford 47 mg (74w) of the desired product as a white solid.

m.p. 152–153° C.

$[\alpha]^{25}_D$ −128.93° (c 0.280, EtOAc).

$^1$H NMR (400 MHz, $CDCl_3$): δ6.83 (m, 1H), 5.79 (br, 1H) 4.32 (m, 2H), 3.81 (m, 2H), 3.75 (s, 3H), 2.62 (m, 1H), 2.50 (m, 1H), 2.05 (s, 3H), 1.18 (2×d, J=6.1 Hz, 6H).

$^{13}$C NMR (100.6 MHz, $CDCl_3$): δ171.59, 166.74, 136.63, 128.62, 71.89, 71.46, 67.01, 55.40, 51.87, 31.79, 23.38, 22.86, 22.21.

HRMS (FAB, NBA): calcd (M+H)+ for $C_{13}H_{22}O_5N$: 272.14981. Found: 272.15040.

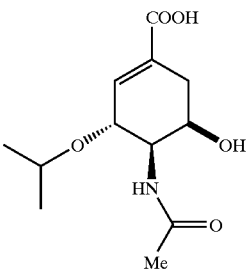

Example 13M (3R,4R,5R)-4-(acetylamino)-5-hydroxy-3-isopropoxy-1-cyclohexene-1-carboxylic acid Aqueous LiOH solution (0.1N, 15 mL) was added to a room temperature solution of Example 13L (23 mg, 0.085 mmol) in methanol (5 mL). After stirring for 10 hours, the reaction mixture was acidified to pH 5–6 with DOWEX® 50WX2-200 ion-exchange resin, filtered and concentrated. The concentrate was purified by flash chromatography using acetic acid/ethyl acetate (1/5) to afford 20.5 mg (94%) of the desired product as a white solid.

m.p. 64–65° C.

$[\alpha]^{25}_D$ −77.89° (c 0.190, MeOH).

$^1$H NMR (400 MHz, CD$_3$OD): δ6.67 (m, 1H), 4.15 (m, 1H), 4.13 (m, 1H), 4.07 (m, 1H), 3.87 (m, 1H), 2.59 (m, 1H), 2.48 (m, 1H), 2.00 (s, 3H), 1.18 (m, 6H).

$^{13}$C NMR (100.6 MHz, CD$_3$OD): δ177.69, 173.68, 134.88, 74.76, 72.96, 68.12, 54.91, 33.18, 23.25, 23.04, 22.69.

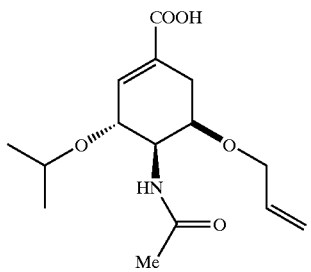

Example 14

(3R,4R,5R)-4-(acetylamino)-5-(allyloxy)-3-isopropoxy-1-cyclohexene-1-carboxylic acid

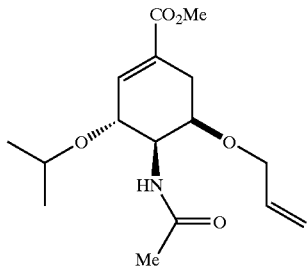

Example 14A methyl (3R,4R,5R)-4-(acetylamino)-5-(allyloxy)-3-isopropoxy-1-cyclohexene-1-carboxylate Sodium hydride (60%, 35 mg, 0.875 mmol) and allyl bromide (0.051 mL, 0.589 mmol) were added to a 0° C. solution of Example 13L (80 mg, 0.295 mmol) in THF (15 mL). After stirring for 5 hours, the reaction mixture was quenched with saturated NH$_4$Cl, and then extracted with ethyl acetate. The ethyl acetate layer was washed with brine, dried (MgSO$_4$), filtered and concentrated. The concentrate was purified by flash chromatography using ethyl acetate to afford 83 mg (90%) of the desired product as a white solid.

m.p. 102–103° C.

$[\alpha]^{25}_D$ −105.45° (c 0.220, EtOAc).

$^1$H NMR (400 MHz, CDCl$_3$): δ6.82 (m, 1H), 5.86 (m, 1H), 5.68 (d, J=7.8 Hz, 1H), 5.23 (m, 2H), 4.21 (m, 1H), 4.19–3.82 (m, 5H), 3.74 (s, 3H), 2.50 (m, 2H), 2.00 (s, 3H), 1.17 (2×d, J=6.1 Hz, 6H).

$^{13}$C NMR (100.6 MHz, CDCl$_3$): δ170.09, 166.67, 137.18, 134.30, 128.31, 117.36, 73.04, 72.72, 71.64, 69.83, 51.84, 50.95, 27.37, 23.39, 22.71, 22.62.

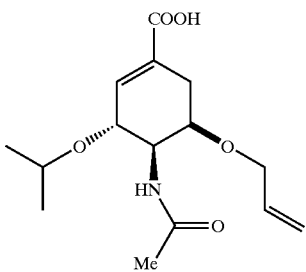

Example 14B (3R,4R,5R)-4-(acetylamino)-5-(allyloxy)-3-isopropoxy-1-cyclohexene-1-carboxylic acid Aqueous LiOH solution (0.1N, 15 mL) was added to a room temperature solution of Example 13L (23 mg, 0.085 mmol) in methanol (5 mL). After stirring for 10 hours, the reaction mixture was acidified to pH 5–6 with DOWEX® 50WX2-200 ion-exchange resin, filtered and concentrated. The concentrate was purified by flash chromatography using acetic acid/ethyl acetate (1/5) to afford 26 mg (92%) of the desired product as a white solid.

m.p. 70–71° C.

$[\alpha]^{25}_D$ −113.12° (c 0.160, MeOH).

$^1$H NMR (400 MHz, CD$_3$OD): δ6.67 (m, 1H), 5.91 (m, 1H), 5.25 (m, 1H), 5.16 (m, 1H), 4.13 (m, 2H), 4.05 (m, 2H), 3.87 (m, 2H), 2.57 (m, 2H), 1.99 (s, 3H), 1.18 (m, 6H).

$^{13}$C NMR (100.6 MHz, CD$_3$OD): δ173.47, 136.40, 134.96, 117.25, 75.26, 74.87, 72.94, 71.01, 53.06, 29.35, 23.22, 23.09, 22.55.

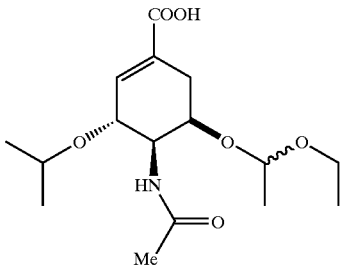

Example 15

(3R,4R,5R)-4-(acetylamino)-5-(1-ethoxyethoxy)-3-isopropoxy-1-cyclohexene-1-carboxylic acid

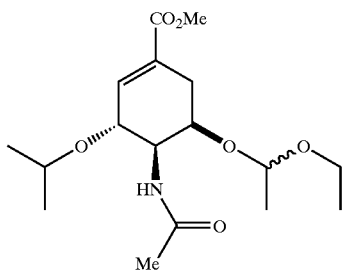

Example 15A methyl (3R,4R,5R)-4-(acetylamino)-5-(1-ethoxyethoxy)-3-isopropoxy-1-cyclohexene-1-carboxylate Trifluoroacetic acid (3 mL) was added to a room temperature solution of Example 13L (30 mg, 0.110 mmol) in vinyl ether (2 mL). After stirring overnight, potassium carbonate (10 mg) was added, and the reaction mixture was concentrated. The concentrate was purified by flash chromatography using ethyl acetate to afford 36.3 mg (96%) of a mixture of the desired products as a white solid.

m.p. 80–81° C.

$[\alpha]^{25}_D$ –85.20° (c 0.250, EtOAc).

$^1$H NMR (400 MHz, CDCl$_3$): δ6.80 (m, 1H), 6.03, 5.62 (br, 1H), 4.66 (m, 1H), 4.10 (m, 3H), 3.72 (m, 1H), 3.70 (ss, 3H), 3.50 (m, 2H), 2.50 (m, 2H), 1.98 (ss, 3H), 1.27 (m, 3H), 1.16 (m, 9H).

$^{13}$C NMR (100.6 MHz, CDCl$_3$): δ170.15, 169.90, 166.73, 166.56, 137.99, 136.57, 128.90, 127.66, 99.44, 99.37, 73.24, 72.61, 71.97, 71.83, 71.58, 69.80, 61.61, 61.37, 51.80, 51.07, 29.19, 28.54, 23.35, 22.76, 22.71, 22.64, 22.49, 20.60, 20.34, 15.53, 15.17, 15.02.

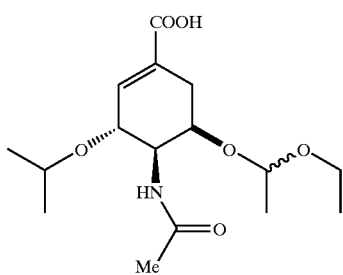

Example 15B (3R,4R,5R)-4-(acetylamino)-5-(1-ethoxyethoxy)-3-isopropoxy-1-cyclohexene-1-carboxylic acid Aqueous LiOH solution (0.1N, 15 mL) was added to a room temperature solution of Example 15A (23 mg, 0.085 mmol) in methanol (5 mL). After stirring for 10 hours, the reaction mixture was acidified to pH 5–6 with DOWEX® 50WX2-200 ion-exchange resin, filtered and concentrated. The concentrate was purified by flash chromatography using acetic acid/ethyl acetate (1/5) to afford 34 mg (83%) of a mixture of the desired products as a white solid.

m.p. 82–83° C.

$[\alpha]^{25}_D$ –80.00° (c 0.110, MeOH).

$^1$H NMR (400 MHz, CD$_3$OD): δ6.55 (m, 1H), 4.78 (m, 1H), 4.10 (m, 3H), 3.90 (m, 1H), 3.60 (m, 2H), 2.55 (m, 2H), 1.98 (ss, 3H), 1.27 (m, 3H), 1.17 (m, 9H).

$^{13}$C NMR (100.6 MHz, CD$_3$OD): δ175.08, 173.52, 173.35, 137.35, 132.10, 131.01, 100.59, 99.69, 75.17, 75.13, 72.67, 72.53, 72.47, 72.23, 62.14, 61.93, 54.02, 52.74, 30.86, 30.52, 23.29, 23.22, 23.17, 23.14, 22.62, 22.52, 20.96, 20.72, 16.06, 15.62, 15.56.

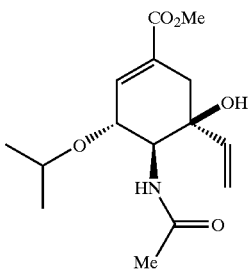

Example 16 methyl (3R,4S,5S)-4-(acetylamino)-5-hydroxy-3-isopropoxy-5-vinyl-1-cyclohexene-1-carboxylate

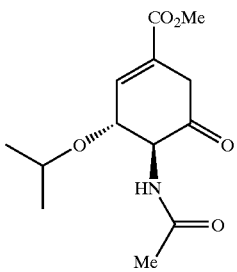

Example 16A methyl (3R,4S)-4-(acetylamino)-3-isopropoxy-5-oxo-1-cyclohexene-1-carboxylate PCC/Al$_2$O$_3$ can be added to a room temperature solution of Example 13L in dichloromethane. After stirring overnight, the reaction mixture can be filtered and concentrated. The concentrate can be purified by flash chromatography using ethyl acetate to afford the desired product.

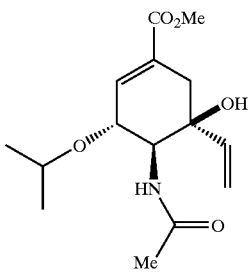

Example 16B methyl (3R,4S,5S)-4-(acetylamino)-5-hydroxy-3-isopropoxy-5-vinyl-1-cyclohexene-1-carboxylate Vinylmagnesium bromide can be added to a –78° C. solution of Example 16A in THF. The reaction mixture can be stirred for 2 hours and quenched with saturated aqueous NH₄Cl. The quenched reaction mixture can be extracted several times with dichloromethane. The combined dichloromethane layers can be dried (MgSO₄), filtered and concentrated. The concentrate can be purified by column chromatography to afford the desired product.

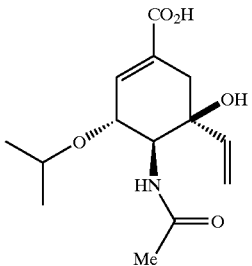

Example 16C (3R,4S,5S)-4-(-acetylamino)-5-hydroxy-3-isopropoxy-5-vinyl-1-cyclohexene-1-carboxylic acid The title compound can be prepared according to the method described in Example 10, substituting Example 16B for Example 1N to afford the desired product.

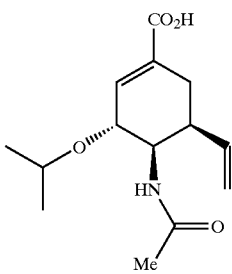

Example 17 methyl (3R,4R,5S)-4-(acetylamino)-3-isopropoxy-5-vinyl-1-cyclohexene-1-carboxylate

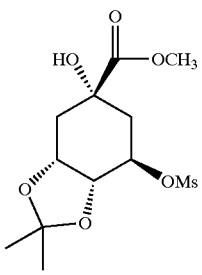

Example 17A methyl (3aR,5S,7R,7aR)-5-hydroxy-2,2-dimethyl-7-[(methylsulfonyl)oxy]hexahydro-1,3-benzodioxole-5-carboxylate Triethylamine (5.0 mL, 35.9 mmol) was added dropwise to a 0° C. solution of Example 13B (4.4 g, 17.9 mmol) and methanesulfonyl chloride (1.38 mL, 17.9 mmol) in dichloromethane (60 mL). After stirring overnight, the reaction mixture was washed with saturated sodium bicarbonate, brine, dried (MgSO₄), filtered and concentrated to afford the crude desired product.

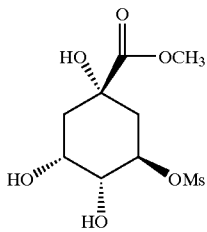

Example 17B methyl (1S,3R,4R,5R)-1,3,4-trihydroxy-5-[(methylsulfonyl)oxy]cyclohexanecarboxylate Para-toluenesulfonic acid monohydrate (100 mg, 0.526 mmol) was added to a room temperature solution of Example 17A in methanol (50 mL). After stirring overnight, the reaction mixture was concentrated and the concentrate was purified by flash column chromatography using ethyl acetate to afford 3.96 g (78%) of the desired product as a colorless oil.

¹H NMR (400 MHz, CDCl₃): δ4.96 (m, 1H), 4.21 (m, 1H), 3.77 (s, 3H), 3.66 (m, 1H), 3.15 (s, 3H), 2.40 (m, 1H), 2.07 (m, 3H).

¹³C NMR (100.6 MHz, CDCl₃): δ173.85, 79.55, 75.60, 73.08, 70.51, 53.20, 39.88, 38.26, 36.65.

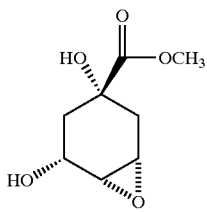

Example 17C methyl (1S,3S,5R,6R)-3,5-dihydroxy-7-oxabicyclo[4.1.0]heptane-3-carboxylate Potassium carbonate (400 mg, 2.9 mmol) was added to a room temperature mixture of Example 17B (3.0 g, 10.56 mmol) in methanol (100 mL). After stirring for 5 hours, the reaction mixture was filtered and concentrated. The concentrate was purified by flash column chromatography using ethyl acetate to afford 1.67 g (84%) of the desired product as a colorless oil.

¹H NMR (400 MHz, CDCl₃): δ4.15 (m, 1H), 3.78 (s, 3H), 3.42 (m, 2H), 2.32 (m, 1H), 2.15 (m, 1H), 1.88 (m, 2H).

¹³C NMR (100.6 MHz, CDCl₃): δ175.12, 73.41, 65.16, 54.29, 53.12, 52.88, 38.29, 32.67.

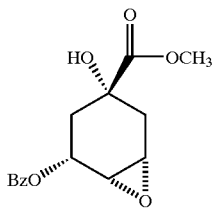

Example 17D
methyl (1S,3R,5R,6S)-5-(benzoyloxy)-3-hydroxy-7-oxabicyclo[4.1.0]heptane-3-carboxylate Benzoyl chloride (0.216 mL, 1.86 mmol) was added dropwise to a 0° C. solution of Example 17C (0.35 g, 1.86 mmol) and triethylamine (0.52 mL, 3.74 mmol) in dichloromethane (20 mL). The reaction mixture was stirred overnight at room temperature, washed with saturated NaHCO$_3$ solution, brine, dried (MgSO$_4$), filtered and concentrated. The concentrate was purified by flash column chromatography using hexanes/ethyl acetate (3/2) to afford 495 mg (91%) of the desired product as a colorless oil.

$^1$H NMR (400 MHz, 1H), 3.46 (m, 1H), 2.45 (m, 1H), 2.24 (m, 3H).
$^{13}$C NMR (100.6 MHz, CDCl$_3$): δ174.68, 165.84, 133.19, 129.70, 129.49, 128.28, 73.03, 68.50, 53.03, 52.50, 52.17, 34.99, 32.71.

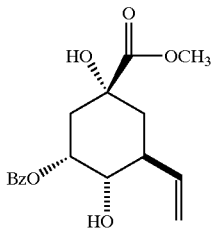

Example 17E
(1R,2S,3S,5R)-2,5-dihydroxy-5-(methoxycarbonyl)-3-vinylcyclohexyl benzoate Vinylmagnesium bromide can be added to a −78° C. suspension of CuI in THF. After stirring for 1 hour, a solution of Example 17D and BF$_3$·Et$_2$O in THF can be added. After stirring for 2 hours at −78° C., the reaction mixture can be quenched with saturated NH$_4$Cl. The reaction mixture can be extracted several times with dichloromethane and the combined dichloromethane layers are washed with brine, dried (MgSO$_4$), filtered and concentrated. The concentrate can be purified by flash column chromatography to afford the desired product.

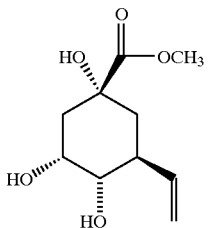

Example 17F
methyl (1R,3R,4S,5S)-1,3,4-trihydroxy-5-vinylcyclohexanecarboxylate Potassium carbonate can be added to a room temperature solution of Example 17E in methanol. After stirring for 1 hour, the reaction mixture can be filtered, and concentrated. The concentrate can be purified by flash chromatography to afford the desired product.

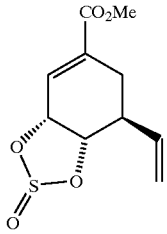

Example 17G
methyl (3aR,7S,7aS)-7-vinyl-3a,6,7,7a-tetrahydro-1,3,2-benzodioxathiole-5-carboxylate 2-oxide Thionyl chloride can be added dropwise to a 0° C. solution of Example 17F and triethylamine in dichloromethane. After stirring for 30 minutes, the reaction mixture can be washed with saturated NaHCO$_3$ solution, and brine, dried (MgSO$_4$) filtered and concentrated to afford the crude desired product.

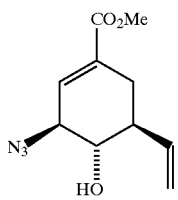

Example 17H
methyl (3S,4S,5S)-3-azido-4-hydroxy-5-vinyl-1-cyclohexene-1-carboxylate Sodium azide can be added to a solution of Example 17G in DMF. The reaction mixture can be stirred overnight at room temperature, diluted with EtOAc, washed with brine, dried (MgSO$_4$), filtered and concentrated. The concentrate can be purified by flash column chromatography to afford the desired product.

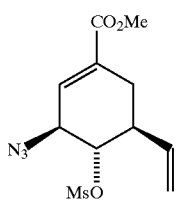

Example 17I
methyl (3S,4S,5S)-3-azido-4-[(methylsulfonyl)oxy]-5-vinyl-1-cyclohexene-1-carboxylate Methanesulfonyl chloride can be added dropwise to a 0° C. solution of Example 13H and triethylamine in dichloromethane. The reaction mixture can be stirred for 2 hours, washed with saturated NaHCO$_3$ solution, brine, dried (MgSO$_4$), filtered and concentrated. The concentrate can be purified by flash chromatography to afford the desired product.

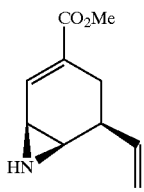

Example 17J
methyl (1S,5S,6R)-5-vinyl-7-azabicyclo[4.1.0]hept-2-ene-3-carboxylate Triphenylphosphine can be slowly added to a solution of Example 13I in THF. The reaction mixture can be stirred for 2 hours at room temperature, then water and triethylamine are added. The reaction mixture can be stirred for an additional 10 hours, then the reaction mixture can be concentrated. The concentrate can be chromatographed to afford the desired product with Ph₃P as a contaminant.

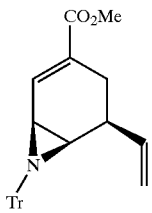

Example 17K
methyl (1S,5S,6R)-7-trityl-5-vinyl-7-azabicyclo[4.1.0]hept-2-ene-3-carboxylate Trityl chloride can be added dropwise to Example 13J and triethylamine in 0° C. dichloromethane. After stirring for 2 hours, the reaction mixture can be concentrated and the concentrate can be chromatographed on silica gel to afford the desired product with some trityl chloride as a contaminant.

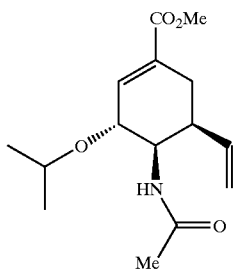

Example 17L
methyl (3R,4R,5S)-4-(acetylamino)-3-isopropoxy-5-vinyl-1-cyclohexene-1-carboxylate Example 17K and BF₃.Et₂O in isopropanol (20 mL) are heated to 70–80° C. for 2 hours and then concentrated. The concentrate can be dissolved in dry pyridine and treated with acetic anhydride. After stirring at room temperature for 12 hours, the reaction mixture can be concentrated. The concentrate can be dissolved in ethyl acetate, washed with aqueous HCl (2N), saturated NaHCO₃ solution, and brine, dried (MgSO₄), filtered and concentrated. The concentrate can be purified by flash chromatography to afford the desired product.

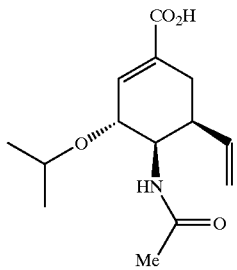

Example 17M
(3R,4R,5S)-4-(acetylamino)-3-isopropoxy-5-vinyl-1-cyclohexene-1-carboxylic acid The title compound can be prepared according to the method described in Example 10, substituting Example 17L for Example 1N to afford the desired product.

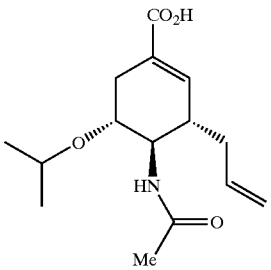

Example 18
(3S,4R,5R)-4-(acetylamino)-3-allyl-5-isopropoxy-1-cyclohexene-1-carboxylic acid

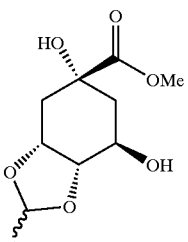

Example 18A
methyl (3aR,5R,7R,7aS)-5,7-dihydroxy-2-phenylhexahydro-1,3-benzodioxole-5-carboxylate The title compound can be prepared according to the method described in Example 13B, substituting Example 1A for Example 13A to afford the desired product.

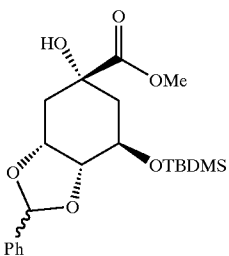

Example 18B
methyl (3aR,5S,7R,7aR)-7-{[(tert-butyl(dimethyl)silyl]oxy}-5-hydroxy-2-phenylhexahydro-1,3-benzodioxole-5-carboxylate Imidazole and TBDMSCl can be added to a 0° C. solution of Example 18A in DMF. After stirring overnight, the reaction mixture can be quenched with saturated NaHCO₃ solution and extracted several times with ethyl acetate. The combined ethyl acetate layers can then be washed with brine, dried (MgSO$_4$), filtered and concentrated. The concentrate can then be purified to afford the desired product.

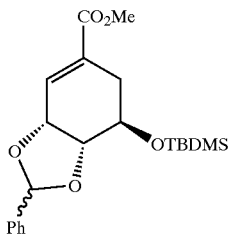

Example 18C methyl (3aR,7R,7aR)-7-{[tert-butyl(dimethyl)silyl]oxy}-2-phenyl-3a,6,7,7a-tetrahydro-1,3-benzodioxole-5-carboxylate Thionyl chloride and triethylamine can be added to a 0° C. solution of Example 18B in dichloromethane. After stirring overnight, the reaction mixture can be quenched with saturated NaHCO$_3$ solution and extracted several times with ethyl acetate. The combined ethyl acetate layers can then be washed with brine, dried (MgSO$_4$), filtered and concentrated. The concentrate can then be purified to afford the desired product.

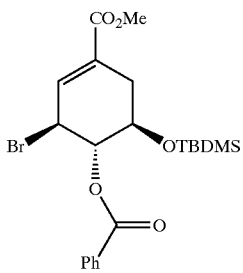

Example 18D (1S,2S,6R)-2-bromo-6-{[tert-butyl(dimethyl)silyl]oxy}-4-(methoxycarbonyl)-3-cyclohexen-1-yl benzoate The title compound can be prepared according to the method described in Example 1B, substituting Example 18C for Example 1A to afford the desired product.

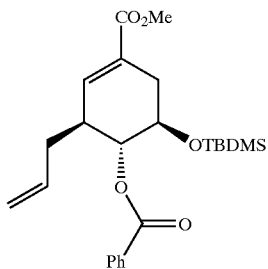

Example 18E (1R,2S,6R)-2-allyl-6-{[tert-butyl(dimethyl)silyl]oxy}-4-(methoxycarbonyl)-3-cyclohexen-1-yl benzoate Allyltributyltin and 2,2'-azobisisobutyronitrile can be added to Example 18D in benzene and refluxed for up to 24 hours. The reaction mixture can then be washed with saturated NaHCO$_3$, brine and dried (MgSO$_4$), filtered and concentrated. The concentrate can then be purified to afford the desired product.

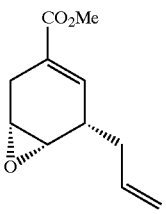

Example 18F methyl (1R,5S,6S)-5-allyl-7-oxabicyclo[4.1.0]hept-3-ene-3-carboxylate Potassium carbonate can be added to a room temperature solution of Example 18E in methanol and stirred over night. The reaction mixture can then be filtered, concentrated, and purified to yield the first intermediate compound. Methanesulfonyl chloride can then be added to a 0° C. solution of the first intermediate in dichloromethane. After stirring for up to 12 hours, the reaction mixture can then be washed with saturated NaHCO$_3$, dilute citric acid solution, water, and brine, dried (MgSO$_4$), filtered and concentrated. The concentrate can then be purified to afford the second intermediate. Tetrabutylammonium fluoride can then be added to a room temperature solution of the second intermediate in THF. After stirring for up to 12 hours, the reaction mixture can be diluted with ethyl acetate, washed with water, and brine, dried (MgSO$_4$), filtered and concentrated and purified to afford the desired product.

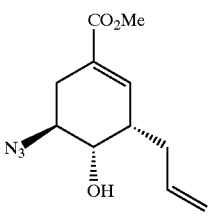

Example 18G methyl (3S,4S,5S)-3-allyl-5-azido-4-hydroxy-1-cyclohexene-1-carboxylate The title compound can be prepared according to the method described in Example 1J, substituting Example 18F for Example 1I to afford the desired product.

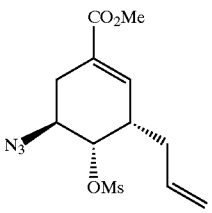

Example 18H
methyl (3S,4S,5S)-3-allyl-5-azido-4-[(methylsulfonyl)oxy]-1-cyclohexene-1-carboxylate The title compound can be prepared according to the method described in Example 1K, substituting Example 18G for Example 1J to afford the desired product.

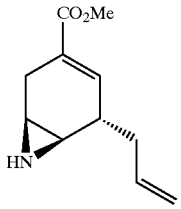

Example 18I
methyl (1S,5S,6R)-5-allyl-7-azabicyclo[4.1.0]hept-3-ene-3-carboxylate The title compound can be prepared according to the method described in Example 1L, substituting Example 18H for Example 1K to afford the desired product.

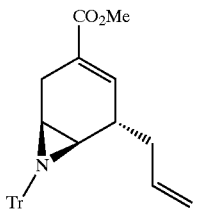

Example 18J
methyl (1S,5S,6R)-5-allyl-7-trityl-7-azabicyclo[4.1.0]hept-3-ene-3-carboxylate The title compound can be prepared according to the method described in Example 1M, substituting Example 18I for Example 1L to afford the desired product.

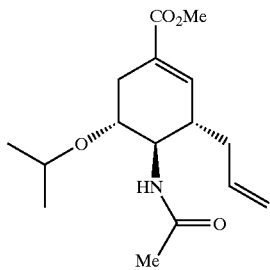

Example 18K
methyl (3S,4R,5R)-4-(acetylamino)-3-allyl-5-isopropoxy-1-cyclohexene-1-carboxylate The title compound can be prepared according to the method described in Example 1N, substituting Example 18J for Example 1M to afford the desired product.

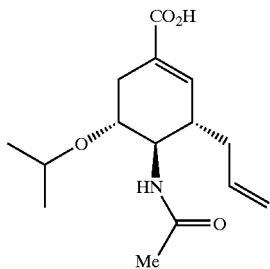

Example 18L
(3S,4R,5R)-4-(acetylamino)-3-allyl-5-isopropoxy-1-cyclohexene-1-carboxylic acid The title compound can be prepared according to the method described in Example 1O, substituting Example 18K for Example 1N to afford the desired product.

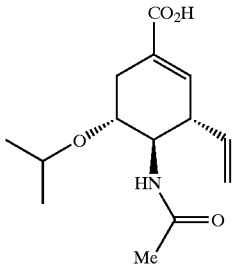

Example 19
(3S,4R,5R)-4-(acetylamino)-5-isopropoxy-3-vinyl-1-cyclohexene-1-carboxylic acid

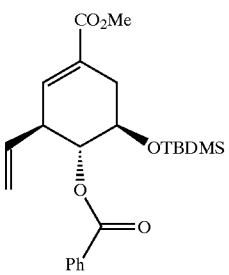

Example 19A
(1R,2S,6R)-6-{[tert-butyl(dimethyl)silyl]oxy}-4-(methoxycarbonyl)-2-vinyl-3-cyclohexen-1-yl benzoate Vinyltributyltin, and Pd(PPh₃)₄ can be added to Example 18D in THF. After stirring for 24 hours at elevated temperatures, the reaction mixture can be filtered and concentrated. The concentrate can then be purified to afford the desired product.

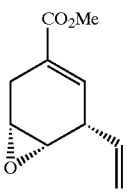

Example 19B
methyl (1R,5S,6S)-5-vinyl-7-oxabicyclo[4.1.0]hept-3-ene-3-carboxylate The title compound can be prepared according to the method described in Example 18F, substituting Example 19A for Example 18E to afford the desired product.

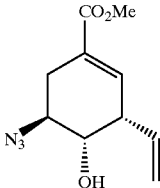

Example 19C
methyl (3S,4S,5S)-5-azido-4-hydroxy-3-vinyl-1-cyclohexene-1-carboxylate The title compound can be prepared according to the method described in Example 1J, substituting Example 19B for Example 1I to afford the desired product.

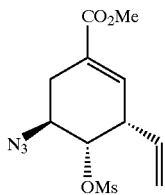

Example 19D
methyl (3S,4S,5S)-5-azido-4-[(methylsulfonyl)oxy]-3-vinyl-1-cyclohexene-1-carboxylate The title compound can be prepared according to the method described in Example 1K, substituting Example 19C for Example 1J to afford the desired product.

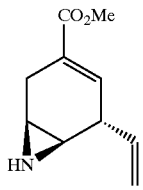

Example 19E
methyl (1S,5S,6R)-5-vinyl-7-azabicyclo[4.1.0]hept-3-ene-3-carboxylate The title compound can be prepared according to the method described in Example 1L, substituting Example 19D for Example 1K to afford the desired product.

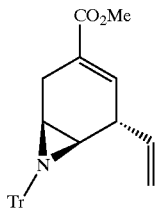

Example 19F
methyl (1S,5S,6R)-7-trityl-5-vinyl-7-azabicyclo[4.1.0]hept-3-ene-3-carboxylate The title compound can be prepared according to the method described in Example 1M, substituting Example 19E for Example 1L to afford the desired product.

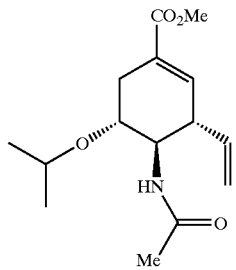

Example 19G
methyl (3S,4R,5R)-4-(acetylamino)-5-isopropoxy-3-vinyl-1-cyclohexene-1-carboxylate The title compound can be prepared according to the method described in Example 1N, substituting Example 19F for Example 1M to afford the desired product.

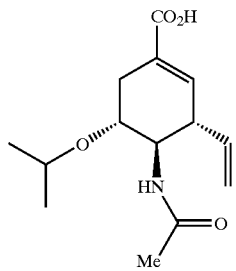

Example 19H
(3S,4R,5R)-4-(acetylamino)-5-isopropoxy-3-vinyl-1-cyclohexene-1-carboxylic acid The title compound can be prepared according to the method described in Example 1O, substituting Example 19G for Example 1N to afford the desired product.

Using the methods described above and the general knowledge of one skilled in the art, compounds of the invention can be prepared which are represented by taking one core from Table 1 (wherein Ac is acetyl), one Y substituent from Table 2, one $R^{14}$ substituent from Table 3, and one R substituent from Table 4.

TABLE 1

Substituents for Core Group

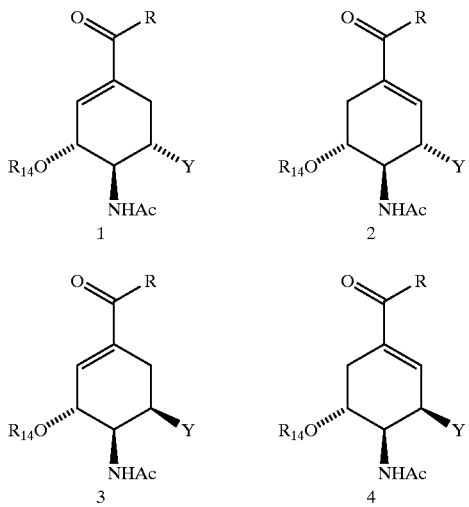

TABLE 1-continued

Substituents for Core Group

*Structures 5, 6, 7, 8 — cyclohexene core variants with C(O)R, R14O, NHAc, and OH/NH2/Y substituents*

TABLE 2

Substituents for Y Group

*Structures 1–28: various alkenyl and heterocyclic Y substituents*

TABLE 2-continued
Substituents for Y Group
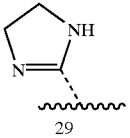 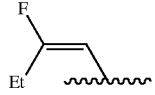 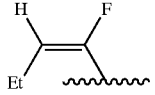 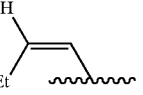
29 30 31 32
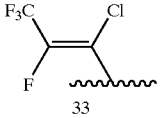 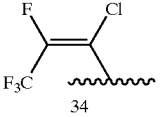 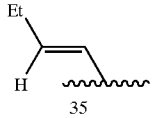 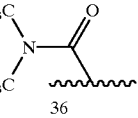
33 34 35 36
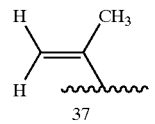 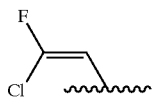 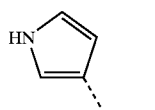 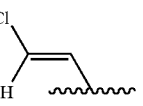
37 38 39 40
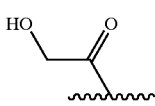 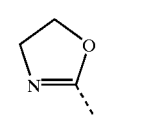 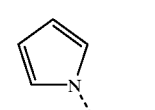 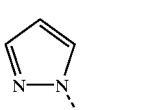
41 42 43 44
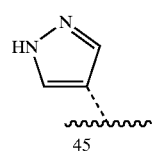 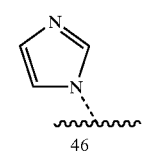 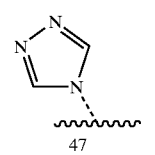 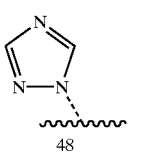
45 46 47 48
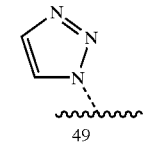 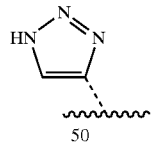 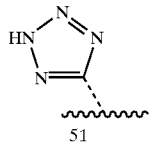 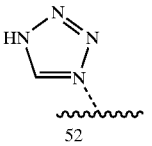
49 50 51 52
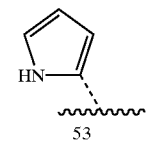 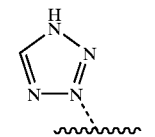 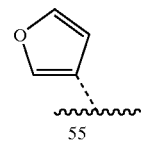 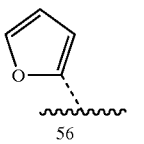
53 54 55 56
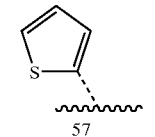 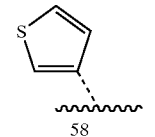 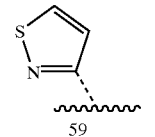 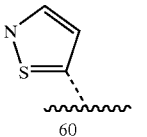
57 58 59 60
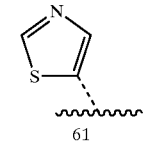 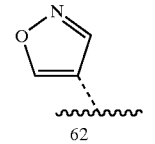 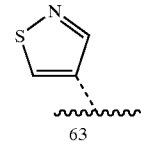 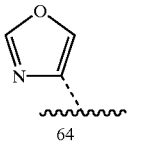
61 62 63 64
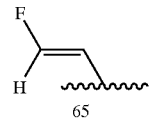 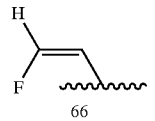 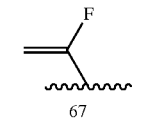 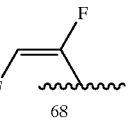
65 66 67 68

TABLE 2-continued

Substituents for Y Group

TABLE 2-continued
Substituents for Y Group
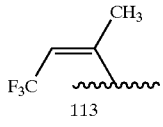

TABLE 2-continued
Substituents for Y Group
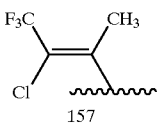
TABLE 3
Substituents for R¹⁴ Group
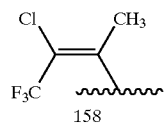
TABLE 3-continued
Substituents for R¹⁴ Group
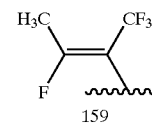

TABLE 3-continued

Substituents for $R^{14}$ Group

TABLE 3-continued

Substituents for R[14] Group (Chemical structures 59-94 depicting various substituent groups)

TABLE 3-continued

Substituents for $R^{14}$ Group

TABLE 3-continued

Substituents for $R^{14}$ Group

TABLE 3-continued

Substituents for $R^{14}$ Group

TABLE 3-continued

Substituents for $R^{14}$ Group

TABLE 3-continued
Substituents for $R^{14}$ Group
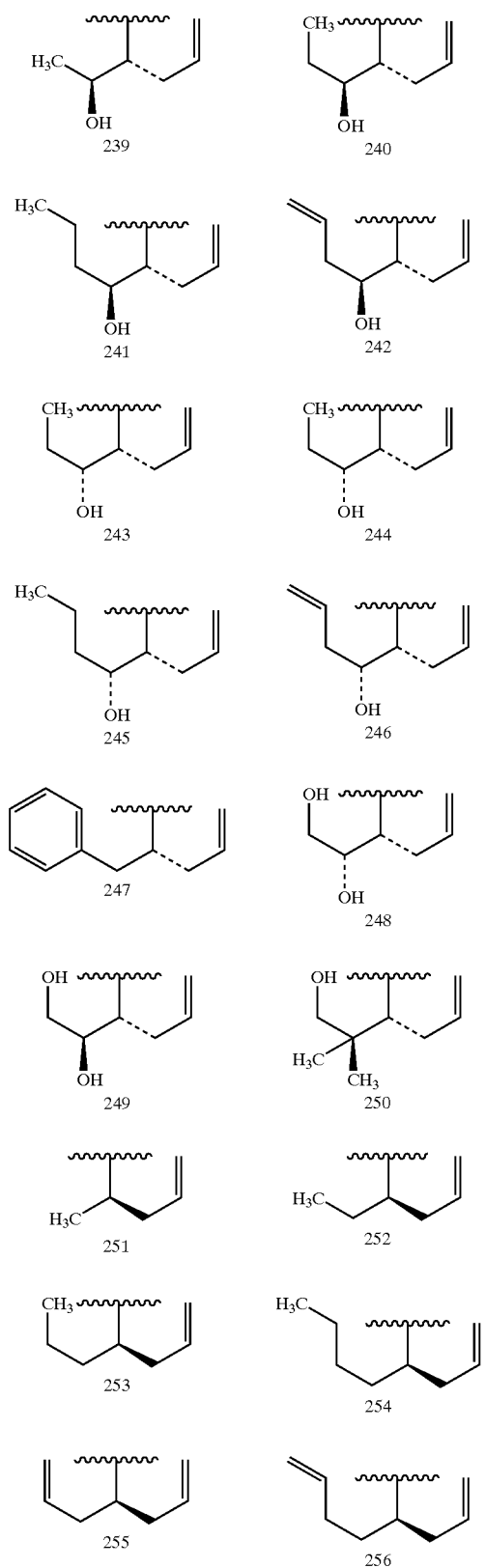
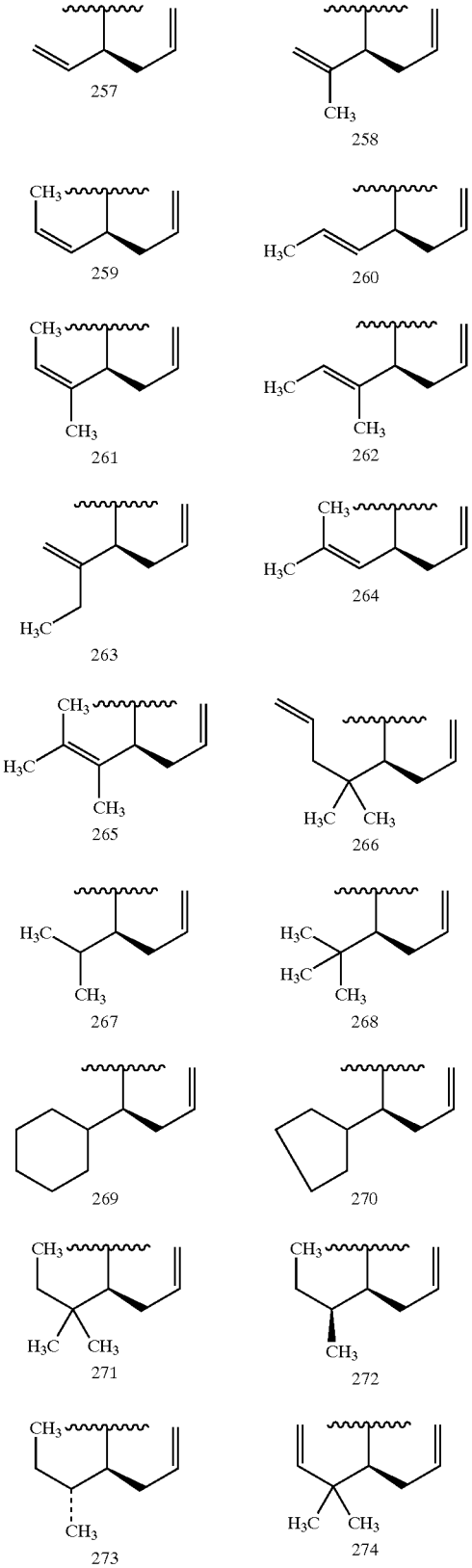

TABLE 3-continued

Substituents for R¹⁴ Group (Structures 275–296 depicting various hydroxyalkyl, alkoxyalkyl, and benzyl substituents with wavy bond attachment points.)

TABLE 4

Substituents for R Group

| | |
|---|---|
| —OH (1) | —OCH₃ (2) |
| —O—CH₂CH₃ (3) | —O—CH₂CH₂CH₃ (4) |
| —O—CH(CH₃)₂ (5) | —O—CH₂CH₂CH₂CH₃ (6) |
| —O—C(CH₃)₃ (7) | —O—CH₂CH(CH₃)₂ (8) |
| —O—CH₂C(CH₃)₃ (9) | —O—CH₂CH(CH₃)CH₃ (10) |
| —O—CH(CH₃)CH₂CH₃ (11) | —O—CH(CH₃)CH₂CH₃ (12) |
| —O—C(CH₃)₂CH₂CH₃ (13) | —O—CH₂CH₂N(CH₃)₂ (14) |
| —O—CH₂CH₂N(CH₂CH₃)₂ (15) | —O—CH₂—C₆H₅ (16) |

TABLE 4-continued
Substituents for R Group
| | |
|---|---|
| 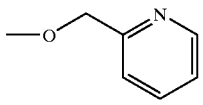 17 | 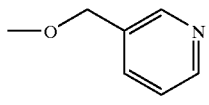 18 |
| 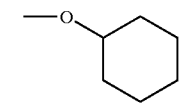 19 | 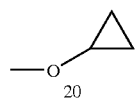 20 |
| 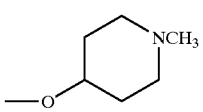 21 | 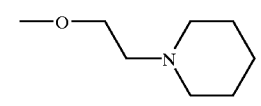 22 |
| 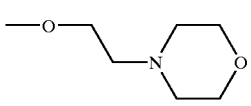 23 | 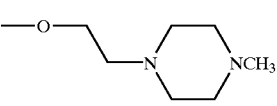 24 |
| 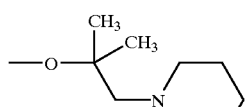 25 | 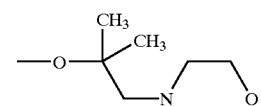 26 |
| 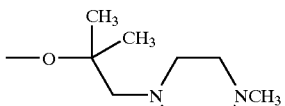 27 | 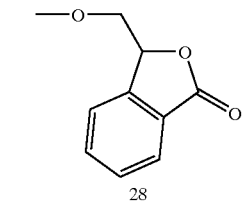 28 |
| 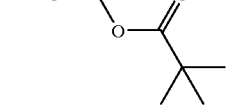 29 | 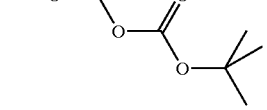 30 |
| 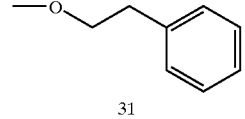 31 | 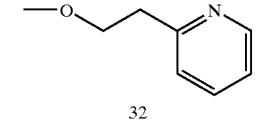 32 |
| 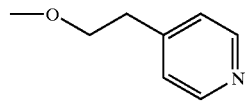 34 | 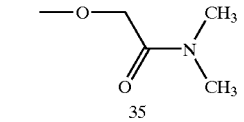 35 |
| 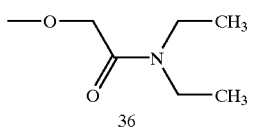 36 | 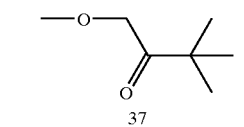 37 |
TABLE 4-continued
Substituents for R Group
| | |
|---|---|
| 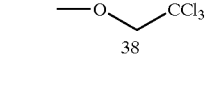 38 | 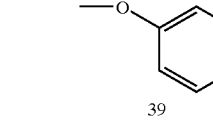 39 |
| 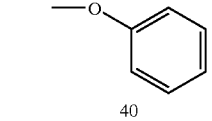 40 | 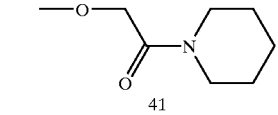 41 |
| 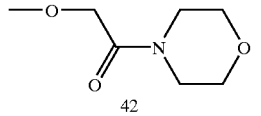 42 | 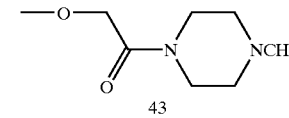 43 |
| 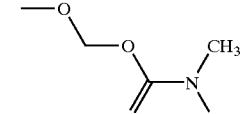 44 | 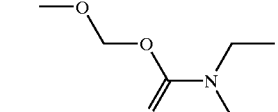 45 |
| 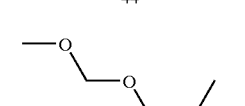 46 |  47 |
| 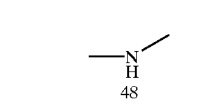 48 | 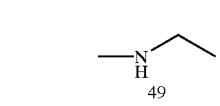 49 |
| 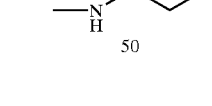 50 | 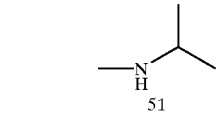 51 |
| 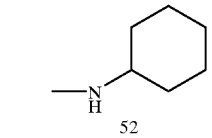 52 | 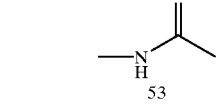 53 |
| 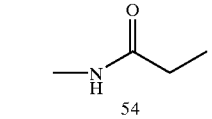 54 | 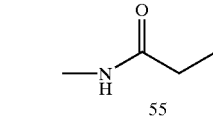 55 |
| 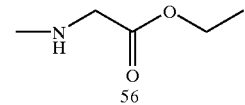 56 | 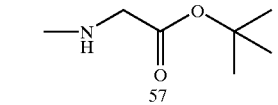 57 |
| 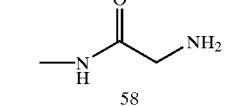 58 | 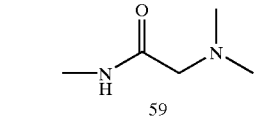 59 |

TABLE 4-continued

Substituents for R Group

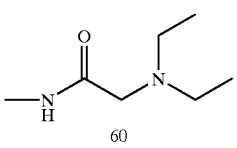
60

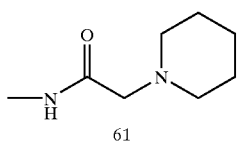
61

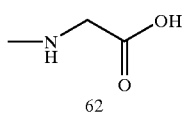
62

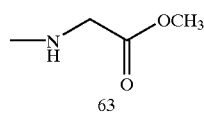
63

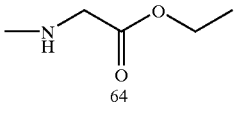
64

—N(H)-Ala-OH
65

—N(H)-Ala-OCH₃
66

—N(H)-Ala-OEt
67

—N(H)-Val-OH
68

—N(H)-Val-OCH₃
69

—N(H)-Val-OEt
70

—N(H)-Leu-OH
71

—N(H)-Leu-OCH₃
72

—N(H)-Leu-OEt
73

—N(H)-Ile-OH
74

—N(H)-Ile-OCH₃
75

—N(H)-Ile-OEt
76

—N(H)-Phe-OH
77

—N(H)-Phe-OCH₃
78

—N(H)-Phe-OEt
79

—N(H)-Tyr-OH
80

—N(H)-Tyr-OCH₃
81

—N(H)-Tyr-OEt
82

—N(H)-Asn-OH
83

—N(H)-Asn-OCH₃
84

—N(H)-Asn-OEt
85

—N(H)-Glu-OH
86

—N(H)-Glu-OCH₃
87

—N(H)-Glu-OEt
88

—N(H)-Gln-OH
89

—N(H)-Gln-OCH₃
90

—N(H)-Gln-OEt
91

—N(H)-Asp-OH
92

—N(H)-Asp-OCH₃
93

—N(H)-Asp-OEt
94

—N(H)-Lys-OH
95

—N(H)-Lys-OCH₃
96

—N(H)-Lys-OEt
97

—N(H)-Ser-OH
98

—N(H)-Ser-OCH₃
99

—N(H)-Ser-OEt
100

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of formula Ia or Ib

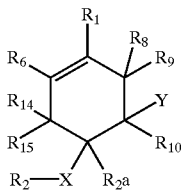

Ia

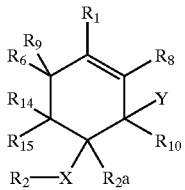

Ib or a pharmaceutically acceptable salt, ester, or prodrug thereof, wherein $R^1$ is selected from the group consisting of
(a) —CO₂H,
(b) —SO₃H,
(c) —SO₂H,
(d) —PO₃H₂,
(e) tetrazolyl,
(f) —C(=O)—NH—S(O)₂—R¹¹, and
(g) —SO₂N(T—R¹¹)R¹²;
   wherein T is selected from the group consisting of
   (i) a bond, (ii) —C(=O)—, (iii) —C(=O)O—,
   (iv) —C(=O)S—, (v) —C(=O)NR³⁶—,
   (vi) —C(=S)O—, (vii) —C(=S)S—, and
   (viii) —C(=S)NR³⁶—;
R¹¹ is selected from the group consisting of
   (i) C₁–C₁₂ alkyl, (ii) C₂–C₁₂ alkenyl, (iii) cycloalkyl, (iv) (cycloalkyl)alkyl, (v) (cycloalkyl)alkenyl, (vi) cycloalkenyl, (vii) (cycloalkenyl)alkyl, (viii) (cycloalkenyl)

alkenyl, (ix) aryl, (x) (aryl)alkyl, (xi) (aryl) alkenyl, (xii) heterocyclic, (xiii) (heterocyclic) alkyl, and (xiv) (heterocyclic)alkenyl; and $R^{12}$ and $R^{36}$ are independently cted from the group consisting of
(i) hydrogen, (ii) $C_1-C_{12}$ alkyl, (iii) $C_2-C_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl) alkenyl, (x) aryl, (xi) (aryl)alkyl, (xii) (aryl) alkenyl, (xiii) heterocyclic, (xiv) (heterocyclic) alkyl, and (xv) (heterocyclic)alkenyl;

X is selected from the group consisting of
(a) —C(=O)—N(R*)—, (b) —N(R*)—C(=O)—, (c) —C(=S)—N(R*)—, (d) —N(R*)—C(=S)—, (e) —N(R*)—SO$_2$—, and (f) —SO$_2$—N(R*)—, wherein R* is hydrogen, $C_1-C_3$ loweralkyl or cyclopropyl;

$R^2$ is selected from the group consisting of
(a) hydrogen, (b) $C_1-C_6$ alkyl, (c) $C_2-C_6$ alkenyl, (d) $C_3-C_6$ cycloalkyl, (e) $C_5-C_6$ cycloalkenyl, (f) halo $C_1-C_6$ alkyl and (g) halo $C_2-C_6$ alkenyl;

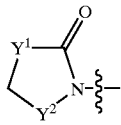

or $R^2$—X— is
wherein $y^1$ is —CH$_2$—, —O—, —S— or —NH— and $Y^2$ is —C(=O)— or —C(R$^{aa}$)(R$^{bb}$)— wherein $R^{aa}$ and $R^{bb}$ are independently selected from the group consisting of hydrogen, $C_1-C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R_{2a}$ is selected from the group consisting of
(a) hydrogen, (b) $C_1-C_6$ alkyl, (c) $C_2-C_6$ alkenyl, (d) halo $C_1-C_6$ alkyl, and (e) halo $C_2-C_6$ alkenyl; $R_{14}$ and $R_{15}$ are independently selected from the group consisting of
(i) hydrogen, (ii) $C_1-C_{12}$ alkyl, (iii) haloalkyl, (iv) hydroxyalkyl, (v) thiol-substituted alkyl, (vi) $R^{37c}$O-substituted alkyl, (vii) $R^{37c}$S substituted alkyl, (viii) aminoalkyl, (ix) ($R^{37c}$)NH-substituted alkyl, (x) ($R^{37a}$)($R^{37c}$)N-substituted alkyl, (xi) $R^{37a}$O—(O=)C-substituted alkyl, (xii) $R^{37a}$S—(O=)C-substituted alkyl, (xiii) $R^{37a}$O—(S=)C-substituted alkyl, (xiv) $R^{37a}$S—(S=)C-substituted alkyl, (xv) ($R^{37a}$O)$_2$—P(=O)-substituted alkyl, (xvi) cyanoalkyl, (xvii) $C_2-C_{12}$ alkenyl, (xviii) haloalkenyl, (xix) $C_2-C_{12}$ alkynyl, (xx) cycloalkyl, (xxi) (cycloalkyl)alkyl, (xxii) (cycloalkyl)alkenyl, (xxiii) (cycloalkyl)alkynyl, (xxiv) cycloalkenyl, (xxv) (cycloalkenyl)alkyl (xxvi) (cycloalkenyl) alkenyl, (xxvii) (cycloalkenyl)alkynyl, (xxviii) aryl, (xxxix)(aryl)alkyl, (xxx) (aryl)alkenyl, (xxxi) (aryl) alkynyl, (xxxii) heterocyclic, (xxxiii) (heterocyclic) alkyl, (xxxiv) (heterocyclic)alkenyl, (xxxv) (heterocyclic)alkynyl, (xxxvi) —O-alkyl, (xxxvii) —NHalkyl, (xxxviii) —NH$_2$, (xxxix) —N(alkyl)$_2$, (xxxx) —OH, (xxxxi) —Nacyl, (xxxxii) —Nalkylacyl, (xxxxiii) —NHcarbamoyl, (xxxxiv) —Nalkylcarbamoyl, (xxxxv) —NHcarbamidyl, and (xxxxvi) —Nalkylcarbamidyl;

$R^{37a}$ is selected from the group consisting of
(i) hydrogen, (ii) $C_1-C_{12}$ alkyl, (iii) haloalkyl, (iv) hydroxyalkyl, (v) alkoxyalkyl, (vi) $C_2-C_{12}$ alkenyl, (vii) haloalkenyl, (viii) $C_2-C_{12}$ alkynyl, (ix) cycloalkyl, (x) (cycloalkyl)alkyl, (xi) (cycloalkyl)alkenyl, (xii) (cycloalkyl) alkynyl, (xiii) cycloalkenyl, (xiv) (cycloalkenyl)alkyl, (xv) (cycloalkenyl) alkenyl, (xvi) (cycloalkenyl)alkynyl, (xvii) aryl, (xviii) (aryl)alkyl, (xix) (aryl)alkenyl, (xx) (aryl)alkynyl, (xxi) heterocyclic, (xxii) (heterocyclic)alkyl, (xxiii) (heterocyclic) alkenyl and (xxiv) (heterocyclic)alkynyl;

$R^{37c}$ at each occurrence is independently selected from the group consisting of
(i) hydrogen, (ii) $C_1-C_{12}$ alkyl, (iii) haloalkyl, (iv) $C_2-C_{12}$ alkenyl, (v) haloalkenyl, (vi) $C_2-C_{12}$ alkynyl, (vii) cycloalkyl, (viii) (cycloalkyl)alkyl, (ix) (cycloalkyl)alkenyl, (x) (cycloalkyl)alkynyl, (xi) cycloalkenyl, (xii) (cycloalkenyl)alkyl, (xiii) (cycloalkenyl) alkenyl, (xiv) (cycloalkenyl)alkynyl, (xv) aryl, (xvi) (aryl)alkyl, (xvii) (aryl)alkenyl, (xviii) (aryl)alkynyl, (xix) heterocyclic, (xx) (heterocyclic)alkyl, (xxi) (heterocyclic) alkenyl, (xxii) (heterocyclic)alkynyl, (xxiii) —C(=O)—$R^{14}$, (xxiv) —C(=S)—$R^{14}$, (xxv) -S(O)$_2$–$R^{14}$ and (xxvi) hydroxyalkyl;

Y is selected from the group consisting of
(a) $C_2-C_5$ alkenyl,
(b) $C_2-C_5$ haloalkenyl,
(c) $C_2-C_5$ alkynyl,
(d) $C_5$ cycloalkenyl,
(e) $C_5$ cycloalkenyl-$C_1$-to-$C_3$-alkyl,
(f) $C_5$ cycloalkenyl-$C_2$-to-$C_3$-alkenyl,
(g) phenyl,
(h) halo-substituted phenyl,
(i) —(CHR$^{39}$)$_n$C(=Q$^2$)R$^{22}$ wherein $R^{39}$ is hydrogen,
(j) a heterocyclic ring having from 3 to 6 ring atoms,
(k) OCH(CH$_3$)$_2$,
(l) CH$_2$CH=CH$_2$,
(m) (oxiran-2-yl)methyl,
(n) CH$_2$CH(OH)CH$_2$OH,
(o) CH$_2$CH(OH)CH$_2$N$_3$,
(p) CH$_2$CH$_2$OH,
(q) CH$_2$CH(CH$_3$)$_2$,
(r) CH=CH$_2$,
(S) OH,
(t) OCH$_2$CH=CH$_2$, and
(u) OCH(CH$_3$)OCH$_2$CH$_3$;
with the proviso that Y is not

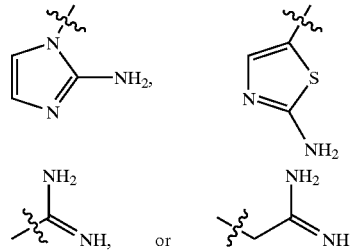

when n is 0, 1, or 2; and $Q^2$ is O, S, NR$^{25}$, or CHR$^{26}$;
$R^{22}$ is selected from the group consisting of
(i) hydrogen, (ii) methyl, (iii) ethyl, (iv) n-propyl, (v) isopropyl, (vi) hydroxy, (vii) thiol, (viii)

methoxy, (ix) ethoxy, (x) n-propoxy, (xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —N($R^{28a}$)($R^{28b}$), (xxiii) —$CH_2R^{29}$, (xxiv) aminomethyl, (xxv) hydroxymethyl, (xxvi) thiolmethyl, (xxvii) —$NHNH_2$, (xxviii) —N($CH_3$)$NH_2$, or (xxix) —NHNH($CH_3$);

$R^{25}$ is hydrogen, hydroxy, methyl, ethyl, amino, —CN, or —$NO_2$;

$R^{26}$ is hydrogen, methyl or ethyl;

$R^{28a}$ is hydrogen, hydroxy, methyl, ethyl, amino, —$NHCH_3$, —N($CH_3$)$_2$, methoxy, ethoxy, or —CN;

$R^{28b}$ is hydrogen, methyl or ethyl;

or $R^{28a}$, $R^{28b}$ and the nitrogen to which they are bonded taken together represent azetidinyl;

$R^{29}$ is hydrogen, hydroxy, thiol, methyl, ethyl, amino, methoxy, ethoxy, methylthio, ethylthio, methylamino or ethylamino;

with the proviso that when $Q^2$ is $CHR^{26}$ then $R^{22}$ is selected from the group consisting of hydrogen, —$CH_3$, —$C_2H_5$, —$C_3H_7$, —$OCH_3$, —$SCH_3$, —O—$C_2H_5$, and —S—$C_2H_5$;

$R^6$ is independently selected from the group consisting of
(a) hydrogen, (b) $C_1$-$C_{12}$ alkyl, (c) $C_2$-$C_{12}$ alkenyl, (d) cycloalkyl, (e) (cycloalkyl)alkyl, (f) (cycloalkyl) alkenyl, (g) cycloalkenyl, (h) (cycloalkenyl)alkyl, (i)(cycloalkenyl)alkenyl, (j) aryl, (k) (aryl)alkyl, (l) (aryl)alkenyl, (m) heterocyclic, (n) (heterocyclic) alkyl, and (o) (heterocyclic)alkenyl; and $R^8$ and $R^9$ are independently selected from the group consisting of
(a) hydrogen, (b) $C_1$-$C_6$ alkyl, (c) $C_2$-$C_6$ alkenyl, (d) $C_3$-$C_6$ cycloalkyl, (e) $C_3$-$C_6$ cycloalkenyl, (f) fluorine, and (g) —$NH_2$, with the proviso that the total number of atoms, other than hydrogen, in each of $R^8$ and $R^9$, is 6 atoms or less; and $R^{10}$ is selected from the group: consisting of
(a) hydrogen,
(b) $C_1$-$C_6$ alkyl,
(c) —$NH_2$, and
(d) —OH with the proviso that the total number of atoms, other than hydrogen, in each of $R^{10}$, is 6 atoms or less all of the foregoing with the proviso that when R*, $R^{2a}$, $R^6$, $R^8$, $R^9$, $R^{10}$, and $R^{14}$ are hydrogen, and X is —N(R*)—C(=O)—, the left end of which is attached to the cyclohexene ring, and $R^2$ is $C_1$-$C_2$ alkyl, and Y is OH, $R^{15}$ is other than $R^{37c}$O-substituted alkyl or $R^{37c}$O-substituted alkyl.

2. The compound according to claim 1 wherein said compound of formula Ia is selected from the group consisting of a compound of formula Ia' and Ia":

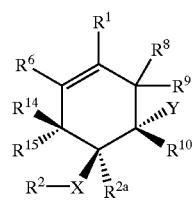

Ia'

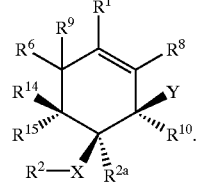

Ia"

3. The compound according to claim 1 wherein said compound of formula Ib is selected from the group consisting of a compound of formula Ib' and Ib":

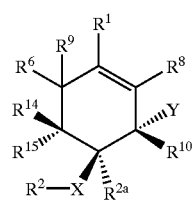

Ib'

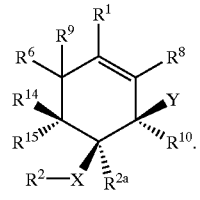

Ib"

4. The compound of claim 1 wherein $R_1$ is —$CO_2H$.
5. The compound of claim 1 wherein X is —N(R*)—C(=O)—, the left end of which is attached to the cyclohexene ring carbon, R* is hydrogen, and —$R_2$ is $C_1$-$C_6$ alkyl.
6. The compound of claim 4 wherein X is —N(R*)—C(=O)—, the left end of which is attached to the cyclohexene ring carbon, R* is hydrogen, and —$R_2$ is $C_1$-$C_6$ alkyl.
7. The compound of claim 1 wherein $R_{15}$ is —Oalkyl.
8. The compound of 1 wherein Y is selected from the group consisting of $C_2$-$C_5$ alkenyl, $C_2$-$C_5$ haloalkenyl, —(CHR$^{39}$)$_n$C(=$Q^2$)$R^{22}$, and heterocyclic ring having from 3 to 6 ring atoms.
9. The compound of claim 1 wherein Y is $C_2$-$C_5$ alkenyl.
10. The compound of claim 1 selected from the group consisting of:

(3R,4R,5S)-4-(acetylamino)-5-allyl-3-isopropoxy-1-cyclohexene-1-carboxylic acid;
(3R,4R,5S)-4-(acetylamino)-5-allyl-3-(1-ethylpropoxy)-1-cyclohexene-1-carboxylic acid;
(3R,4R,5R)-4-(acetylamino)-3-isopropoxy-5-(2-oxiranylmethyl)-1-cyclohexene-1-carboxylic acid;
(3R,4R,5R)-4-(acetylamino)-3-(1-ethylpropoxy)-5-(2-oxiranylmethyl)-1-cyclohexene-1-carboxylic acid;
(3R,4R,5R)-4-(acetylamino)-5-(2,3-dihydroxypropyl)-3-(1-ethylpropoxy)-1-cyclohexene-1-carboxylic acid;
(3R,4R,5R)-4-(acetylamino)-5-(3-azido-2-hydroxypropyl)-3-(1-ethylpropoxy)-1-cyclohexene -1-carboxylic acid;

[(1R,5R,6R)-6-(acetylamino)-5-(1-ethylpropoxy)-3-(methoxycarbonyl)-3-cyclohexen-1-yl]acetic acid;

(3R,4R,5R)-4-(acetylamino)-3-1-(1-ethylpropoxy)-5-(2-oxoethyl)-1-cyclohexene-1-carboxylic acid;

(3R,4R,5R)-4-(acetylamino)-5-(2-hydroxyethyl)-3-isopropoxy-1-cyclohexene-1-carboxylic acid;

(3R,4R,5R)-4-(acetylamino)-3-isopropoxy-5-(2-methoxy-2-oxoethyl)-1-cyclohexene-1-carboxylic acid;

(3R,4R,5R)-4-(acetylamino)-3-isopropoxy-5-isopropyl-1-cyclohexene-1-carboxylic acid;

(3R,4R,5R)-4-(acetylamino)-3-isopropoxy-5-vinyl-1-cyclohexene-1-carboxylic acid;

(3R,4R,5R)-4-(acetylamino)-5-hydroxy-3-isopropoxy-1-cyclohexene-1-carboxylic acid;

(3R,4R,5R)-4-(acetylamino)-5-(allyloxy)-3-isopropoxy-1-cyclohexene-1-carboxylic acid;

(3R,4R,5R)-4-(acetylamino)-5-(1-ethoxyethoxy)-3-isopropoxy-1-cyclohexene-1-carboxylic acid;

methyl (3R,4S,5S)-4-(acetylamino)-5-hydroxy-3-isopropoxy-5-vinyl-1-cyclohexene-1-carboxylate;

methyl (3R,4R,5S)-4-(acetylamino)-3-isopropoxy-5-vinyl-1-cyclohexene-1-carboxylate;

(3S,4R,5R)-4-(acetylamino)-3-allyl-5-isopropoxy-1-cyclohexene-1-carboxylic acid; and (3S,4R,5R)-4-(acetylamino)-5-isopropoxy-3-vinyl-1-cyclohexene-1-carboxylic acid;

or a pharmaceutically acceptable salt, ester or prodrug thereof.

11. A pharmaceutical composition for inhibiting influenza neuraminidase comprising a pharmaceutical carrier and a therapeutically effective amount of a compound of claim 1.

12. A pharmaceutical composition for treating an influenza infection comprising a pharmaceutical carrier and a therapeutically effective amount of a compound of claim 1.

13. A pharmaceutical composition for preventing an influenza infection comprising a pharmaceutical carrier and a therapeutically effective amount of a compound of claim 1.

14. A method for inhibiting neuraminidase from disease-causing microorganism comprising administering to a human or other mammal in need thereof a therapeutically effective amount of a compound of claim 1 or 11.

15. A method for treating an influenza infection comprising administering to a human or other mammal in need thereof a therapeutically effective amount of a compound of claim 1, 2, or 3.

* * * * *

UNITED STATES PATENT AND TRADEMARK OFFICE
CERTIFICATE OF CORRECTION

PATENT NO.    : 6,593,314 B1
DATED         : July 15, 2003
INVENTOR(S)   : Clarence J. Maring et al.

It is certified that error appears in the above-identified patent and that said Letters Patent is hereby corrected as shown below:

Column 159,
Line 4, replace "cted" with -- selected --.

Column 161,
Line 64, replace "R37c O-substituted" with -- R37c S-substituted --

Column 162,
Line 45, replace "-N(R*-C(=O)-" with -- -N(R*)-C(=O)- --

Column 163,
Line 3, replace "3-1-(1-ethylpropoxy)" with -- 3-(1-ethylpropoxy) --

Signed and Sealed this

Second Day of March, 2004

JON W. DUDAS
*Acting Director of the United States Patent and Trademark Office*